(12) United States Patent
Laufer et al.

(10) Patent No.: US 7,582,660 B2
(45) Date of Patent: *Sep. 1, 2009

(54) 2-THIO-SUBSTITUTED IMIDAZOLE DERIVATIVES AND THEIR USE IN PHARMACEUTICS

(75) Inventors: Stefan Laufer, Bleubeuren (DE); Hans-Günter Striegel, Blaustein (DE); Karola Tollmann, Brechen (DE); Wolfgang Albrecht, Ulm (DE)

(73) Assignee: c-a-i-r biosciences GmbH, Tuebingen (DE)

( * ) Notice: Subject to any disclaimer, the term of this patent is extended or adjusted under 35 U.S.C. 154(b) by 54 days.

This patent is subject to a terminal disclaimer.

(21) Appl. No.: 10/524,486

(22) PCT Filed: Aug. 20, 2003

(86) PCT No.: PCT/EP03/09219

§ 371 (c)(1),
(2), (4) Date: Nov. 17, 2005

(87) PCT Pub. No.: WO2004/018458

PCT Pub. Date: Mar. 4, 2004

(65) Prior Publication Data

US 2006/0235054 A1    Oct. 19, 2006

(30) Foreign Application Priority Data

Aug. 20, 2002  (DE) ................................ 102 38 045

(51) Int. Cl.
*A61K 31/4439* (2006.01)
*C07D 401/04* (2006.01)

(52) U.S. Cl. .................... 514/341; 546/274.1
(58) Field of Classification Search .............. 546/274.1; 514/341
See application file for complete search history.

(56) References Cited

U.S. PATENT DOCUMENTS

| | | | |
|---|---|---|---|
| 4,190,666 A | 2/1980 | Cherkofsky et al. | |
| 4,402,960 A | 9/1983 | Niedballa et al. | |
| 4,528,298 A | 7/1985 | Niedballa et al. | |
| 4,585,771 A | 4/1986 | Klose et al. | |
| 5,364,875 A | 11/1994 | Wilde | |
| 6,040,320 A | 3/2000 | Beers et al. | |
| 6,432,988 B1 * | 8/2002 | Laufer et al. ................. | 514/341 |
| 2004/0116416 A1 | 6/2004 | Laufer et al. | |

FOREIGN PATENT DOCUMENTS

| | | |
|---|---|---|
| DE | 35 04 678 | 8/1986 |
| DE | 101 14 775 | 10/2002 |
| DE | 102 22 103 | 11/2003 |
| EP | 0 004 648 | 10/1979 |
| EP | 0 005 545 | 11/1979 |
| EP | 0 236 628 | 9/1987 |
| EP | 0 372 445 | 6/1990 |
| JP | 1040467 | 2/1989 |
| SU | 1 415 725 | 10/1996 |
| WO | 91/10662 | 7/1991 |
| WO | 91/13876 | 9/1991 |
| WO | 93/14081 | 7/1993 |
| WO | 95/00501 | 1/1995 |
| WO | 96/03387 | 2/1996 |
| WO | 99/03837 | 1/1999 |
| WO | 00/17192 | 3/2000 |
| WO | 02/066458 | 8/2002 |
| WO | 02/076951 | 10/2002 |

OTHER PUBLICATIONS

Wagner et al., "Identification of, etc.," J. Org. Chem. 2003, 68, 4527-4530.*
Odeh, "Short Analytical Review, etc.," Clinical Immunology and Immunopathology, 83 (2), pp. 103-116, 1997.*
Campbell, et al. "Molecular targets, etc.," Immunology and Cell Biology (2003) 81, 354-366.*
Bondenson, "Review The Mechanisms, etc.," Gen. Pharmac., 29 (2), pp. 127-150, 1997.*
Laufer, Stefan et al. "Ones, Thiones, and N-Oxides: An Exercise in Imidazole Chemistry", Angew. Chem. Int. Ed., vol. 41, No. 13, pp. 2290-2293, XP002261426 2002.
Liverton, Nigel et al. "Design and Synthesis of Potent, Selective, and Orally Bioavailable Tetrasubstituted Imidazole Inhibitors of p38 Mitogen-Activated Protein Kinase", J. Med. Chem., vol. 42, pp. 2180-2190, XP002261427 1999.
Boehm, Jeffrey C. et al. "1-Substituted 4-Aryl-5-pyridinylimidazoles: A New Class of Cytokine Suppressive Drugs with Low 5-Lipoxygenase and Cyclooxygenase Inhibitory Potency", J. Med. Chem., vol. 39, pp. 3929-3927, XP002261428 1996.
Acta Chim., vol. 61, No. 1, pp. 69-77, XP002178027, English abstract only 1969.

(Continued)

*Primary Examiner*—Patricia L Morris
(74) *Attorney, Agent, or Firm*—Oblon, Spivak, McClelland, Maier & Neustadt, P.C.

(57) ABSTRACT

The invention relates to 2-thio-substituted imidazole derivatives of the formula I

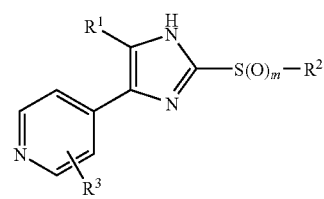

in which the radicals $R^1$, $R^2$, $R^3$ and m are as defined in the description. The compounds according to the invention have immunomodulating and/or cytokine-release-inhibiting action and are therefore suitable for treating disorders associated with a disturbed immune system.

23 Claims, No Drawings

OTHER PUBLICATIONS

Mustafa, A. et al. "Reactions with 4,5-Disubstituted 2-Mercaptoimidazoles and their Derivatives", Journal f. prakt. Chemie, vol. 314, No. 5-6, pp. 785-792, XP001088374 1972.

Gupta, G. D. et al. "Heterocyclic Systems Containing Bridgehead Nitrogen Atom: Part XLVI—Reaction of 4,5-Disubstituted 2-Mercaptoimidazoles with alpha-Halogenoketones & 1,2-Dibromoethane", Indian Journal of Chemistry, vol. 22B, pp. 268-269 1983.

Wilde, Richard G. et al. "Acyl CoA: Cholesterol Acyltransferase (ACAT) Inhibitors: Heterocyclic Bioisosteres for the Urea Group in DuP 128", Bioorganic & Medicinal Chemistry Letters, vol. 5, No. 2, pp. 177-180 1995.

Salama, M.A. et al. "Synthesis and Reactions of 4,5-Diaryl-2-Mercaptoimidazoles", Phosphorus and Sulfur, vol. 35, pp. 83-88 1988.

Beach, Dorothy et al. "Inhibition of Lipid Peroxidation Promoted by Iron(III) and Ascorbate", Archives of Biochemistry and Biophysics, vol. 297, No. 2, pp. 258-264 1992.

Maduskuie, Thomas P. et al. "Design, Synthesis, and Structure-Activity Relationship Studies for a New Imidazole Series of J774 Macrophage Specific Acyl-CoA:Cholesterol Acyltransferase (ACAT) Inhibitors", J. Med. Chem., vol. 38, pp. 1067-1083, XP001084249 1995.

Mloston, Grzegorz et al. "Trapping of a Thiocarbonyl Ylide with Imidazolethiones, Pyrimidinethione, and Thioamides", Helvetica Chimica Acta, vol. 82, pp. 290-296, XP002209741 1999.

Mloston, Grzegorz et al. "First Examples of Reactions of Azole N-Oxides with Thioketones: A Novel Type of Sulfur-Transfer Reaction", Helvetica Chimica Acta, vol. 81, pp. 1585-1595 1998.

Donat, C. et al. "Archiv der Pharmazie", Arch. Pharm. Pharm. Med. Chem., vol. 333, Suppl. 1, pp. 1-40 2000.

* cited by examiner

2-THIO-SUBSTITUTED IMIDAZOLE DERIVATIVES AND THEIR USE IN PHARMACEUTICS

The present invention relates to 2-thio-substituted imidazole derivatives having immunomodulating and cytokine-release-inhibiting action, to pharmaceutical compositions comprising these compounds and to their use in pharmacy.

Pharmacologically active imidazole compounds with anti-inflammatory activity are already known. Thus, inter alia, compounds having 4,5-di(hetero)arylimidazole moieties have been examined more closely, and various pharmaceutical actions thereof have been described. Also known are compounds which are substituted in the 2-position. U.S. Pat. No. 4,585,771 discloses 4,5-diphenylimidazole derivatives which are substituted in the 2-position by a pyrrolyl, indolyl, imidazolyl or thiazolyl radical and which have anti-inflammatory and antiallergic activity. U.S. Pat. Nos. 4,528,298 and 4,402,960 describe 4,5-di(hetero)arylimidazole derivatives which are substituted in the 2-position via a thio, sulfinyl or sulfonyl group by a phenyl, pyridyl, N-oxypyridyl, pyrimidyl, thiazolyl or thienyl radical and which have anti-inflammatory and antiallergic activity. U.S. Pat. Nos. 4,461,770, 4,528,298 and 4,584,310 (EP 004 648 A) describe 4-(5-aryl)-5-(4-heteroaryl)imidazole derivatives which are substituted in the 2-position via a thio, sulfinyl or sulfonyl group by a substituted or unsubstituted aliphatic hydrocarbon and which, inter alia, have anti-inflammatory action. Imidazole compounds having immunomodulating and cytokine-release-inhibiting action are described in WO 02/066458, WO 02/076951 and DE 102 22 103. Further imidazole compounds having anti-inflammatory action are described in WO 96/03387, EP 005 545 (U.S. Pat. Nos. 4,440,776; 4,355,039; 4,269,847), EP 236 628 (U.S. Pat. No. 4,686,231), DE 35 04 678, U.S. Pat. Nos. 4,190,666, 4,402,960 and 4,585,771. EP 372 445 (U.S. Pat. Nos. 5,318,984; 5,166,214) and U.S. Pat. No. 5,364,875 describe imidazole compounds having antihypercholesterolemic activity.

WO 00/17192 (DE 198 42 833) relates to 4-heteroaryl-5-phenylimidazole derivatives which are substituted in the 2-position by a phenylalkylthio group. These compounds act as anti-inflammatories and inhibitors of cytokine release. WO 99/03837 and WO 93/14081 describe 2-substituted imidazoles which inhibit the synthesis of a number of inflammatory cytokines. The compounds described in WO 93/14081 have in the 2-position, attached via a sulfur atom, a phosphorus-containing substituent or an aryl or heteroaryl substituent. WO 91/10662 and WO 91/13876 describe imidazole derivatives which inhibit the acyl-coenzyme A:cholesterol-O-acyl transferase and binding of thromboxane $TxA_2$. WO 95/00501 describes imidazole derivatives which can be used as cyclooxygenase inhibitors.

J. Med. Chem. 1996, 39, 3927-37 describes compounds having 5-lipoxygenase- and cyclooxygenase-inhibiting action, 2-(4-methylsulfinylphenyl)-4-(4-fluorophenyl-5-(pyrid-4-yl)imidazole also having cytokine-inhibiting action.

Further 2-thio-substituted imidazole derivatives are described in JP 01-040 467, SU 1 415 725, Acta Chim. 1969, 61, 69-77, J. prakt. Chem. 1972, 314, 785-792 and DE 101 14 775, Indian J. Chem., Sect. B, 1983, 22B(3), 268-269, Bioorganic & Medicinal Chem. Lett., Vol 5, No. 2, 177-180, 1995, Phosphorus Sulfur 1988, 35(1-2), 83-88, Arch. Biochem. Biophys. Vol. 297, 258-264, 1992, J. Med. Chem. 1995, 38, 1067-1083, Helv. Chim. Acta 82, 1999, 290-296, Helv. Chim. Acta 81, 1998, 1585-1595.

In spite of the fact that numerous compounds are known, there is therefore still a need for compounds having anti-inflammatory action which inhibit cytokine release.

It is an object of the invention to provide such compounds.

Surprisingly, it has now been found that certain 2-substituted imidazole derivatives have high immunomodulating and/or cytokine-release inhibiting activity.

Accordingly, the present invention provides 2-thio-substituted imidazole derivatives of the formula I

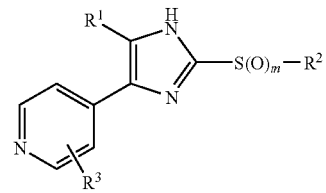

in which $R^1$ is $C_1$-$C_6$-alkyl, $C_3$-$C_7$-cycloalkyl or aryl which is unsubstituted or substituted by a halogen atom, by $C_1$-$C_6$-alkyl or by halo-$C_1$-$C_6$-alkyl;

$R^2$ is selected from the group consisting of
  a) aryl-$C_1$-$C_4$-alkyl, where the aryl radical may have one, two or three substituents independently of one another selected from the group consisting of $C_1$-$C_6$-alkyl, $C_1$-$C_6$-alkoxy, halogen, $C_1$-$C_6$-alkylsulfanyl, $C_1$-$C_6$-alkylsulfinyl, $C_1$-$C_6$-alkylsulfonyl and hydroxyl, and
  b) $C_1$-$C_6$-alkyl which is unsubstituted or substituted by CN or halogen;

c)

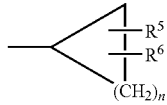

d)

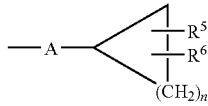

$R^3$ is selected from the group consisting of
  a) $NR^4R^{10}$;
  b) $NR^7COR^{10}$;
  c) $NR^7COOR^{10}$;
  d) $NR^7CONR^7R^{10}$;
  e) $NR^7CONR^7COR^{10}$;
  f) $OR^{10}$;
  g) $S(O)_mR^{10}$;
  h) halogen;
  i) OH;
  j) $N_3$;
  k) $NH_2$;
  l) SH;
where $R^3$ is not OH, halogen, $C_1$-$C_6$-alkylthio or $C_1$-$C_6$-alkoxy if $R^2$ is phenyl-$C_1$-$C_4$-alkyl and the phenyl radical has a $C_1$-$C_6$-alkylsulfanyl, $C_1$-$C_6$-alkylsulfinyl or $C_1$-$C_6$-alkylsulfonyl substituent;

$R^4$ is H or a physiologically cleavable group, $R^5$ and $R^6$, which may be identical or different, are H, halogen, OH, $C_1$-$C_6$-alkoxy, $C_1$-$C_6$-alkyl, halo-$C_1$-$C_6$-alkyl, $C_1$-$C_6$-alkylsulfanyl, $NH_2$, $C_1$-$C_6$-alkylamino or di-$C_1$-$C_6$-alkylamino;

$R^7$ is $R^4$, $C_1$-$C_6$-alkyl or benzyl;

$R^{10}$ has one of the meanings below:

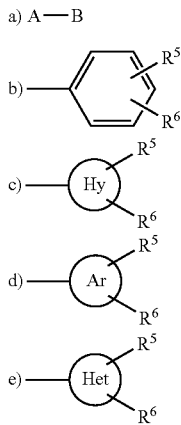

f) $C_1$-$C_6$-alkyl which is substituted by 2 or 3 phenyl groups;

g) trifluoromethyl (in particular, if $R^3$ is one of the radicals b) to f))

A is straight-chain or branched $C_1$-$C_6$-alkylene, $C_2$-$C_6$-alkenylene or $C_3$-alkynylene;

B is selected from the group consisting of

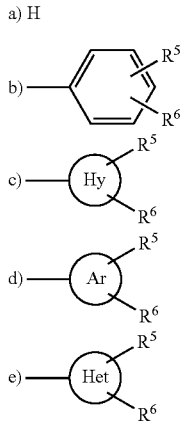

f) $OC_1$-$C_6$-alkyl;

g) $NR^{11}R^{12}$;

h) OH;

i) halogen;

j) $C_1$-$C_6$-alkylsulfanyl $R^{11}$ and $R^{12}$, which may be identical or different, are H, $C_1$-$C_6$-alkyl or phenyl;

Hy is a 3- to 10-membered non-aromatic mono-, bi- or tricyclic carbocycle which may or may not be fused with a benzene ring;

Ar is a 5- or 6-membered aromatic heterocycle which has 1, 2 or 3 heteroatoms independently of one another selected from the group consisting of O, S and N and which may or may not be fused with a benzene ring;

Het is a 5- or 6-membered non-aromatic heterocycle which has 1, 2 or 3 heteroatoms independently of one another selected from the group consisting of O, S and N, which may or may not be fused with a benzene ring and which may or may not be bridged bicyclically or tricyclically;

m is 0, 1 or 2;

n is 1, 2, 3, 4 or 5;

and the tautomers, optic isomers and physiologically acceptable salts thereof.

If the compounds according to the invention have centers of asymmetry, the scope of the invention includes both racemates and optical isomers (enantiomers, diastereomers). In the compounds according to the invention, the following tautomeric equilibrium may be present:

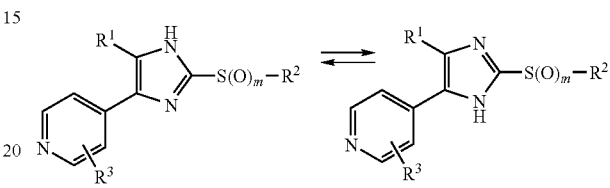

The invention embraces both tautomeric forms.

The invention also embraces the physiologically acceptable salts of the compounds of the formula I. In the present case, these are in particular acid addition salts. For acid addition salts, what is used are inorganic acids, such as hydrochloric acid, sulfuric acid or phosphoric acid, or organic acids, such as tartaric acid, citric acid, maleic acid, fumaric acid, malic acid, mandelic acid, ascorbic acid, gluconic acid and the like.

The term "alkyl" (also in combination with other groups, such as phenylalkyl, alkylsulfonyl, alkoxy, etc.) embraces straight-chain and branched alkyl groups having 1 to 6 or 1 to 4 carbon atoms, such as methyl, ethyl, n- and isopropyl, n-, iso- and t-butyl, sec-butyl, n-pentyl, isoamyl, neopentyl and n-hexyl. This applies correspondingly to "$C_1$-$C_6$-alkylene".

The term "carbocycle" embraces saturated or unsaturated non-aromatic monocyclic, bicyclic and tricyclic hydrocarbons. The hydrocarbons can be fused with one or two benzene rings. Monocyclic hydrocarbons are $C_3$-$C_6$-cycloalkyl, such as cyclopropyl, cyclopentyl, cyclohexyl. Examples of bi- and tricyclic hydrocarbons and benzo-fused carbocycles are indanyl, decalinyl, tetralinyl, fluorenyl, dihydroanthracenyl, dibenzosuberenyl, norbornyl or adamantyl. Examples of substituted carbocycles are methylcyclopropyl or methylcyclohexyl. Preference is given to unsubstituted radicals.

The term "aryl" embraces aromatic ring systems, such as phenyl or naphthyl.

The term "halogen" represents a fluorine, chlorine, bromine or iodine atom, in particular a fluorine or chlorine atom.

The term "halo-$C_1$-$C_6$-alkyl" embraces mono- or polyhalogenated straight-chain and branched alkyl groups having 1 to 6 and in particular 1 to 4 carbon atoms. Preferably, 1, 2, 3, 4 or 5 halogen atoms are present. Preferred halogen atoms are F and Cl. Examples of halo-$C_1$-$C_6$-alkyl are —$CH_2Cl$, —$CH_2CH_2Cl$, —$CH_2CCl_3$, —$CF_3$, —$CHF_2$, —$CH_2F$, —$CH_2CF_3$ and —$CF_2CF_3$. $CF_3$ is preferred.

A physiologically cleavable group is a group which can be cleaved from the remainder of the molecule under physiological conditions, enzymatically or chemically. Examples are —$COR^{14}$, —$CO_2R^{14}$, —$CONH_2$, —$CONHR^{14}$, —$CHR^{16}$—$OR^{14}$, —$CHR^{16}$—O—$COR^{14}$, —$COC(R^{16})_2$—OH, —$COR^{15}$, $SO_2R^{15}$ and —$SO_2R^{14}$, where $R^{14}$ is $C_1$-$C_6$-alkyl or $CF_3$, $R^{15}$ is phenyl or tolyl (in particular p-tolyl) and $R^{16}$ is H or $C_1$-$C_6$-alkyl.

The aromatic 5- or 6-membered heterocycle is in particular unsubstituted ($R^5$, $R^6$=H) or substituted 2-pyridyl, 3-pyridyl, 4-pyridyl, 2- or 3-thienyl, 2- or 3-furyl, thiazolyl, imidazolyl, oxazolyl, isothiazolyl, pyrazolyl, isoxazolyl, triazolyl or pyrimidyl. Preferred substituents are one or two groups independently of one another selected from the group consisting of halogen, in particular Cl, and $C_1$-$C_6$-alkyl. The substituent(s) are attached to a carbon atom or a nitrogen atom of the aromatic radical. Preferred are unsubstituted radicals. Examples of substituted radicals are chlorothienyl, in particular 5-chlorothien-2-yl, chlorofuryl, in particular 5-chlorofur-2-yl, examples of fused radicals are benzofuranyl, benzothiazolyl and benzothiophene.

The non-aromatic 5- or 6-membered heterocycle may be saturated or unsaturated. It is preferably unsubstituted or substituted tetrahydrofuranyl, tetrahydropyranyl, pyrrolidinyl, N-methylpyrrolidinyl, N-ethylpyrrolidinyl, piperazinyl or morpholinyl, where the heterocycle may be attached via a nitrogen heteroatom or a ring carbon atom or may be substituted. Preferred substituents are one or two radicals independently of one another selected from the group consisting of halogen, in particular Cl, and $C_1$-$C_6$-alkyl. Preference is given to unsubstituted radicals.

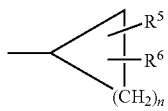

is substituted or unsubstituted cyclopropyl, cyclobutyl, cycloheptyl and, in particular, cyclopentyl and cyclohexyl. $R^5$ and $R^6$ are preferably independently of one another H, halogen or $C_1$-$C_6$-alkyl. Examples of substituted cycloalkyl groups are methylcyclopropyl or methylcyclohexyl. Preference is given to unsubstituted radicals.

Phenyl-$C_1$-$C_4$-alkyl is in particular benzyl, 1-phenylethyl or 2-phenylethyl.

$R^1$ is preferably a phenyl radical and in particular a halogen-, $CF_3$- or $C_1$-$C_6$-alkyl-substituted phenyl radical, a fluorine-substituted phenyl radical being particularly preferred. The substituent is preferably in the 3- and in particular in the 4-position. Examples of substituted phenyl radicals are 4-fluorophenyl, 2,4-difluorophenyl, 3-trifluoromethyl, 3-tolyl or 3-chlorophenyl.

$R^2$ is preferably a benzyl, $C_3$-$C_6$-cycloalkyl, $C_4$-$C_7$-methylcycloalkyl or $C_1$-$C_6$-alkyl radical, where the phenyl group of the benzyl radical may be substituted as indicated above. Preferred substituents of the phenyl group of the benzyl radical are $C_1$-$C_6$-alkylsulfanyl, $C_1$-$C_6$-alkylsulfinyl and $C_1$-$C_6$-alkylsulfonyl. Examples of $R^2$ are $CH_3$, $CH_3CH_2$, $(CH_3)_2CH$, $CH_2CN$, $CH_2CF_3$, $CF_3$ and cyclopropyl.

$R^3$ is preferably the radical of the formula

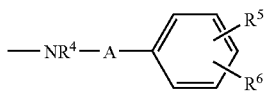

in which $R^4$, $R^5$ and $R^6$ and also A are as defined above. $R^5$ and $R^6$ are preferably H, methyl, methoxy or chlorine. If the phenyl ring of this group is substituted, the radicals $R^5$ and $R^6$ are preferably located in the 3- and/or 4-position.

Furthermore, $R^3$ is preferably
a) $NR^4R^{10}$, where $R^{10}$ is cyclopropyl, cyclopropylmethyl, cyclopentyl, cyclohexyl or cycloheptyl;
b) $NR^4R^{10}$, where $R^{10}$ is $C_1$-$C_6$-alkyl, in particular methyl, ethyl or isopropyl, or is 3,3-diphenylpropyl or 1,3-diphenylprop-2-yl;
c) $NR^4R^{10}$, where $R^{10}$ is A-B and B is OH, $C_1$-$C_6$-alkyoxy, $NR^{11}R^{12}$ or phenyl;
d) $NR^7COR^{10}$, where $R^{10}$ is A-B and B is phenyl;
e) $NR^7COOR^{10}$, where $R^{10}$ is $C_1$-$C_6$-alkyl.

A is preferably $C_1$-$C_2$-alkylene and in particular ethylidene.

m is preferably 0.

A particularly preferred embodiment are the compounds of the formula I in which $R^1$ is 4-fluorophenyl, $R^2$ is $C_1$-$C_6$-alkyl or benzyl, where the phenyl group of the benzyl radical may be substituted as indicated above; $R^3$ is the radical of the formula

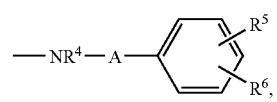

where $R^4$, $R^5$, $R^6$ and A are as defined above, and m is 0.

A further preferred embodiment are compounds of the formula I in which $R^2$ is $C_1$-$C_6$-alkyl, in particular methyl, and $R^1$ is halophenyl or halo-$C_1$-$C_6$-alkylphenyl, in particular 4-fluorophenyl, 2,4-difluorophenyl, 4-trifluoromethylphenyl or 3-trifluoromethylphenyl. $R^3$ is then preferably as defined below:
a) halogen, in particular F or Cl;
b) OH or O $C_1$-$C_6$-alkyl, in particular methoxy and isopropoxy,
c) phenylamino;
phenyl- or naphthyl-$C_1$-$C_4$-alkylamino wherein the phenyl group may be substituted by 1 or 2 halogen, in particular F or Cl, $C_1$-$C_6$-alkoxy or $C_1$-$C_6$-alkyl. The amino group may additionally be substituted by $C_1$-$C_6$-alkyl. Examples of such radicals are benzylamino, 4-methoxybenzylamino, 4-methylbenzylamino, 4-chlorobenzylamino, 3,4-dichlorobenzylamino, 2-phenylethylamino, 1-phenylethylamino, 1-naphth-1-yl-amino 1-naphth-2-ylamino; 1-phenylprop-3-ylamino, 3-phenylpropylamino, 1-(4-isobutylphenyl)ethylamino;

e)

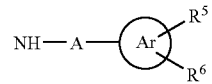

in which A is $C_1$-$C_2$-alkylene, $R^5$ and $R^6$ are H and

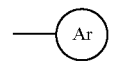

is thienyl, furyl, 2-, 3- or 4-pyridyl, thiazolyl, oxazolyl, benzothiophenyl or benzofuranyl, where the heterocyclic radicals may be substituted by halogen, in particular F or Cl, or $C_1$-$C_6$-alkyl.

f)

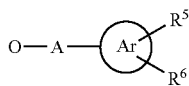

in which A, $R^5$, $R^6$ and

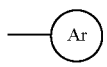

are as defined under e).

g) NH—$C_1$-$C_6$-Alkyl which is substituted by 2 or 3 phenyl groups, for example 3,3-diphenylpropylamino, 1,3-diphenylprop-2-ylamino;

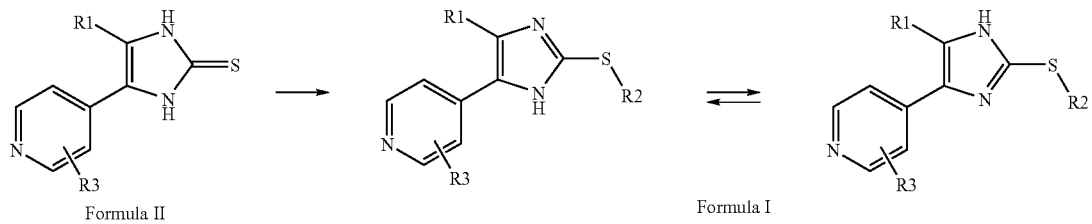

Formula II → Formula I h) NH—A—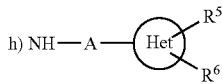

in which A is $C_1$-$C_2$-alkylene, $R^5$ and $R^6$ are H and

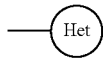

is tetrahydrofuranyl, tetrahydropyranyl, pyrrolidine, N-methyl- or N-ethylpyrrolidine;

i) NH—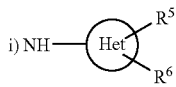

in which $R^5$, $R^6$ and

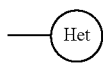

are as defined under h);

j) —NH—COOR$^{10}$, in which $R^{10}$ is $C_3$-$C_6$-cycloalkyl;
k) —NH—CO—NHR$^{10}$, in which $R^{10}$ is $C_3$-$C_6$-cycloalkyl;
l) —NH—COR$^{10}$, in which $R^{10}$ is $C_3$-$C_6$-cycloalkyl-$C_1$-$C_4$-alkyl, for example cyclopentylmethyl, cyclohexylmethyl;
m) NH—CONH CO phenyl;
n) -A-$C_3$-$C_6$-cycloalkyl, in which A is $C_1$-$C_2$-alkylene, for example cyclopentylmethylamino, cyclohexylmethylamino.

The compounds according to the invention can be prepared in a corresponding manner according to the processes described in the state of the art mentioned at the outset, in particular WO 00/17192. The preparation according to the following two-step process has been found to be particularly expedient. In the first step, a substituted imidazole-2-thione of the formula II is initially prepared. In the second step, this is then reacted such that the 2-thio-substituted imidazole derivatives of the formula I are obtained with introduction of the desired substituent $R^2$.

1) Preparation of the imidazole-2-thione

Imidazole-2-thiones where $R^3$=H, halogen (Br, Cl, F), O-alkyl or S-alkyl are prepared according to process A or B. By way of example, process A is illustrated for compounds in which $R^1$ is 4-fluorophenyl and $R^3$ is H, process B is illustrated for compounds in which $R^1$ is 4-fluorophenyl and $R^3$ is Cl, (25a), F (25b) or O-alkyl (25c, 25d) (the numbers in brackets refer to the numbers of the examples). 2-Thio-substituted imidazole derivatives where $R^3$=NR$^4$R$^{10}$ are not prepared from the corresponding imidazole-2-thiones where $R^3$=NR$^4$R$^{10}$ but in a different manner according to process C. 2-Thio-substituted imidazole derivatives where $R^3$=O-alkyl or S-alkyl can be prepared both according to process C and according to process B.

Process A

The synthesis of the substituted imidazole-2-thiones where $R^3$=H is carried out according to the course of the reaction of scheme 1, using ethyl isonicotinate and 4-fluorophenylacetonitrile as starting materials.

The starting materials are converted in a condensation reaction with the aid of metallic sodium in an alcohol, for example ethanol, into 2-cyano-2-(4-fluorophenyl)-1-(4-pyridyl)ethanone (IIIa). The cyano group is then removed by hydrolysis, for example with hydrobromic acid, and decarboxylation, giving 2-(4-fluorophenyl)-1-(4-pyridyl)ethanone (IVa). In the next step, IVa is converted by treatment with ammonium chloride/sodium acetate in an alcoholic solvent, such as methanol, into the oxime (Va). By reaction with p-toluenesulfonyl chloride in pyridine, the latter is converted into the tosylate (VIa). From the tosylate, the thione compound (IIa) is obtained by treatment with sodium ethoxide and reaction of the azirene intermediate formed with potassium thiocyanate.

Scheme 1:
Synthesis of the thiones according to the invention according to process A

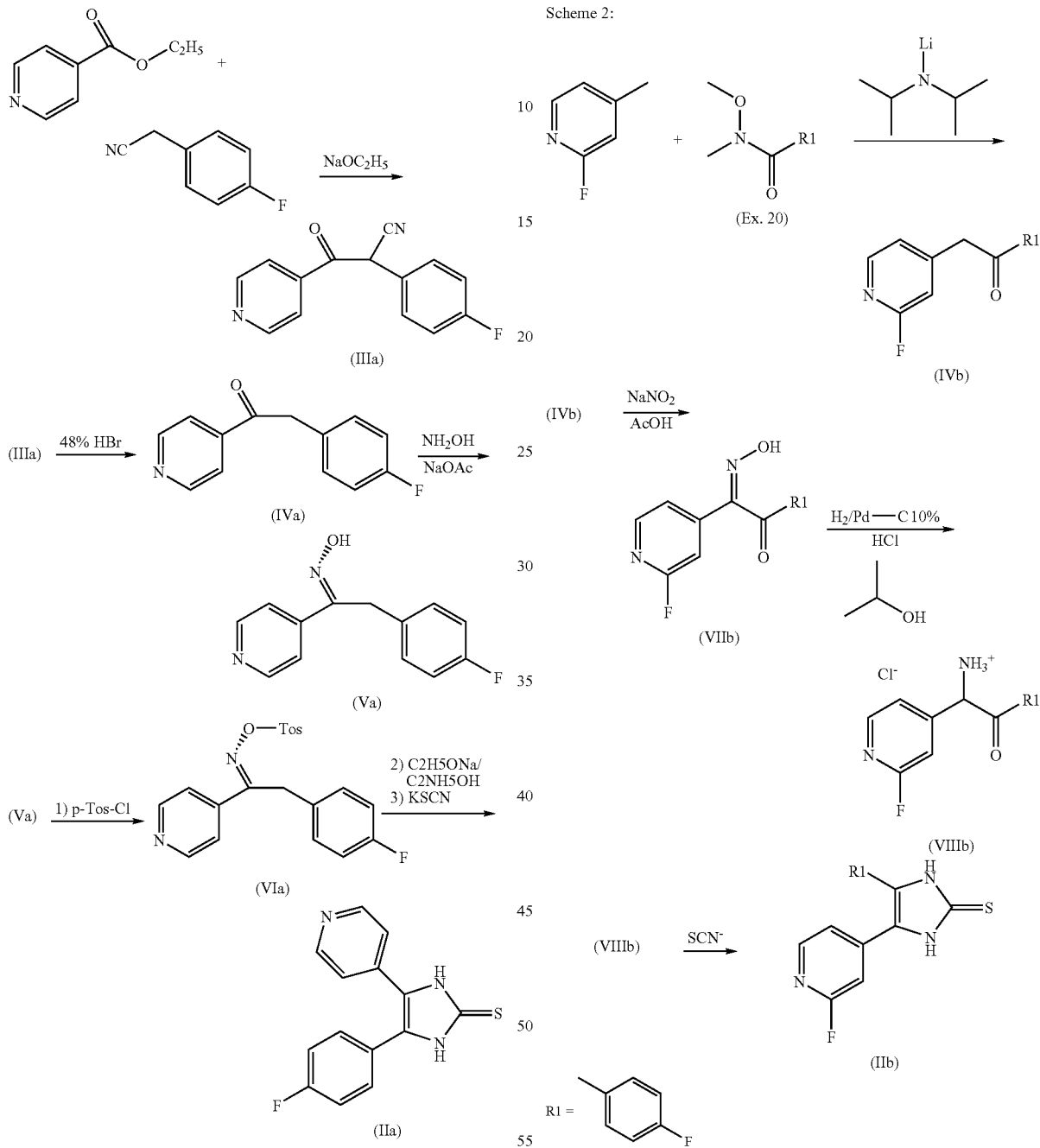

Process B:

The preparation of the compounds according to the invention in which the pyridine radical has a halogen, O-alkyl or S-alkyl substituent is carried out according to scheme 2 via corresponding 2-halopyridyl-substituted imidazolthiones (process B). The preparation of these imidazolthiones is illustrated using the 2-fluoro-substituted pyridinine compound ($R^3$=2-F) where $R^1$=p-fluorophenyl as an example. Imidazolthiones carrying, in position 4, alkyl and cycloalkyl radicals ($R^1$=$C_1$-$C_4$-alkyl, $C_3$-$C_7$-cycloalkyl) are obtained in an analogous manner starting with the appropriately substituted 2-fluoro-γ-picoline ketones.

Scheme 2:

γ-Picoline ($R^3$=H) and the halogen-($R^3$=F, Cl, Br, I), methoxy-($R^3$=$OCH_3$) and methylthio-(24, $R^3$=$SCH_3$) substituted γ-picolines are lithiated in the γ-methyl group with exclusion of moisture, in solvents suitable for this purpose, such as hydrocarbons, ethers and mixtures thereof (for example hexane, tetrahydrofuran, ethylene glycol, dimethyl ether), using lithium diisopropylamide (LDA) and then condensed with suitable carboxylic acid derivatives ($R^1$—COOR, $R^1$—$CONR_2$, $R^1$—CN). Here, the amides of the N,O-dimethylhydroxylamine ($R^1$—$CONCH_3(OCH_3)$, 20) have been found to be particularly suitable. Using nitrites and bases, for example amyl nitrite /sodium methoxide, or using alkali metal nitrite and acid, the γ-picolyl ketones (IVb) formed are nitrosated in the γ-picolyl position. The reaction of the γ-picolyl ketone, dissolved in glacial acetic acid, with aqueous sodium nitrite solution has been found to be particularly advantageous. During this reaction, the nitrosoketones are converted completely into the tautomeric oxime ketones (VIIb).

The oxime ketones are reduced in alcoholic solution in the presence of hydrogen and mineral acids, for example HCl, using palladium-on-carbon, to give the ammonium salts of the amine ketones (VIIIb) (23b).

Alternatively, other oxime ketones can be reduced in alcoholic solution in the presence of mineral acids, for example $H_2SO_4$, using zinc dust, to give the corresponding ammonium ketones (23f).

These ammonium ketone compounds afford, after action of alkali metal thiocyanates, for example potassium thiocyanate in dry dimethylformamide (DMF) with heating under reflux, the imidazolethiones of the formula IIb where $R^3$=F, Cl, Br, O-alkyl or S-alkyl, as yellow solids (24b).

The preparation of the compounds according to the invention in which the pyridine radical has an ether ($R^3$=$OR^{10}$), thioether ($R^3$=$SR^{10}$) or amino substituent ($R^3$=$NR^4R^{10}$) is carried out according to scheme 4 or scheme 5, via corresponding 2-halopyridyl-substituted imidazolethiones (process C, see below).

2) Preparation of the 2-thioimidazole compound

The imidazolethione compounds of the formula II obtained according to process A or B are, by substitution of the sulfur atom in the 2-position, converted into the compounds of the formula I according to the invention. The substitutions, as shown in an exemplary manner for some compounds in scheme 3, are carried out in a known manner using a nucleophilic substitution reaction. Here, the compound IIa or IIb is reacted with $R^2$—X in an inert polar solvent, such as an alcohol. X is an easily exchangeable group, such as Hal, in particular Cl, Br, I, methylsulfonyl, tosyl, etc. Suitable processes are known to the person skilled in the art and described, for example, in WO 00/17192, EP 0 372 445 and U.S. Pat. No. 4,440,776. The compounds $R^2$—X are known or can be prepared by known processes as described, for example, in WO 00/17192.

Scheme 3:

3. Substitution of the sulfur by alkyl halides and arylalkyl halides or alcohol sulfonates.

3.1.

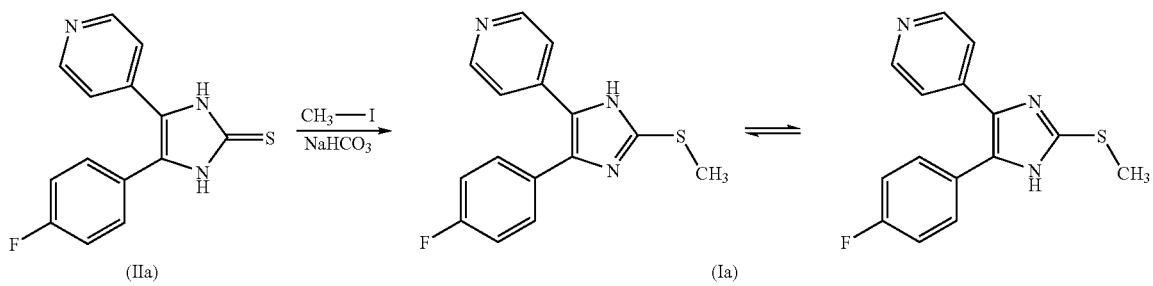

(IIa)         (Ia)

3.2.

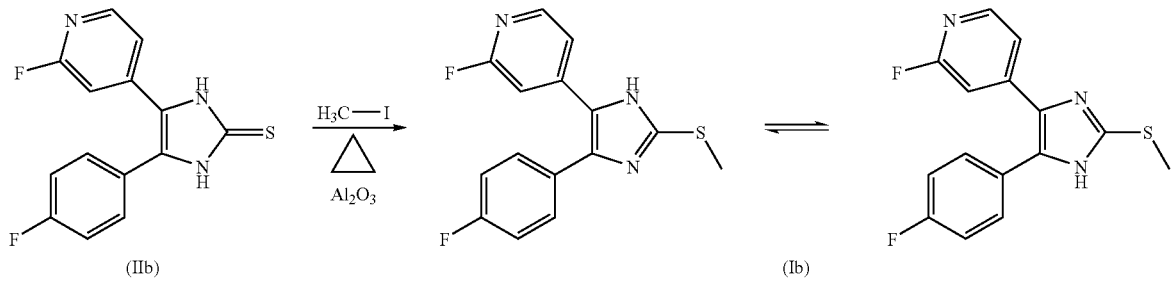

(IIb)         (Ib)

Process C:

Compounds according to the invention in which $R^3$ is an amino substituent ($R^3$=$NR^4R^{10}$) are prepared from 2-thioimidazoles using 4(5)-(2-halopyridin-4-yl) substitution. The process (process C) is illustrated in scheme 4 using the 2-benzylamino ($R^3$=NH—$CH_2Ph$) where $R^1$=p-fluorophenyl as an example (25f).

The starting materials (Ib) can be prepared by the process described above.

Scheme 4:

4.1. 4-(2-Aminopyridin-4-yl)-substituted 2-thioimidazoles

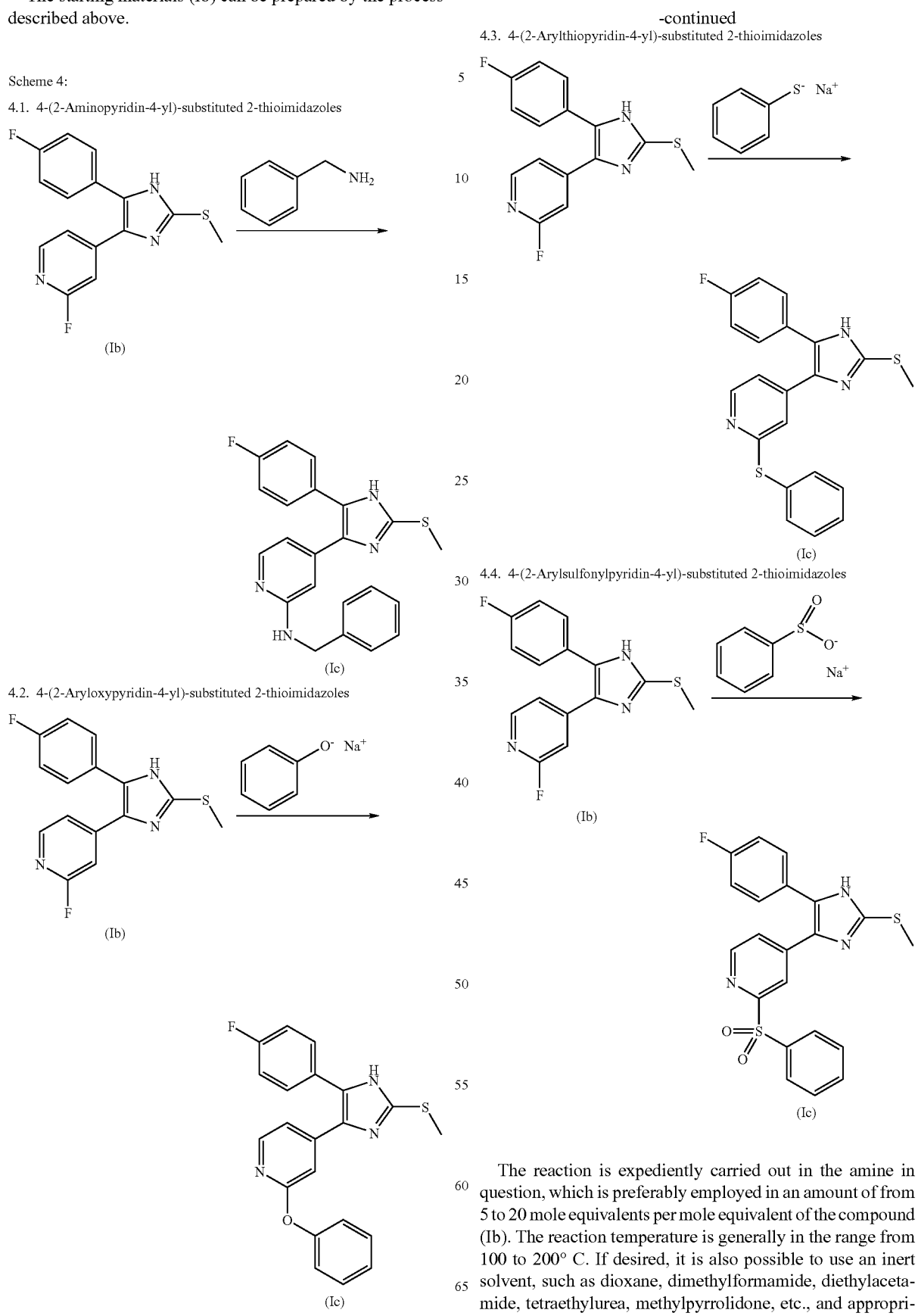

4.2. 4-(2-Aryloxypyridin-4-yl)-substituted 2-thioimidazoles 4.3. 4-(2-Arylthiopyridin-4-yl)-substituted 2-thioimidazoles 4.4. 4-(2-Arylsulfonylpyridin-4-yl)-substituted 2-thioimidazoles The reaction is expediently carried out in the amine in question, which is preferably employed in an amount of from 5 to 20 mole equivalents per mole equivalent of the compound (Ib). The reaction temperature is generally in the range from 100 to 200° C. If desired, it is also possible to use an inert solvent, such as dioxane, dimethylformamide, diethylacetamide, tetraethylurea, methylpyrrolidone, etc., and appropriate additives, such as alkali metal carbonates or monovalent copper halides (to neutralize acid equivalents released or to catalyze the elimination of halogen).

The compounds according to the invention in which $R^3$ is an alkoxy substituent or alkylthio substituent ($R^3$=O—$C_1$-$C_6$-alkyl, S—$C_1$-$C_6$-alkyl) can not only be prepared by process B (starting with appropriately substituted picolines) but also by process C, starting with the 4(5)-(2-halopyridin-4-yl)-substituted 2-thioimidazoles.

Process D:

The compounds according to the invention in which $R^3$ is an alkoxy substituent ($R^3$=O—$C_1$-$C_6$-alkyl) can not only be prepared by process B or C, but also by process D, starting with the 4(5)-(2-halopyridin-4-yl)-substituted 2-thioimidazoles. The process is illustrated in scheme 5, using the 2-isopropyloxypyridinine compounds ($R^3$=OCH(CH$_3$)$_2$) where $R^1$=p-fluorophenyl as an example.

The starting materials (Ib) can be prepared by the processes described above.

Scheme 5:
4-(2-Alkoxypyridin-4-yl)-substituted 2-thioimidazoles

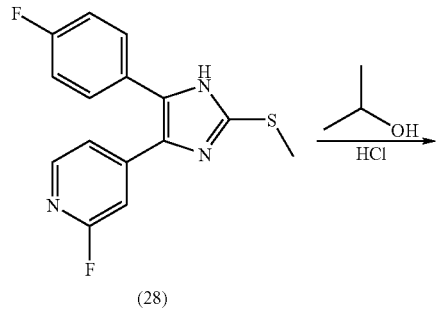

The reaction is expediently carried out in the alcohol, which is preferably used in an amount of from 5 to 20 mole equivalents per mole equivalent of the compound (Ib), in the case of lower alcohols also up to one hundred mole equivalents, in the presence of a strong acid, such as HCl or trifluoroacetic acid, methanesulfonic acid, etc. The reaction temperature is generally within the boiling range of the lower alcohols, in the case of higher alcohols in the range from 100 to 200° C. It has been found to be favorable, for example, to saturate the alcohol with gaseous HCl, or to re-saturate during the reaction.

Alternatively, the exchange of fluorine for alkoxy in the 2-position of the pyridyl substituent can be carried out at an earlier stage in the synthesis, for example at the stage of the oxime ketones or the amine ketones. In these cases, the reactions proceed under conditions comparable to those just described for intermediate Ib (22c).

Processes E, F and G:

The compounds according to the invention in which $R^3$ is an amido substituent ($R^3$=NR$^7$COR$^{10}$) are, firstly, prepared from the 4(5)-(2-halopyridin-4-yl)-substituted 2-thioimidazoles. The process (process E) is illustrated in scheme 6.1 using the 2-benzoylamido ($R^3$=NH—COPh) where $R^1$=p-fluorophenyl as an example. Secondly, after the hydrolysis of the amides to the amine-substituted ($R^3$=NR$^7$H, NHR$^{10}$) 2-thioimidazoles and their re-acylation or derivatization to amides, ureas and urethanes, further amido substituents may be obtained (process F). This is illustrated in scheme 6.2. Thirdly, 2-aminopyridine precursor compounds may be obtained from 4(5)-(2-halopyridin-4-yl) compounds via the 4(5)-(2-azidopyridin-4-yl) compounds (process G). In this variant, the halogen is substituted nucleophilically by an alkali metal azide, and the azide group is then converted by reduction methods into the amino group, see scheme 6.3.

Process H:

This interesting variant also allows access to alkylated amines from aldehyde and ketone precursors. If the conversion of the azide group into the amino group is carried out under hydrogenation conditions using a hydrogenation catalyst in the presence of these aldehydes and ketones, alkylated amines where $R^3$=NHCH$_2$—B or NHCH(alkyl)-B are obtained (process H, scheme 6.4). The same result is obtained when the azide is cleaved with a phosphine to give the phosphimide, and these imides obtained after an aza-Wittig reaction with an aldehyde (or ketone) are reduced to the amines using complex hydrides (process H, scheme 6.5).

The starting materials (Ib) can be prepared by the processes described above.

Scheme 6:
6.1: 4-(2-Amidopyridin-4-yl)-substituted 2-thioimidazoles

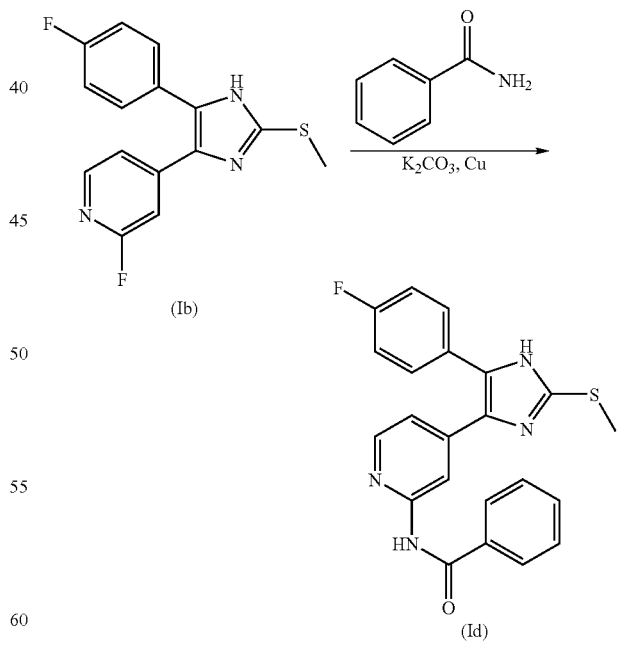

The reaction is expediently carried out in the amide in question, which is preferably employed in an amount of from 5 to 20 mole equivalents per mole equivalent of the compound (Ib). The reaction temperature is generally in the range from 100 to 200° C. If desired, it is also possible to use an inert solvent, such as dioxane, dimethylformamide, diethylacetamide, tetraethylurea, methylpyrrolidone, etc., and appropriate additives, such as alkali metal carbonates or monovalent copper halides (to neutralize acid equivalents released or to catalyze the elimination of halogen).

The 2-aminopyridine compounds can be obtained from 2-amidoacylpyridines by hydrolysis (6.2) or else by azide substitution of the 2-fluoro compounds and subsequent reduction of the 2-azidopyridines (6.3), for example by hydrogenation on palladium-on-carbon in alcoholic solvents.

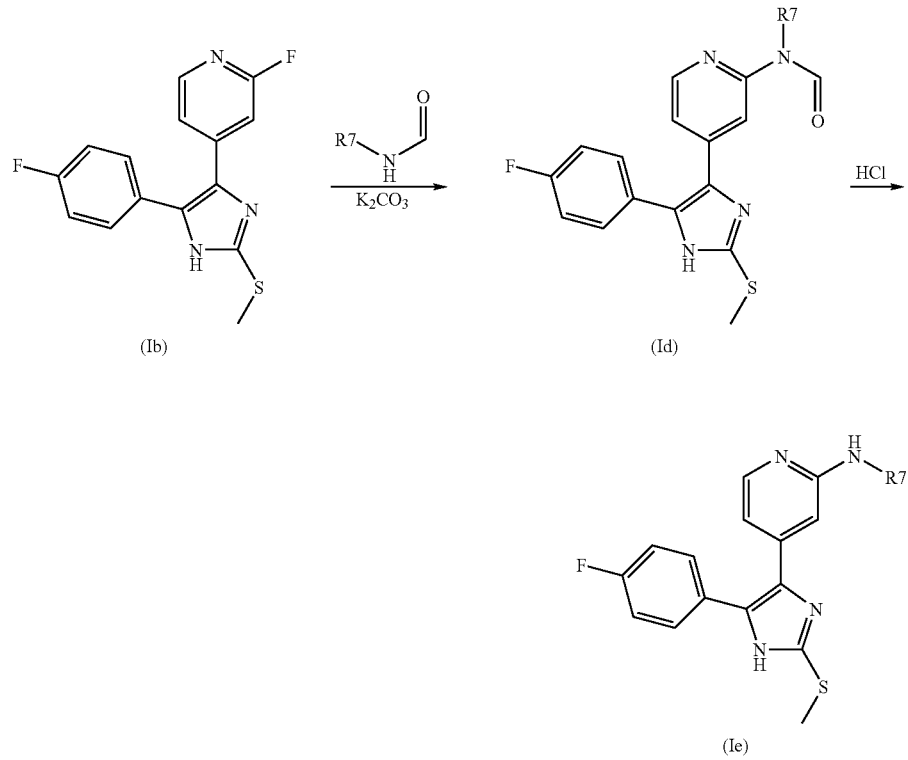

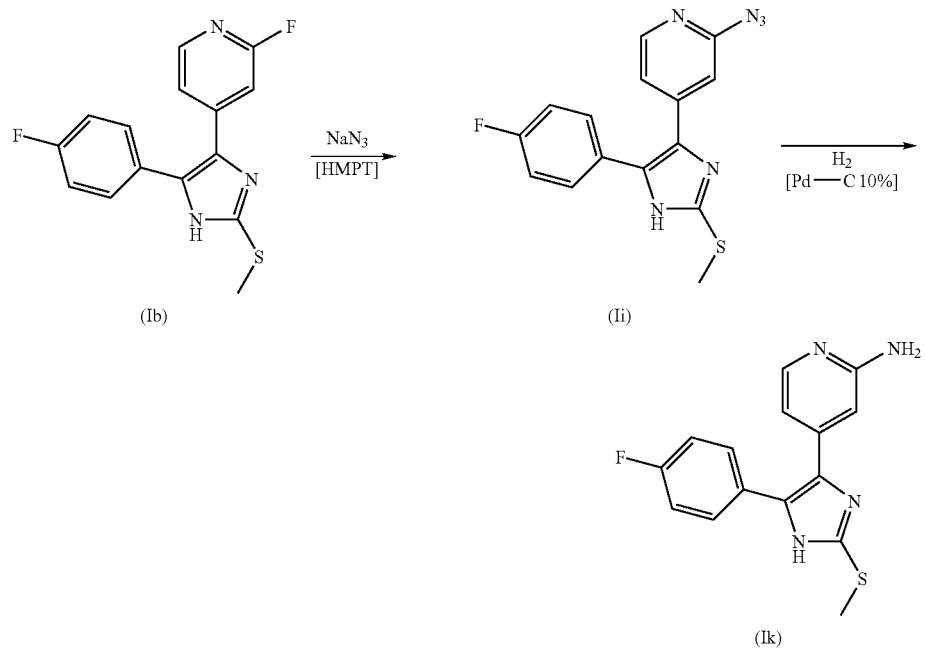

-continued
6.4
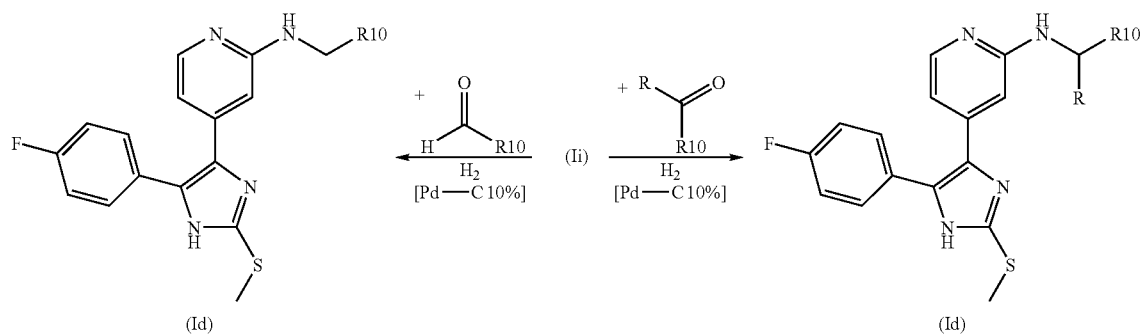
6.5
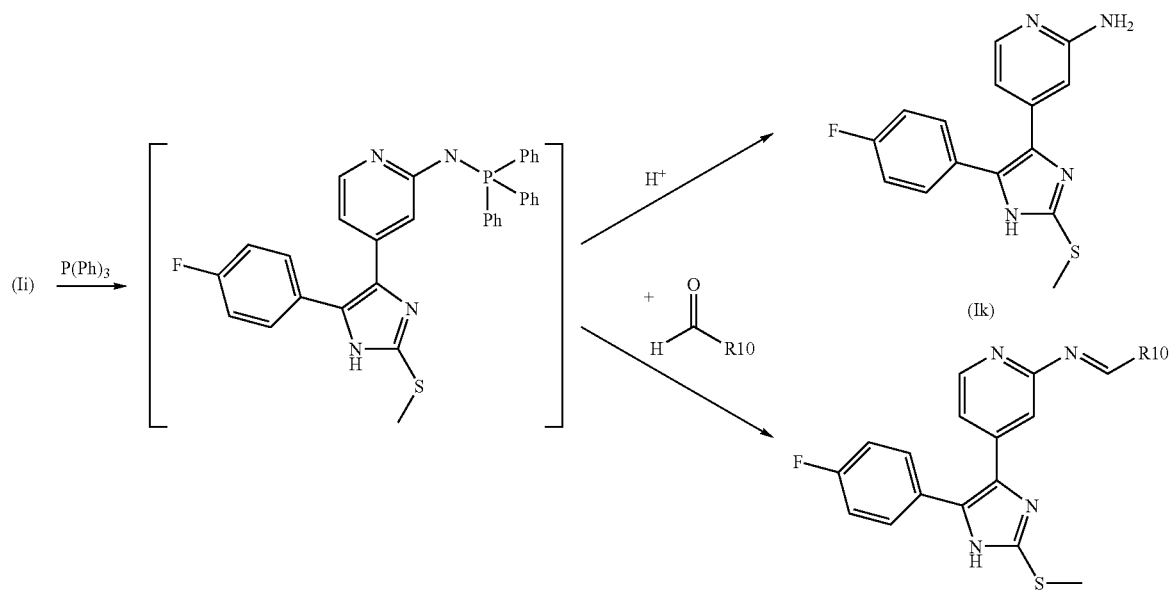
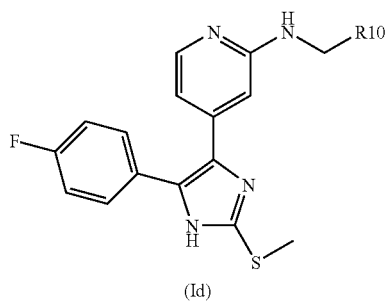

Further conversions of the amines obtained (Ik, Id) by derivatization are possible (process F). What is used are reactions of the amines Id and Ik both with acid anhydrides and acid chlorides to give further amides, and also reactions with chloroformic esters to give urethanes, with isocyanates to give ureas and with acyl isocyanates to give acylureas. These formations of derivatives are illustrated in scheme 7.

ischemia, congestive heart failure, pulmonary fibrosis, hepatitis, glioblastoma, Guillain-Barre syndrome, systemic lupus erythematodes, adult respiratory distress syndrome (ARDS) and respiratory distress syndrome.

The compounds according to the invention can be administered either as individual therapeutically active compounds or as mixtures with other therapeutically active compounds.

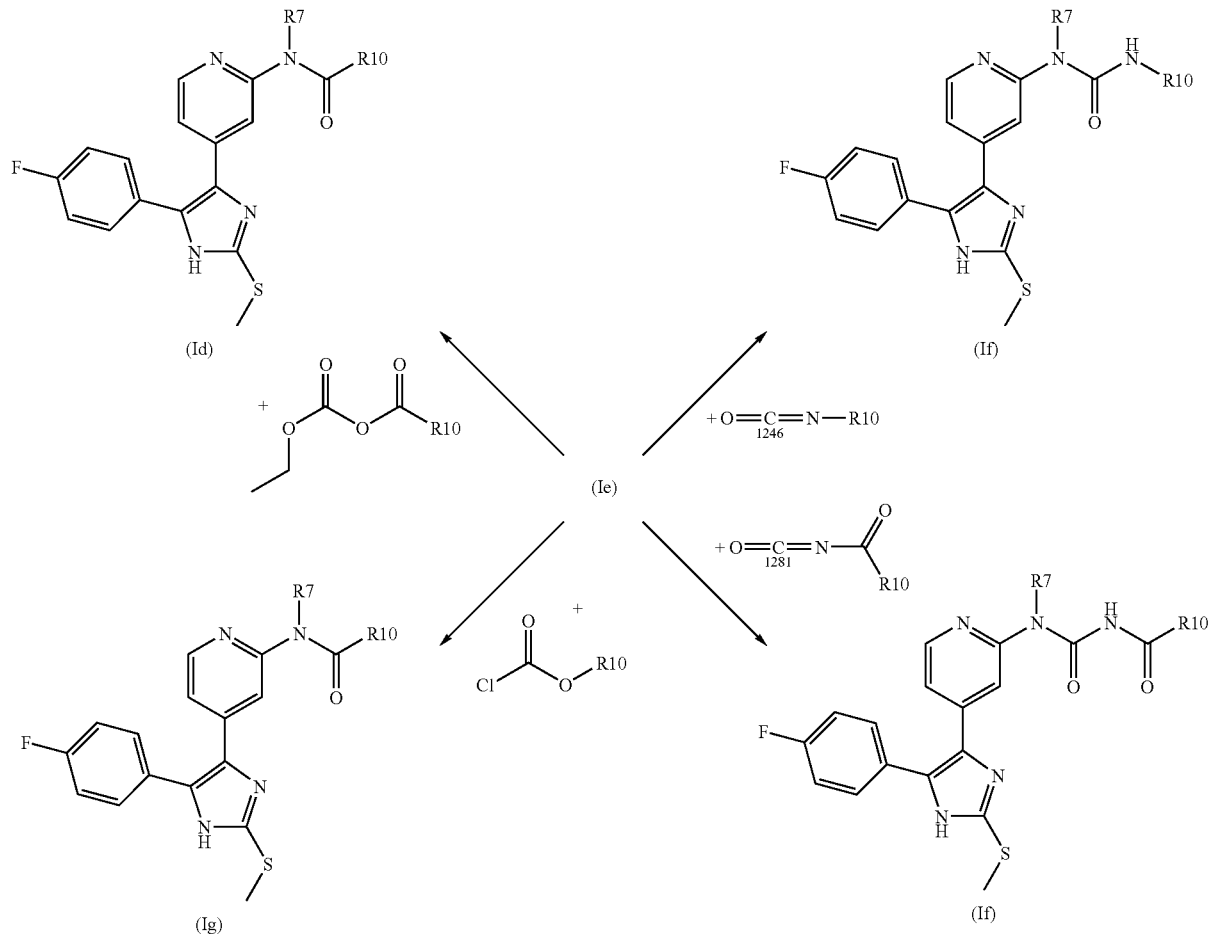

Scheme 7
Conversion of the amines (Ik, Id) into amides, urethanes and ureas

In vitro and in vivo, the compounds according to the invention show immunomodulating and cytokine-release inhibiting action. Cytokines are proteins such as TNF-α and IL-β which play an important role in numerous inflammatory disorders. The compounds according to the invention are, by virtue of their cytokine-release-inhibiting action, suitable for treating disorders which are associated with a disturbance of the immune system. They are suitable, for example, for treating autoimmune disorders, cancer, rheumatoid arthritis, gout, septic shock, osteoporosis, neuropathic pain, the spread of HIV, HIV dementia, viral myocarditis, insulin-dependent diabetes, periodontal disorders, restenosis, alopecia, T-cell depletion associated with HIV infections or AIDS, psoriasis, acute pancreatitis, rejection reactions of allogenic transplants, allergic pneumonia, arteriosclerosis, multiple sclerosis, cachexia, Alzheimer's disease, stroke, ictus, colitis ulcerosa, morbus Crohn, inflammatory bowel disease (IBD), The compounds can be administered on their own; in general, however, they are formulated and administered in the form of pharmaceutical compositions, i.e. as mixtures of the active compounds with suitable pharmaceutical carriers or diluents. The compounds or compositions can be administered orally or parenterally; preferably, they are administered in oral dosage forms.

The type of pharmaceutical composition or carrier or diluent depends on the desired administration form. Oral compositions, for example, can be present as tablets or capsules and may comprise customary excipients, such as binders (for example syrup, gum arabic, gelatin, sorbitol, tragacanth or polyvinylpyrrolidone), fillers (for example lactose, sugar, cornstarch, calcium phosphate, sorbitol or glycerol), glidants (for example magnesium stearate, talc, polyethylene glycol or silica), disintegrants (for example starch) or wetting agents (for example sodium lauryl sulfate). Liquid oral preparations can assume the form of aqueous or oily suspensions, solutions, emulsions, syrups, elixirs or sprays and the like. They can also be present as a dry powder which is reconstituted using water or another suitable carrier. Such liquid preparations may comprise customary additives, for example suspending agents, flavors, diluents or emulsifiers. For parenteral administration, it is possible to use solutions or suspensions with customary pharmaceutical carriers.

The compounds or compositions according to the invention can be administered to mammals (man or animal) in a dose of from about 0.5 mg to 100 mg per kg of body weight per day. They may be administered in one individual dose or in a plurality of doses. The activity spectrum of the compounds as inhibitors of cytokine release was examined using the test systems below, as described by C. Donat and S. Laufer in Arch. Pharm. Pharm. Med. Chem. 333, Suppl. 1, 1-40. 2000.

In Vitro Test with Human Whole Blood

The test substance is added to samples of human potassium-EDTA whole blood (of 400 µl each) and the samples are preincubated in a $CO_2$ incubator (5% $CO_2$; 95% moisture-saturated air) at 37° C. for 15 min. The samples are then stimulated with 1 µg/ml of LPS (*E. coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 1000 g for 15 min. The amount of IL-1β and TNFα in the plasma supernatant is then determined by ELISA.

In Vitro Test with PBMCs

1) The mononuclear cells (PBMCS) from human potassium-EDTA whole blood, diluted 1:3, are isolated by density gradient centrifugation (Histopaque®-1.077). The cells are washed twice with DPBS buffer, resuspended in macrophage SFM medium and adjusted to a cell count of $1\times10^6$ cells/ml.

The resulting PBMCs suspension (samples of in each case 390 µl) and the test substance are preincubated at 37° C. in a $CO_2$ incubator (5% $CO_2$; 95% moisture-saturated air) for 15 min. The samples are then stimulated with in each case 1 µl/ml of LPS (*E. coli* 026:B6) at 37° C. in a $CO_2$ incubator (5% $CO_2$; 95% moisture-saturated air) for 4 hours. The reaction is stopped by placing the samples on ice, adding DPBS buffer and then centrifuging at 15 880 g for 12 min. The amount of IL-1β and TNFα in the plasma supernatant is then determined by ELISA.

2) Kinase Assay

At 37° C., microtiter plates were coated for one hour with 50 µl of ATF2 solution (20 µg/ml). The plates were washed three times with water, and 50 µl of kinase mixture (50 mM tris-HCl, 10 mM $MgCl_2$, 10 mM β-glycerol phosphate, 10 µg/ml of BSA, 1 mM DTT, 100 µM ATP, 100 µM $Na_3VO_4$, 10 ng of activated p38a) with or without inhibitor were added into the wells, and the plates were incubated at 37° C. for 1 hour. The plates were washed three times and then incubated with phosphorus-ATF-2 antibody for one hour. The plates were once more washed three times, and goat-antirabbit IgG labeled with alkaline phosphatase was added at 37° C. for one hour (to fix antibody-phosphorylated protein/substrate complex). The plates were washed three times, and the alkaline phosphatase/substrate solution (3 mM 4-NPP, 50 mM $NaHCO_3$, 50 mM $MgCl_2$, 100 µl/well) was added at 37° C. for 1.5 hours. Formation of 4-nitrophenolate was measured at 405 nm using a microtiter plate reader. The $IC_{50}$ values were calculated.

The results of the in vitro tests are shown in table 1 below.

TABLE 1

| | Test results | | | | |
|---|---|---|---|---|---|
| Compound No. | $IC_{50}$ (µM) p 38 | $IC_{50}$ (µM) TNF-α | PBMCA IL-1β | $K_{50}$ (µM) TNF-α | Whole blood IL-1β |
| 25a | | 2.2 | 0.35 | | |
| 25b | 3.8 | 2.8 | 0.30 | | |
| 25c | 8.7 | 4.6 | 2.7 | 7.2 | 2.2 |
| 25d | | 1.9 | 0.15 | | |
| 25e | | 3.1 | 0.50 | | |
| 25f | 0.65 | 0.63 | 0.108 | | |
| 25g | 0.79 | 0.64 | 0.056 | | |
| 25h | 0.83 | 0.67 | 0.085 | 17.3 | 22.3 |
| 25i | 0.95 | 0.50 | 0.15 | 14.8 | 13.3 |
| 25j | 0.70 | 0.72 | 0.23 | | |
| 25k | 0.13 | 0.34 | 0.030 | | |
| 25l | 0.24 | 0.35 | 0.031 | 14.9 | 17.1 |
| 25m | 0.38 | 0.16 | 0.039 | 2.7 | 0.99 |
| 25n | 0.34 | 0.17 | 0.041 | | |
| 25o | 0.90 | 0.37 | 0.044 | | |
| 26a | | 60.0 | 1.8 | | |
| 26b | 4.2 | 40.5 | 2.9 | | |
| 26c | 1.42 | 3.2 | 0.20 | | |
| 26d | 0.38 | 2.7 | 0.045 | | |
| 26e | | 21.0 | 0.18 | | |
| 27a | | 12.0 | 2.1 | | |
| 27b | 9.3 | 6.9 | 2.45 | | |
| 27c | 1.45 | 2.0 | 0.47 | | |
| 27d | 0.27 | 0.91 | 0.040 | 10.0 | 15.7 |

The examples below illustrate the invention, without limiting it.

EXAMPLE 1 a) 4-(4-Fluorophenyl)-5-pyridin-4-yl-1,3-dihydroimidazole-2-thione 2-(4-Fluorophenyl)-3-hydroxy-3-pyridin-4-ylacrylonitrile (a1)

A mixture of ethyl isonicotinate (75.8 g; 0.5 mol) and 4-fluorophenylacetonitrile (67.6 g; 0.5 mol) was added dropwise to a solution of metallic sodium (17.3 g; 0.7 mol) in absolute ethanol (250 ml). The reaction mixture was stirred at 100° C. for 15 min. The reaction mixture was then cooled in an ice bath, and 600 ml of distilled $H_2O$ were added. When the mixture was acidified with concentrated HCl (90 ml), the hydrochloride of a1 was obtained as yellow precipitate at pH 1. The precipitate was filtered off, washed with $H_2O$ and dried under reduced pressure over $P_2O_5$. M.p. 226° C.

2-(4-Fluorophenyl)-1-pyridin-4-ylethanone (a2)

A solution of a1 (40.6 g; 0.15 mol) in 48% strength hydrobromic acid (130 ml) was stirred under reflux for 19 h. The mixture was cooled in an ice bath, and the precipitate obtained (4-fluorophenylacetic acid) was filtered off and washed with $H_2O$. When the filtrate was neutralized with ammonia water (80 ml) a2 was obtained as a dark-green precipitate which was filtered off, washed with $H_2O$ and dried under reduced pressure over $P_2O_5$: light-gray/beige powder. M.p. 215° C.

2-(4-Fluorophenyl)-1-pyridin-4-ylethanone oxime (a3)

Sodium acetate (36.1 g; 0.44 mol) and hydroxylamine hydrochloride (22.0 g; 0.32 mol) were introduced into a suspension of a2 (21.5 g; 0.1 mol) in 50% strength methanol (350 ml). The reaction mixture was stirred under reflux for 1 h. When the clear solution was cooled in an ice bath, a3 was obtained as a beige precipitate which was filtered off, washed with $H_2O$ and dried under reduced pressure over $P_2O_5$. M.p. 155° C.

2-(4-Fluorophenyl)-1-pyridin-4-ylethanone, O-[(4-methylphenyl)sulfonyl]oxime (a4)

Under an atmosphere of argon, a3 (10.1 g; 0.04 mol) was dissolved in absolute pyridine (50 ml). The solution was cooled to 6° C., and toluenesulfonyl chloride (10.1 g; 0.05 mol) was added a little at a time. After the addition had ended, the reaction mixture was stirred at room temperature for 20 h. The mixture was then poured into 500 ml of ice-water. The precipitate (a4) was filtered off, washed with cold $H_2O$ and dried in a drying cabinet at 50° C. M.p. 201° C.

4-(4-Fluorophenyl)-5-pyridin-4-yl-1,3-dihydroimidazole-2-thione (1a)

Under an atmosphere of argon, a solution of a4 (10.0 g; 0.03 mol) in absolute ethanol (56 ml) was cooled to 5° C., and a freshly prepared solution of metallic sodium (0.75 g; 0.03 mol) in absolute ethanol (30 ml) was added dropwise. The reaction mixture was stirred at 5° C. for 5 h. After addition of diethyl ether (500 ml), stirring was continued for 30 min. The precipitate (TosOH) was filtered off and washed with diethyl ether (4×50 ml). The combined ethereal phase was extracted with 10% strength hydrochloric acid (3×90 ml). The aqueous extract was concentrated to a volume of about 40 ml, and potassium thiocyanate (5.0 g; 0.05 mol) was added. The reaction mixture was stirred under reflux for 1 h. When the mixture was neutralized with 5% strength sodium bicarbonate solution (270 ml), a5 was obtained as a beige precipitate which was filtered off, washed with $H_2O$ and dried in a drying cabinet at 60° C. Yield 5.6 g (79%); m.p. 382° C.

$^1$H-NMR (DMSO-$d_6$): δ (ppm) 7.1 (m, 2H, 4-F-Ph), 7.3 (m, 2H, 4-Pyr), 7.5 (m, 2H, 4-F-Ph), 8.5 (m, 2H, 4-Pyr), 12.7 (d, 2H, exchangeable, NH)

The following compounds were obtained in a corresponding manner:

1b: 3-(4-fluorophenyl)-5-pyridin-4-yl-1,3-dihydroimidazole-2-thione
1c: 4-(4-chlorophenyl)-5-pyridin-4-yl-1,3-dihydroimidazole-2-thione
1d: 4-(4-bromophenyl)-5-pyridin-4-yl-1,3-dihydroimidazole-2-thione
1e: 4-phenyl-5-pyridin-4-yl-1,3-dihydroimidazole-2-thione

EXAMPLE 2

1-Chloromethyl-4-methylsulfanylbenzene (2)

4-Methylsulfanylbenzyl alcohol (30.5 g; 0.2 mol) was dissolved in dichloromethane (180 ml). A solution of thionyl chloride (23.8 g; 0.2 mol) in dichloromethane (120 ml) was added dropwise to the initial charge, which was kept under reflux. The reaction mixture was stirred under reflux for a further 2 h. The solution was cooled to room temperature, washed with $H_2O$ (2×250 ml), dried over $Na_2SO_4$ and concentrated. The oily residue (6) was purified by column chromatography ($Al_2O_3$, $CH_2Cl_2$).

$^1$H-NMR (CDCl$_3$): δ (ppm) 2.46 (s, 3H, CH$_3$), 4.5 (s, 2H, CH$_2$), 7.2-7.3 (q, 4H, 4-MeS-Ph)

EXAMPLE 3

1-Chloromethyl-4-methanesulfinylbenzene (3)

A solution of 2 (17.3 g; 0.1 mol) in glacial acetic acid (150 ml) was cooled to 10° C. A solution of $H_2O_2$ (35% strength solution; 13.1 g; 0.13 mol) in glacial acetic acid (50 ml) was added dropwise to the initial charge. The reaction mixture was stirred at room temperature for 2 h. The mixture was cooled in an ice bath, ice (200 g) was added and the mixture was neutralized with ammonia water (290 ml). The aqueous phase was extracted with ethyl acetate (2×300 ml). The organic phase was washed with $H_2O$ (2×300 ml), dried over $Na_2SO_4$ and concentrated. By scratching and cooling the oily residue, 3 was obtained in crystalline form.

$^1$H-NMR (CDCl$_3$): δ (ppm) 2.73 (s, 3H, CH$_3$), 4.6 (s, 2H, CH$_2$), 7.5 (d, 2H, 4-MeS(O)-Ph), 7.6 (d, 2H, 4-MeS(O)-Ph)

EXAMPLE 4

1-Chloromethyl-4-methanesulfonylbenzene (4)

m-Chloroperbenzoic acid (70%; 8.6 g; 0.04 mol) was introduced into a solution of 3 (3.0 g; 0.02 mol) in chloroform (50 ml). The reaction mixture was stirred under reflux for 4 h. The mixture was cooled to room temperature and filtered. The filtrate was washed with saturated NaHCO$_3$ solution (2×) and dried over Na$_2$SO$_4$. After concentration of the organic phase, 8 remained as a crystalline white solid. M.p. 102° C.

$^1$H-NMR (CDCl$_3$): δ (ppm) 3.07 (s, 3H, CH$_3$), 4.6 (s, 2H, CH$_2$), 7.6 (d, 2H, 4-MeSO$_2$-Ph), 7.9 (d, 2H, 4-MeSO$_2$-Ph)

EXAMPLE 5

Methyl 5-chlorosulfonyl-2-hydroxybenzoate (5a)

5a was prepared from methyl salicylate (10.0 g; 65.7 mmol) using the method described in the synthesis of 5c.

$^1$H-NMR (CDCl$_3$): δ (ppm) 4.05 (s, 3H, CH$_3$), 7.18 (d, 1H, 8.9 Hz, C$^3$—H), 8.09 (dd, 1H, 2.5/9.0 Hz, C$^4$—H), 8.57 (d, 1H, 2.5 Hz, C$^6$—H), 11.55 (s, 1H, exchangeable, phenol-OH)

Methyl 5-chloro-3-chlorosulfonyl-2-hydroxybenzoate (5b)

5b was prepared from methyl 5-chlorosalicylate (16.0 g; 85.7 mmol) using the method described in the synthesis of 5c.

$^1$H-NMR (CDCl$_3$): δ (ppm) 4.06 (s, 3H, CH$_3$), 8.11 (d, 1H, 2.7 Hz, C$^6$—H), 8.19 (d, 1H, 2.7 Hz, C$^4$—H), 12.09 (s, 1H, exchangeable, phenol-OH)

Ethyl 3-chlorosulfanyl-4-methoxybenzoate (5c)

A solution of ethyl 4-methoxybenzoate (15.7 g; 87.2 mmol) in CCl$_4$ (60 ml) was cooled to −15° C., and chlorosulfonic acid (17.5 ml; 263 mmol) was added dropwise over a period of 15 min, resulting in a temperature increase to −10° C. After the addition had ended, the reaction mixture was stirred at room temperature for 2 h and then heated at 50° C. until no more starting material could be detected by thin-layer chromatography. With ice-cooling and vigorous stirring, the reaction mixture was added to a suspension of ice (50 g) in CCl$_4$ (100 ml). The mixture was stirred vigorously for 3 min. The organic phase was separated off and the aqueous phase was extracted with CH$_2$Cl$_2$ (3×100 ml). The combined organic extracts were washed with saturated NaCl solution (3×), dried over Na$_2$SO$_4$ and concentrated. Trituration of the oily brown residue with diethyl ether resulted in 5c precipitating as a crystalline white solid.

$^1$H-NMR (CDCl$_3$): δ (ppm) 1.41 (t, 3H, 7.1 Hz, CH$_3$), 4.14 (s, 3H, CH$_3$), 4.42 (q, 2H, 7.1 Hz, CH$_2$), 7.18 (d, 1H, 8.8 Hz, C$^5$—H), 8.37 (dd, 1H, 2.1/8.8 Hz, C$^6$—H), 8.63 (d, 1H, 2.1 Hz, C$^2$—H)

EXAMPLE 6

2-Hydroxy-5-mercaptobenzoic acid (6a)

6a was prepared from 5a (0.50 g; 2.0 mmol) using the method described in the synthesis of 7c, without alkylation with dimethyl sulfate $^1$H-NMR (DMSO-d$_6$): δ (ppm) 5.39 (bs, 1H, exchangeable, carboxyl-OH), 6.90 (d, 1H, 8.7 Hz, C$^3$—H), 7.45 (dd, 1H, 2.5/8.6 Hz, C$^4$—H), 7.75 (d, 1H, 2.5 Hz, C$^6$—H), phenol-OH not visible

EXAMPLE 7

2-Hydroxy-5-methylsulfanylbenzoic acid (7a)

7a was prepared from 5a (10.0 g; 40.0 mmol) using the method described in the synthesis of 7c.

$^1$H-NMR (CDCl$_3$): δ (ppm) 2.48 (s, 3H, CH$_3$), 6.97 (d, 1 H, 8.7 Hz, C$^3$—H), 7.51 (dd, 1H, 2.5/8.7 Hz, C$^4$—H), 6.97 (d, 1H, 8.7 Hz, C$^3$—H), 7.87 (d, 1H, 2.4 Hz, C$^6$—H), 10.26 (bs, 1H, phenol-OH), CO$_2$H not visible 5-Chloro-2-hydroxy-3-methylsulfanylbenzoic acid (7b)

7b was prepared from 5b (13.0 g; 45.6 mmol) using the method described in the synthesis of 7c.

$^1$H-NMR (DMSO-d$_6$): δ (ppm) 2.47 (s, 3H, CH$_3$), 7.33 (d, 1H, 2.4 Hz, C$^6$—H), 7.52 (d, 1H, 2.4 Hz, C$^4$—H), phenol-OH and CO$_2$H not visible 4-Methoxy-3-methylsulfanylbenzoic acid (7c)

Triphenylphosphine (20.5 g; 78.2 mmol) was introduced a little at a time into a solution of 5c (5.1 g; 18.3 mmol) in toluene (50 ml). The reaction mixture was stirred at room temperature for 4.5 h. The precipitate (triphenylphosphine oxide) was filtered off, and the yellow filtrate was extracted with 10% strength aqueous sodium hydroxide solution (4×). Dimethyl sulfate (2 ml) was added to the combined aqueous extract, and the reaction mixture was stirred at room temperature for 2 h. The precipitate obtained was dissolved by heating to reflux temperature. The clear solution was cooled and adjusted to pH 1 using 20% strength hydrochloric acid. The precipitate (7c) was filtered off, washed with H$_2$O and dried under reduced pressure over CaCl$_2$.

$^1$H-NMR (CD$_3$OD): δ (ppm) 2.43 (s, 3H, S—CH$_3$), 3.93 (s, 3H, O—CH$_3$), 6.98 (d, 1H, 8.4 Hz, C$^5$—H), 7.79-7.86 (m, 2H, C$^2$—/C$^6$—H)

4-Hydroxy-3-methylsulfanylbenzoic acid (7d)

A suspension of 7c (0.5 g; 2.5 mmol) in glacial acetic acid/48% strength hydrobromic acid (1+1, 7 ml) was stirred under reflux for 6 h. The reaction mixture was cooled, added to H$_2$O (20 ml) and adjusted to pH 2 using 10% strength Na$_2$CO$_3$ solution. The aqueous solution was extracted with diethyl ether (4×20 ml). The combined organic extract was washed with saturated NaCl solution (2×), dried over Na$_2$SO$_4$ and concentrated. On standing at room temperature, the off-brown oily residue (7d) crystallized out. The crystals were triturated with H$_2$O, filtered off and dried.

$^1$H-NMR (CDCl$_3$): δ (ppm) 2.38 (s, 3H, CH$_3$), 7.05 (d, 1 H, 8.5 Hz, C$^5$—H), 8.02 (dd, 1H, 2.2/8.5 Hz, C$^6$—H), 8.29 (d, 1H, 2.2 Hz, C$^2$—H), phenol-OH and CO$_2$H not visible

EXAMPLE 8

2-Hydroxymethyl-4-methylsulfanylphenol (8a)

8a was prepared from 7a (1.5 g; 8.1 mmol) using the method described in the synthesis of 8c.

$^1$H-NMR (CDCl$_3$): δ (ppm) 2.42 (s, 3H, CH$_3$), 4.79 (s, 2H, CH$_2$), 6.81 (d, 1H, 8.4 Hz, C$^6$—H), 7.01 (d, 1H, 2.1 Hz, C$^3$—H), 7.17 (dd, 1H, 2.3/8.4 Hz, C$^3$—H), OH not visible 4-Chloro-2-hydroxymethyl-6-methylsulfanylphenol (8b)

8b was prepared from 7b (2.2 g; 10.1 mmol) using the method described in the synthesis of 8c.

$^1$H-NMR (DMSO-d$_6$): δ (ppm) 2.38 (s, 3H, CH$_3$), 4.52 (s, 2H, CH$_2$), 5.3-5.5 (bs, 1H, exchangeable, hydroxyl-OH), 7.03 (d, 1H, 2.6 Hz, C$^5$—H), 7.11 (d, 2.4 Hz, C$^3$—H), 9.02 (bs, 1H, exchangeable, phenol-OH)

4-Hydroxymethyl-2-methylsulfanylphenol (8c)

With ice-cooling, a solution of 7d (1.37 g; 7.4 mmol) in abs. tetrahydrofuran (THF; 15 ml) was added to a suspension of 95% pure LiAlH$_4$ (0.55 g; 14 mmol) in absolute THF (10 ml) in a three-necked flask (which had been dried by heating and flushed with argon) such that there was only a moderate evolution of gas. After the addition had ended, cooling was removed and the reaction mixture was stirred at room temperature for 30 min and at 55-65° C. for a further 21 h. With ice-cooling, ice-water was added to the reaction mixture. The precipitate of Al(OH)$_3$ was dissolved by adding 10% strength sulfuric acid, and the aqueous-acidic solution (pH 1) was extracted with diethyl ether (3×50 ml). The combined ethereal extract was extracted with 10% strength aqueous sodium hydroxide solution (2×25 ml). The combined sodium hydroxide solution was neutralized with 20% strength hydrochloric acid. The precipitate (8c) was filtered off, washed with H$_2$O and dried. A further charge of 8c was obtained by extraction of the neutral aqueous solution with diethyl ether. The ethereal extract was washed with saturated NaCl solution, dried over Na$_2$SO$_4$ and concentrated: crystalline white solid.

$^1$H-NMR (CDCl$_3$): δ (ppm) 2.34 (s, 3H, CH$_3$), 4.60 (s, 2H, CH$_2$), 6.97 (d, 1H, 8.3 Hz, C$^6$—H), 7.24 (dd, 1H, 2.0/8.4 Hz, C$^5$—H), 7.50 (d, 1H, 2.0 Hz, C$^3$—H), OH not visible

EXAMPLE 9

2-Hydroxy-5-methylsulfanylbenzaldehyde (9a)

The title compound was obtained as a byproduct in the synthesis of 8a.

$^1$H-NMR (CDCl$_3$): δ (ppm) 2.48 (s, 3H, CH$_3$), 6.96 (d, 1H, 9.8 Hz, C$^3$—H), 7.48-7.54 (m, 2H, C$^4$—/C$^6$—H), 9.87 (s, 1H, exchangeable, OH), 10.91 (s, 1H, aldehyde-H)

EXAMPLE 10

4-(3-Chloroethyl)benzenesulfonyl chloride (10a)

With ice-cooling, (2-chloroethyl)benzene (14.0 g; 0.1 mol) was added dropwise over a period of 40 min to chlorosulfonic acid (72 g). The brown solution was stirred at room temperature for 24 h, cooled in an ice-bath and, a little at a time, added to ice, where a viscous material separated out that could not be filtered. The aqueous solution was extracted with ethyl acetate (3×). The combined organic extract was washed with 10% strength NaHCO$_3$ solution, dried over Na$_2$SO$_4$ and concentrated. The oily residue was taken up in tert-butyl methyl ether/petroleum ether. The solution was scratched with a glass rod and cooled. The white crystals were filtered off and dried. Further reaction product was obtained from the mother liquor. The crude product was used without further purification for the synthesis of 11a.

$^1$H-NMR (CDCl$_3$): δ (ppm) 3.20 (t, 2H, 6.8 Hz, CH$_2$), 3.79 (t, 2H, 6.8 Hz, CH$_2$), 7.46-7.53 (m, 2H, phenyl), 7.97-8.04 (m, 2H, phenyl)

4-(3-Chloropropyl)benzenesulfonyl chloride (10b)

10b was prepared from (3-chloropropyl)benzene (15.5 g; 0.1 mol) using the method described in the synthesis of 10a. The crude product was used without further purification for the synthesis of 11b.

MS: m/z (%) 253 (90. M$^+$), 217 (100. M$^+$—Cl), 189 (35), 153 (97, M$^+$—SO$_2$Cl), 125 (94), 119 (65, phenylpropylcarbenium$^+$), 91(90), 77 (29, phenyl$^+$)

EXAMPLE 11

1-(3-Chloroethyl)-4-methylsulfanylbenzene (11a)

11a was prepared from 10a (12.0 g; 0.05 mol) using the method described in the synthesis of 11b.

$^1$H-NMR (CDCl$_3$): δ (ppm) 2.47 (s, 3H, CH$_3$), 3.02 (t, 2H, 7.4 Hz, CH$_2$), 3.68 (t, 2H, 7.5 Hz, CH$_2$), 7.11-7.25 (m, 4H, phenyl)

1-(3-Chloropropyl)-4-methylsulfanylbenzene (11b)

At room temperature, a solution of 10b (12.7 g; 5.0 mmol) in diethyl ether (75 ml) was added dropwise over a period of 2.5 h to a suspension of LiAlH$_4$ (2.9 g; 7.6 mmol) in diethyl ether (50 ml). After the addition had ended, the reaction mixture was stirred at room temperature and with occasional addition of LiAlH$_4$ until no more starting material could be detected by thin-layer chromatography (2.5 h). With ice-cooling, ice was introduced into the reaction mixture, and the aqueous phase was acidified with 10% hydrochloric acid (pH 1). The organic phase was removed and the aqueous phase was extracted with diethyl ether (3×). The combined organic extract was washed with 10% strength aqueous sodium hydroxide solution (4×50 ml) until it was virtually colorless. Dimethyl sulfate (9.0 g; 7.0 mmol) was added to the combined sodium hydroxide extract, and the mixture was stirred at room temperature for 16.5 h. The oily sediment was taken up in diethyl ether. The organic phase was separated off and the aqueous phase was again extracted with diethyl ether (2×). The combined organic extract was dried over Na$_2$SO$_4$ and concentrated. The brown oily residue was subjected to a kugelrohr distillation (0.2 mbar, 250° C.).

$^1$H-NMR (CDCl$_3$): δ (ppm) 2.01-2.11 (m, 2H, CH$_2$), 2.46 (s, 3H, CH$_3$), 2.73 (t, 2H, 7.1 Hz, CH$_2$), 3.51 (t, 2H, 6.5 Hz, CH$_2$), 7.09-7.25 (m, 4H, phenyl)

EXAMPLE 12

1-(2-Chloroethyl)-4-methanesulfinylbenzene (12a)

With cooling, a 35% strength solution of H$_2$O$_2$ (0.9 g; 9.3 mmol) was added to a solution of 11a (1.5 g; 8.0 mmol) in glacial acetic acid (20 ml). After the addition had ended, the reaction mixture was stirred at room temperature for 2.5 h diluted with cooling with ice-water and adjusted to pH 8 using 25% strength ammonia water. The oily white sediment was taken up in diethyl ether and the aqueous phase was extracted with diethyl ether (3×). The combined organic extract was dried over Na$_2$SO$_4$ and concentrated.

$^1$H-NMR (CDCl$_3$): δ (ppm) 2.73 (s, 3H, CH$_3$), 3.14 (t, 2H, 7.1 Hz, CH$_2$), 3.76 (t, 2H, 7.1 Hz, CH$_2$), 7.38-7.42 (m, 2H, phenyl), 7.60-7.64 (m, 2H, phenyl)

1-(3-Chloropropyl)-4-methanesulfinylbenzene (12b)

12b was prepared from 11b (2.0 g; 10.0 mmol) using the method described in the synthesis of 12a. M.p.: 46° C.

General methods for preparing the compounds of the formula I:

Preparation of the 2-arylalkyl- or alkylsulfanylimidazoles (General Method A)

A suspension of the respective imidazole-2-thione (1 equivalent), of the respective base (1.2 equivalents) and of the respective arylalkyl or alkyl halide (1 equivalent) in ethanol/THF (8+2) was stirred under reflux until no more imidazole-2-thione could be detected by thin-layer chromatography. The reaction mixture was cooled to room temperature and filtered. The filtrate, which in most cases was of red/orange color, was concentrated, and the residue was purified by column chromatography, recrystallization or trituration. The compounds 13a-c, 14a-c and 17a-m were prepared in this manner.

Preparation of the 2-benzylsulfanylimidazoles Having Phenolic Functionality in the Radical R$^2$ (General Method B)

By addition of 10% strength hydrochloric acid (10-15 drops), the imidazole-2-thione 1a (1 equivalent) was dissolved in glacial acetic acid (5 ml). The respective benzyl alcohol (1 equivalent) was added to the initial charge, which had a light-yellow color, and the reaction mixture was stirred at a suitable temperature (temperature/time) until no more 1a could be detected by thin-layer chromatography. In the case of the sulfoxides 18g-i, a 35% strength solution of H$_2$O$_2$ was added, and the reaction mixture was stirred at room temperature for a further 4 h. The reaction mixture was diluted with H$_2$O (5 ml) and adjusted to pH 8 using 25% strength ammonia water. The precipitate was filtered off and washed with water. The crude product was purified by column chromatography, recrystallization or trituration. The imidazol-2-ylsulfanylmethylphenols 18a-i were prepared in this manner.

Preparation of N-substituted 2-aminopyridines (General Method C)

Under argon, the respective 5-(2-halopyridin-4-yl)imidazole (1 equivalent) was suspended in the respective amine (about 10 equivalents). The reaction mixture was stirred at the respective temperature until no more starting material could be detected by thin-layer chromatography. The reaction mixture was cooled to room temperature and taken up in 10% citric acid which had been adjusted beforehand to pH 5 using 20% strength NaOH. The aqueous emulsion was extracted with ethyl acetate (3×). The combined organic extract was washed with 10% strength citric acid/pH 5 (1×), 10% strength Na$_2$CO$_3$ solution (2×) and saturated NaCl solution (1×), dried over Na$_2$SO$_4$ and concentrated. The oily residue was separated by column chromatography. The aminopyridines 25f-p, 26c-e and 27c-d were prepared in this manner.

EXAMPLE 13

3-[5-(4-Fluorophenyl)-2-(4-methylsulfanylbenzylsulfanyl)-3H-imidazol-4-yl]-pyridine (13a)

Using the general method A, the title compound was obtained from 1b (0.42 g; 1.5 mmol) and 2 (0.25 g; 1.4 mmol) after a reaction time of 4.5 hours and separation by column chromatography (SiO$_2$ 60, CH$_2$Cl$_2$/EtOH 9+1).

M.p. 163° C.

IR (ATR) (attenuated total reflection) 1506, 1493, 1222 (C—F), 837, 806 cm$^{-1}$ $^1$H-NMR (DMSO-d$_6$): δ (ppm) 2.45 (s, 3H, CH$_3$), 4.38 (s, 2H, CH$_2$), 7.19-7.49 (m, 10H, 3-Pyr, 4-F-Ph and 4-MeS-Ph), 7.78-7.82 (m, 1H, 3-Pyr), 8.45-8.47 (m, 1H, 3-Pyr), 8.61 (s, 1H, 3-Pyr), 12.71 (bs, 1H, exchangeable, NH)

3-[5-(4-Fluorophenyl)-2-(4-methanesulfinylbenzylsulfanyl)-3H-imidazol-4-yl]-pyridine (13b).

Using the general method A, the title compound was obtained from 1b (0.42 g; 1.5 mmol) and 3 (0.27 g; 1.5 mmol) after a reaction time of 8 hours and separation by column chromatography (SiO$_2$ 60, CH$_2$Cl$_2$/EtOH 9+1).

M.p. 127° C.

IR (ATR): 1506, 1222 (C—F), 1027 (S=O), 1013, 838, 811 cm$^{-1}$ $^1$H-NMR (DMSO-d$_6$): δ (ppm) 3.19 (s, 3H, CH$_3$), 4.46 (s, 2H, CH$_2$), 7.16-7.46 (m, 5H, 3-Pyr and 4-F-Ph), 7.56-7.66 (m, 4H, 4-MeS(O)-Ph), 7.72-7.81 (m, 1H, 3-Pyr), 8.41-8.62 (m, 2H, 3-Pyr), 12.77 (bs, 1H, exchangeable, NH)

3-[5-(4-Fluorophenyl)-2-(4-methanesulfonylbenzylsulfanyl)-3H-imidazol-4-yl]-pyridine (13c).

Using the general method A, the title compound was obtained from 1b (0.42 g; 1.5 mmol) and 4 (0.29 g; 1.43 mmol) and with addition of Na$_2$CO$_3$ (0.43 g; 4.1 mmol) after a reaction time of 6.5 hours and trituration with hot ethyl acetate. M.p. 129° C.

IR (ATR): 1506, 1296 (SO2), 1222 (C—F), 1145 (SO2), 1089, 839, 812 cm$^{-1}$ $^1$H-NMR (DMSO-d$_6$): δ (ppm) 3.19 (s, 3H, CH$_3$), 4.50 (s, 2H, CH$_2$), 7.17-7.45 (m, 5H, 3-Pyr and 4-F-Ph), 7.64-7.90 (m, 5H, 3-Pyr and 4-MeSO$_2$-Ph), 8.43-8.61 (m, 2H, 3-Pyr), 12.78 (bs, 1H, exchangeable, NH)

EXAMPLE 14

4-[5-(4-Chlorophenyl)-2-(4-methylsulfanylbenzylsulfanyl)-3H-imidazol-4-yl]-pyridine (14a)

Using the general method A, the title compound was obtained from 1c (0.26 g; 0.9 mmol) and 6 (0.15 g; 0.87 mmol) and with addition of Na$_2$CO$_3$ (two spatula tips) after a reaction time of 6.5 hours and separation by column chromatography (SiO$_2$ 60, CH$_2$Cl$_2$/EtOH 9+1). M.p. 236° C.

IR (ATR): 1600, 1492, 1094, 1005, 968, 829, 684 (C—Cl), 561 cm$^{-1}$ $^1$H-NMR (DMSO-d$_6$): δ (ppm) 2.44 (s, 3H, CH$_3$), 4.38 (s, 2H, CH$_2$), 7.18-7.56 (m, 10H, 4-Pyr, 4-Cl-Ph and 4-MeS-Ph), 8.45-8.55 (m, 2H, 4-Pyr), 12.86 (bs, 1H, exchangeable, NH)

4-[5-(4-Chlorophenyl)-2-(4-methanesulfinylbenzylsulfanyl)-3H-imidazol-4-yl]-pyridine (14b)

Using the general method A, the title compound was obtained from 1c (0.26 g; 0.9 mmol) and 3 (0.16 g; 0.85 mmol) and with addition of Na$_2$CO$_3$ after a reaction time of 6.5 hours and separation by column chromatography (SiO$_2$ 60, CH$_2$Cl$_2$/EtOH 9+1). M.p. 224° C.

IR (ATR): 1600, 1510, 1490, 1033 (S=O), 1001, 967, 829, 677 cm$^{-1}$ (C—Cl)

$^1$H-NMR (DMSO-d$_6$): δ (ppm) 2.70 (s, 3H, CH$_3$), 4.47 (s, 2H, CH$_2$), 7.31-7.65 (m, 10H, 4-Pyr, 4-Cl-Ph and 4-MeS(O)-Ph), 8.44-8.54 (m, 2H, 4-Pyr), 12.87 (bs, 1H, exchangeable, NH)

4-[5-(4-Chlorophenyl)-2-(4-methanesulfonylbenzylsulfanyl)-3H-imidazol-4-yl]-pyridin (14c)

Using the general method A, the title compound was obtained from 1c (0.26 g; 0.9 mmol) and 4 (0.18 g; 0.9 mmol) and with addition of Na$_2$CO$_3$ (two spatula tips) after a reaction time of 6.5 hours and separation by column chromatography (SiO$_2$ 60, CH$_2$Cl$_2$/EtOH 9+1). M.p. 232° C.

IR (ATR): 1603, 1490, 1300 (SO2), 1141 (SO2), 1086, 1002, 952, 829, 681 (C—Cl), 550 cm$^{-1}$ $^1$H-NMR (DMSO-d$_6$): δ (ppm) 3.19 (s, 3H, CH$_3$), 4.52 (s, 2H, CH$_2$), 7.32-7.58 (m, 6H, 4-Pyr and 4-Cl-Ph), 7.67 (d, 2H, 8.2 Hz, 4-MeSO$_2$-Ph), 7.88 (d, 2H, 8.3 Hz, 4-MeSO$_2$-Ph), 8.45-8.55 (m, 2H, 4-Pyr), 12.89 (bs, 1H, exchangeable, NH)

EXAMPLE 15

4-[5-(4-Bromophenyl)-2-(4-methylsulfanylbenzylsulfanyl)-3H-imidazol-4-yl]-pyridine (15a)

Using the general method A, the title compound was obtained from 1d (0.25 g; 0.75 mmol) and 2 (0.13 g; 0.72 mmol) after a reaction time of 5 hours and separation by column chromatography (SiO$_2$ 60, CH$_2$Cl$_2$/EtOH 9+1).

IR (ATR): 1600, 1517, 1490, 1089, 1069, 1003, 968, 826 cm$^{-1}$ $^1$H-NMR (DMSO-d$_6$): δ (ppm) 2.43 (s, 3H, CH$_3$), 4.36 (s, 2H, CH$_2$), 7.16-7.87 (m, 10H, 4-Pyr, 4-Br-Ph and 4-MeS-Ph), 8.45-8.55 (m, 2H, 4-Pyr), 12.90 (bs, 1H, exchangeable, NH)

4-[5-(4-Bromophenyl)-2-(4-methanesulfinylbenzylsulfanyl)-3H-imidazol-4-yl]-pyridine (15b)

Using the general method A, the title compound was obtained from 1d (0.25 g; 0.75 mmol) and 3 (0.14 g; 0.72 mmol) after a reaction time of 10 hours and separation by column chromatography (SiO$_2$ 60, CH$_2$Cl$_2$/EtOH 9+1).

M.p. 222° C.

IR (ATR): 1604, 1487, 1035 (S=O), 1010, 1000, 966, 822 cm$^{-1}$ $^1$H-NMR (DMSO-d$_6$): δ (ppm) 2.71 (s, 3H, CH$_3$), 4.48 (s, 2H, CH$_2$), 7.40-7.62 (m, 20H, 4-Pyr, 4-Br-Ph and 4-MeS(O)-Ph), 8.49-8.57 (m, 2H, 4-Pyr), 12.90 (bs, 1H, exchangeable, NH)

4-[S-(4-Bromophenyl)-2-(4-methanesulfonylbenzylsulfanyl)-3H-imidazol-4-yl]-pyridine (15c)

Using the general method A, the title compound was obtained from 1d (0.25 g; 0.75 mmol) and 4 (0.15 g; 0.72 mmol) after a reaction time of 5 hours and separation by column chromatography (SiO$_2$ 60, CH$_2$Cl$_2$/EtOH 9+1).

M.p. 226° C.

IR (ATR): 1605, 1318, 1303 (SO2), 1145 (SO2), 1003, 967, 957, 827, 822 cm$^{-1}$ $^1$H-NMR (DMSO-d$_6$): δ (ppm) 3.18 (s, 3H, CH$_3$), 4.50 (s, 2H, CH$_2$), 7.33-7.89 (m, 10H, 4-Pyr, 4-Br-Ph and 4-MeSO$_2$-Ph), 8.45-8.54 (m, 2H, 4-Pyr), 12.91 (bs, 1H, exchangeable, NH)

EXAMPLE 16

4-[2-(4-Methylsulfanylbenzylsulfanyl)-5-phenyl-3H-imidazyl-4-yl]pyridine (16a)

Using the general method A, the title compound was obtained from 1e (0.38 g; 1.5 mmol) and 2 (0.25 g; 1.4 mmol) after a reaction time of 5.75 hours and separation by column chromatography (SiO$_2$ 60, CH$_2$Cl$_2$/EtOH 9+1).

M.p. 213° C.

IR (ATR): 1601, 1491, 1417, 1094, 1004, 967, 828, 771, 700 cm$^{-1}$ $^1$H-NMR (DMSO-d$_6$): δ (ppm) 2.44 (s, 3H, CH$_3$), 4.38 (s, 2H, CH$_2$), 7.18-7.58 (m, 11H 4-Pyr, Ph and 4-MeS-Ph), 8.44-8.47 (m, 2H, 4-Pyr), 12.82 (bs, 1H, exchangeable, NH)

4-[2-(4-Methanesulfinylbenzylsulfanyl)-5-phenyl-3H-imidazol-4-yl]pyridine (16b)

Using the general method A, the title compound was obtained from 1e (0.38 g; 1.5 mmol) and 3 (0.27 g; 1.43 mmol) after a reaction time of 5.5 hours and separation by column chromatography (SiO$_2$ 60, CH$_2$Cl$_2$/EtOH 9+1).

M.p. 189° C.

IR (ATR): 1603, 1494, 1051 (S=O), 1003, 833, 701 cm−1

$^1$H-NMR (DMSO-d$_6$): δ (ppm) 2.71 (s, 3H, CH$_3$), 4.48 (s, 2H, CH$_2$), 7.32-7.52 (m, 7H, 4-Pyr and Ph), 7.57-7.67 (m, 4H, 4-MeS(O)-Ph), 8.45-8.54 (m, 2H, 4-Pyr), 12.84 (bs, 1H, exchangeable, NH)

4-[2-(4-Methanesulfonylbenzylsulfanyl)-5-phenyl-3H-imidazol-4-yl]pyridine (16c)

Using the general method A, the title compound was obtained from 1e (0.38 g; 1.5 mmol) and 4 (0.29 g; 1.43 mmol) after a reaction time of 4.25 hours and separation by column chromatography (SiO$_2$ 60, CH$_2$Cl$_2$/EtOH 9+1).

M.p. 247° C.

IR (ATR): 1602, 1298 (SO2), 1145 (SO2), 1006, 953, 827, 775, 701 cm$^{-1}$ $^1$H-NMR (DMSO-d$_6$): δ (ppm) 3.21 (s, 3H, CH$_3$), 4.54 (s, 2H, CH$_2$), 7.31-7.58 (m, 7H, 4-Pyr and Ph), 7.70 (d, 2H, 8.3 Hz, 4-MeSO$_2$-Ph), 7.91 (d, 2H, 8.3 Hz, 4-MeSO$_2$-Ph), 8.45-8.59 (m, 2H, 4-Pyr), 12.87 (bs, 1H, exchangeable, NH)

EXAMPLE 17

4-{5-(4-Fluorophenyl)-2-[2-(4-methanesulfinylphenyl)ethylsulfanyl]-1H-imidazol-4-yl}pyridine (17a)

Using the general method A, the title compound was obtained from 1a (0.25 g; 0.9 mmol) and 12a (0.22 g; 1.1 mmol) and with addition of Na$_2$CO$_3$ (1 spatula tip) and a catalytic amount of NaI after a reaction time of 50 hours and purification by column chromatography (SiO$_2$ 60, CH$_2$Cl$_2$/EtOH 9+1).

M.p. 177° C.

IR (ATR): 1221 (C—F), 1032 cm$^{-1}$ (S=O)

$^1$H-NMR (DMSO-d$_6$): δ (ppm) 2.71 (s, 3H, CH$_3$), 3.06-3.13 (m, 2H, CH$_2$), 3.42-3.49 (m, 2H, CH$_2$), 7.25-7.65 (m, 10H, 4-Pyr, 4-F-Ph and 4-MeS(O)-Ph), 8.40-8.58 (m, 2H, 4-Pyr), 12.80 (bs, 1H, exchangeable, NH)

4-{5-(4-Fluorophenyl)-2-[2-(4-methanesulfinylphenyl)propylsulfanyl]-1H-imidazol-4-yl}pyridine (17b)

Using the general method A, the title compound was obtained from 1a (0.25 g; 0.9 mmol) and 12b (0.22 g; 1.0 mmol) and with addition of Na$_2$CO$_3$ (1 spatula tip) and a catalytic amount of NaI after a reaction time of 40 hours and purification by column chromatography (SiO$_2$ 60, CH$_2$Cl$_2$/EtOH 9+1).

M.p. 142° C.

IR (ATR): 1222 (C—F), 1043 cm$^{-1}$ (S=O)

$^1$H-NMR (DMSO-d$_6$): δ (ppm) 1.95-2.09 (m, 2H, CH$_2$), 2.71 (s, 3H, CH$_3$), 2.82 (t, 2H, 7.4 Hz, CH$_2$), 3.15 (t, 2H, 7.0 Hz, CH$_2$), 7.25-7.62 (m, 10H, 4-Pyr, 4-F-Ph and 4-MeS(O)-Ph, 8.46-8.49 (m, 2H, 4-Pyr), 12.86 (bs, 1H, exchangeable, NH)

4-[2-Benzylsulfanyl-5-(4-fluorophenyl)-1H-imidazol-4-yl]pyridine (17c)

Using the general method A, the title compound was obtained from 1a (0.28 g; 1.0 mmol) and 1-chloromethylbenzene (0.13 g; 1.0 mmol) after a reaction time of 6 hours and trituration with MeOH. M.p. 223° C.

IR (ATR): 1233 cm$^{-1}$ (C—F)

$^1$H-NMR (DMSO-d$_6$): δ (ppm) 4.41 (s, 2H, CH$_2$), 7.23-7.51 (m, 11H, 4-Pyr, 4-F-Ph and Bz), 8.44-8.47 (m, 2H, 4-Pyr), 12.82 (bs, 1H, exchangeable, NH)

4-[5-(4-Fluorophenyl)-2-phenethylsulfanyl-1H-imidazol-4-yl]pyridine (17d)

Using the general method A, the title compound was obtained from 1a (0.5 g; 1.9 mmol) and 2-chloroethylbenzene (0.28 g; 2.0 mmol) and with addition of Na$_2$CO$_3$ (1 spatula tip) and a catalytic amount of NaI after a reaction time of 70 hours and trituration with EtOH. M.p. 257° C.

IR (ATR): 1223 cm$^{-1}$ (C—F)

$^1$H-NMR (DMSO-d$_6$): δ (ppm) 2.99 (t, 2H, 7.4 Hz, CH$_2$), 3.40 (t, 2H, 7.5 Hz, CH$_2$), 7.17-7.53 (m, 11H, 4-Pyr, 4-F-Ph and Bz), 8.44-8.46 (m, 2H, 4-Pyr), NH not visible 4-[5-(4-Fluorophenyl)-2-(3-phenylpropylsulfanyl)-1H-imidazol-4-yl]pyridine (17e)

Using the general method A, the title compound was obtained from 1a (0.5 g; 1.9 mmol) and 3-chloropropylbenzene (0.31 g; 2.0 mmol) and with addition of Na$_2$CO$_3$ (1 spatula tip) and a catalytic amount of NaI after a reaction time of 70 hours and trituration with EtOH. M.p. 183° C.

IR (ATR): 1226 cm$^{-1}$ (C—F)

$^1$H-NMR (DMSO-d$_6$): δ (ppm) 1.90-2.04 (m, 2H, CH$_2$), 2.72 (t, 2H, 7.4 Hz, CH$_2$), 3.12 (t, 2H, 7.0 Hz, CH$_2$), 7.18-7.51 (m, 11H, 4-Pyr, 4-F-Ph and Bz), 8.37-8.44 (m, 2H, 4-Pyr), 12.82 (bs, 1H, exchangeable, NH)

[5-(4-Fluorophenyl)-4-pyridin-4-yl-1H-imidazol-2-ylsulfanyl]acetonitrile (17f)

Using the general method A, the title compound was obtained from 1a (1.1 g; 4.0 mmol) and chloroacetonitrile (0.30; 4.0 mmol) after a reaction time of 18 hours and purification by column chromatography (SiO$_2$ 60, ethyl acetate).

M.p. 219° C.

IR (ATR): 2243 (CN), 1226 cm$^{-1}$ (C—F)

$^1$H-NMR (DMSO-d$_6$): δ (ppm) 4.32 (s, 2H, CH$_2$), 7.34-7.57 (m, 6H, 4-Pyr and 4-F-Ph), 8.50-8.52 (m, 2H, 4-Pyr), 13.20 (bs, 1H, exchangeable, NH)

4-[5-(4-Fluorophenyl)-2-(naphthalen-1-ylmethylsulfanyl)-1H-imidazol-4-yl]-pyridine (17g)

Using the general method A, the title compound was obtained from 1a (0.28 g; 1.0 mmol) and 1-chloromethylnaphthol (0.18 g; 1.0 mmol) after a reaction time of 6.5 hours and purification by column chromatography (SiO$_2$ 60, ethyl acetate). M.p. 364° C.

IR (ATR): 1225 cm$^{-1}$ (C—F)

$^1$H-NMR (DMSO-d$_6$): δ (ppm) 4.90 (s, 2H, CH$_2$), 7.25-7.62 (m, 10H, 4-Pyr, 4-F-Ph and naphthyl), 7.80-7.98 (m, 2H, naphthyl), 8.20-8.23 (m, 1H, naphthyl), 8.48-8.52 (m, 2H, 4-Pyr), 12, (bs, 1H, exchangeable, NH)

4-[2-cyclohexylmethylsulfanyl-5-(4-fluorophenyl)-1H-imidazol-4-yl]pyridine (17h)

Using the general method A, the title compound was obtained from 1a (0.25 g; 0.9 mmol) and 1-chloromethylcyclohexane (0.18 g; 1.0 mmol) and with addition of Na$_2$CO$_3$ (1 spatula tip) and a catalytic amount of NaI after a reaction time of 47 hours and trituration with EtOH. M.p. 235° C.

IR (ATR): 2922, 2852 (c-Hex), 1222 cm$^{-1}$ (C—F)

$^1$H-NMR (DMSO-d$_6$): δ (ppm) 0.95-1.23 (m, 5H, cyclo-Hex), 1.51-1.85 (m, 6H, cyclo-Hex), 3.06 (d, 2H, 6.7 Hz, CH$_2$), 7.22-7.51 (m, 6H, 4-Pyr and 4-F-Ph), 8.43-8.45 (m, 2H, 4-Pyr), 12.76 (bs, 1H, exchangeable, NH)

4-[5-(4-Fluorophenyl)-2-methylsulfanyl-1H-imidazol-4-yl]pyridine (17i)

Using the general method A, the title compound was obtained from 1a (0.41 g; 1.5 mmol) and methyl iodide (0.27 g; 1.9 mmol) after a reaction time of 8 hours and trituration with EtOH. M.p. 263° C.

IR (ATR): 1226 cm$^{-1}$ (C—F)

$^1$H-NMR (DMSO-d$_6$): δ (ppm) 2.61 (s, 3H, CH$_3$), 7.22-7.51 (m, 6H, 4-Pyr and 4-F-Ph), 8.42-8.45 (m, 2H, 4-Pyr), NH not visible 4-[5-(4-Fluorophenyl)-2-(2-methylsulfanylbenzylsulfanyl)-1H-imidazol-4-yl]-pyridine (17j)

Using the general method A, the title compound was obtained from 1a (0.28 g; 1.0 mmol) and 1-chloromethyl-2-methylsulfanylbenzene (0.17 g; 1.0 mmol) after a reaction time of 5.5 hours and purification by column chromatography (SiO$_2$ 60, ethyl acetate). M.p. 223° C.

IR (ATR): 1228 cm$^{-1}$ (C—F)

$^1$H-NMR (CD$_3$OD): δ (ppm) 2.51 (s, 3H, CH$_3$), 4.44 (s, 2H, CH$_2$), 7.13-7.48 (m, 10H, 4-Pyr, 4-F-Ph and 2-MeS-Ph), 8.43-8.46 (m, 2H, 4-Pyr)

4-[5-(4-Fluorophenyl)-2-(2-methanesulfinylbenzylsulfanyl)-1H-imidazol-4-yl]-pyridine (17k)

Using the general method A, the title compound was obtained from 1a (0.28 g; 1.0 mmol) and 1-chloromethyl-2-methanesulfinylbenzene (0.18 g; 1.0 mmol) after a reaction time of 4 hours and recrystallization from methanol/ethyl acetate (1+1). M.p. 205° C.

IR (KBr): 1213 (C—F), 1033 cm$^{-1}$ (S=O)

$^1$H-NMR (CD$_3$PD): δ (ppm) 2.87 (s, 3H, CH$_3$), 4.50 (d, 1H, 13.6 Hz, CH$_2$), 4.62 (d, 1H, 13.6 Hz, CH$_2$), 7.24-7.33 (m, 2H, 4-F-Ph), 7.47-7.62 (m, 5H, 4-F-Ph, C$^4$—/C$^5$—/C$^6$—H 2-MeS(O)-Ph), 7.95 (d, 1 H, 7.2 Hz, C$^3$—H 2-MeS(O)-Ph), 7.99-8.03 (m, 2H, 4-Pyr), 8.55-8.58 (m, 2H, 4-Pyr)

4-[5-(4-Fluorophenyl)-2-(3-methylsulfanylbenzylsulfanyl)-1H-imidazol-4-yl]-pyridine (17l)

Using the general method A, the title compound was obtained from 1a (1.1 g; 4.1 mmol) and 1-chloromethyl-3-methylsulfanylbenzene (0.7 g; 4.1 mmol) after a reaction time of 11 hours and recrystallization from EtOH. M.p. 218° C.

IR (KBr): 1225 cm$^{-1}$ (C—F)

$^1$H-NMR (DMSO-d$_6$): δ (ppm) 2.40 (s, 3H, CH$_3$), 4.46 (s, 2H, CH$_2$), 7.16-7.43 (m, 6H, 4-F-Ph and 3-MeS-Ph), 7.56-7.63 (m, 2H, 4-F-Ph), 7.90-7.93 (m, 2H, 4-Pyr), 8.66-8.69 (m, 2H, 4-Pyr), NH not visible 4-[5-(4-Fluorophenyl)-2-(3-methanesulfinylbenzylsulfanyl)-1H-imidazol-4-yl]-pyridine (17m)

A 35% strength solution of H$_2$O$_2$ (0.13 ml; 1.3 mmol) was added dropwise to a suspension of 17 l (0.50 g; 1.2 mmol) in glacial acetic acid (7 ml). The reaction mixture was stirred at room temperature for 20.5 h, diluted with H$_2$O (5 ml), adjusted to pH 9 using 25% strength ammonia water and extracted with ethyl acetate (3×). The combined organic extract was washed with saturated NaCl solution (3×) and dried over Na$_2$SO$_4$. The oily crude product obtained after removal of the solvent was triturated with diethyl ether/ethyl acetate (1+1) and the semi-solid residue was purified by column chromatography (RP-18, MeOH). M.p. 171° C.

IR (KBr): 1228 (C—F), 1019 cm$^{-1}$ (S=O)

$^1$H-NMR (CD$_3$OD): δ (ppm) 2.67 (s, 3H, CH$_3$), 4.37 (s, 2H, CH$_2$), 7.13-7.21 (m, 2H, 4-F-Ph), 7.37-7.58 (m, 8H, 4-Pyr, 4-F-Ph and 3-MeS(O)-Ph), 8.40-8.43 (m, 2H, 4-Pyr)

EXAMPLE 18

2-[5-(4-Fluorophenyl)-4-pyridin-4-yl-1H-imidazol-2-ylsulfanylmethyl]phenol (18a)

Using the general method B (23 h, room temperature), the title compound was obtained from 1a (0.20 g; 0.7 mmol) and 2-hydroxymethylphenol (0.10 g; 0.8 mmol) after trituration with EtOH. M.p. 200° C. (decomposition)

IR (ATR): 1266 (OH bending), 1222 (C—F), 1005 (C—O)

$^1$H-NMR (DMSO-d$_6$): δ (ppm) 4.37 (s, 2H, CH$_2$), 6.70-6.85 (m, 2H, 2-HO-Ph), 7.05-7.14 (m, 1H, 2-HO-Ph), 7.23-7.53 (m, 7H, 4-Pyr, 4-F-Ph and 2-HO-Ph), 8.46-8.49 (m, 2H, 4-Pyr), 9.95 (bs, 1 H, exchangeable, OH), 12.81 (bs, 1H, exchangeable, NH)

3-[5-(4-Fluorophenyl)-4-pyridin-4-yl-1H-imidazol-2-ylsulfanylmethyl]phenyl (18b)

Using the general method B (9 h, reflux), the title compound was obtained from 1a (0.20 g; 0.7 mmol) and 3-hydroxymethylphenol (0.10 g; 0.8 mmol) after purification by column chromatography (SiO$_2$ 60, CH$_2$Cl$_2$/EtOH 9+1). M.p. 230° C.

IR (ATR): 1287 (OH bending), 1241 (C—F), 1007 cm$^{-1}$ (C—O)

$^1$H-NMR (DMSO-d$_6$): δ (ppm) 4.34 (s, 2H, CH$_2$), 6.65 (dd, 1H, 1.4/8.0 Hz, 3-HO-Ph C$^4$—H), 6.79-6.82 (m, 2H, 3-HO-Ph C$^2$—/C$^6$—H), 7.07-7.15 (m, 1H, 3-HO-Ph C$^5$—H), 7.27-7.53 (m, 6H, 4-Pyr and 4-F-Ph), 9.45 (s, 1H, exchangeable, OH), 12.83 (bs, 1H, exchangeable, NH)

4-[5-(4-Fluorophenyl)-4-pyridin-4-yl-1H-imidazol-2-ylsulfanylmethyl]phenol (18c)

Using the general method B (14 h, room temperature), the title compound was obtained from 1a (0.20 g; 0.7 mmol) and 4-hydroxymethylphenol (0.10 g; 0.8 mmol) after purification by column chromatography (SiO$_2$ 60, CH$_2$Cl$_2$/EtOH 9+1). M.p. 250° C. (decomposition)

IR (ATR): 1271 (OH bending), 1232 (C—F), 1004 cm$^{-1}$ (C—O)

$^1$H-NMR (DMSO-d$_6$): δ (ppm) 4.32 (s, 2H, CH$_2$), 6.69 (d, 2H, 7.5 Hz, 4-HO-Ph), 7.19 (d, 2H, 7.9 Hz, 4-HO-Ph), 7.27-7.51 (m, 6H, 4-Pyr and 4-F-Ph), 8.43-8.53 (m, 2H, 4-Pyr), 9.41 (s, 1H, exchangeable, OH), 12.79 (bs, 1H, exchangeable, NH)

2-[5-(4-Fluorophenyl)-4-pyridin-4-yl-1H-imidazol-2-ylsulfanylmethyl]-4-methylsulfanylphenol (18d)

Using the general method B (1 h, room temperature), the title compound was obtained from 1a (0.50 g; 2.9 mmol) and 8a (0.50 g; 2.9 mmol) after trituration with MeOH. M.p. 243° C.

IR (KBr): 1275 (OH bending), 1230 (C—F), 1005 cm$^{-1}$ (C—O)

$^1$H-NMR (DMF-d$_7$): δ (ppm) 2.36 (s, 3H, CH$_3$), 4.46 (s, 2H, CH$_2$), 6.90 (d, 1H, 8.4 Hz, 2-HO-Ph C$^3$—H), 7.13 (dd, 1H, 2.3/8.3 Hz, 2-HO-Ph C$^4$—H), 7.27-7.35 (m, 3H, 4-F-Ph and 2-HO-Ph C$^6$—H), 7.51-7.53 (m, 2H, 4-Pyr), 7.58-7.65 (m, 2H, 4-F-Ph), 8.52-8.55 (m, 2H, 4-Pyr), 10.30-10.70 (bs, 1H, exchangeable, NH), OH not visible 4-Chloro-2-[5-(4-fluorophenyl)-4-pyridin-4-yl-1H-imidazol-2-ylsulfanylmethyl]-6-methylsulfanylphenol (18e)

Using the general method B (1.5 h, 75° C.), the title compound was obtained from 1a (0.80 g; 3.0 mmol) and 8b (0.60 g; 3.0 mmol) after trituration with MeOH. M.p. 220° C. (decomposition)

IR (KBr): 1259 (OH bending), 1225 (C—F), 1007 cm$^{-1}$ (C—O)

$^1$H-NMR (DMSO-d$_6$): δ (ppm) 2.34 (s, 3H, CH$_3$), 4.38 (s, 2H, CH$_2$), 6.97 (d, 1H, 2.3 Hz, 3-Cl-Ph C$^2$—H), 7.17 (d, 1H, 2.3 Hz, 3-Cl-Ph C$^4$—H), 7.23-7.51 (m, 6H, 4-Pyr and 4-F-Ph), 8.48-8.50 (m, 2H, 4-Pyr), 12.74 (bs, 1H, exchangeable, NH), OH not visible 4-[5-(4-Fluorophenyl)-4-pyridin-4-yl-1H-imidazol-2-ylsulfanylmethyl]-2-methylsulfanylphenol (18f)

Using the general method B (2 h, room temperature), the title compound was obtained from 1a (0.20 g; 0.7 mmol) and 8c (0.14 g, 0.8 mmol) after trituration with MeOH. M.p. 230° C. (decomposition)

IR (KBr): 1227 (C—F), 1019 cm$^{-1}$ (C—O)

$^1$H-NMR (CD$_3$OD): δ (ppm) 2.21 (s, 3H, CH$_3$), 4.17 (s, 2H, CH$_2$), 6.69 (d, 1H, 8.0 Hz, 4-HO-Ph C$^3$—H), 6.90-7.01 (m, 2H, 4-HO-Ph C$^2$—/C$^6$—H), 7.12-7.21 (m, 2H, 4-F-Ph), 7.32-7.53 (m, 4H, 4-Pyr and 4-F-Ph), 8.39-8.43 (m, 2H, 4-Pyr)

2-[5-(4-Fluorophenyl)-4-pyridin-4-yl-1H-imidazol-2-ylsulfanylmethyl]-4-methanesulfinylphenol (18g)

Using the general method B (1 h, room temperature), the title compound was obtained from 1a (0.27 g; 1.0 mmol) and 8a (0.17 g; 1.0 mmol) with addition of 35% strength H$_2$O$_2$ solution after recrystallization from toluene/THF (1+1). M.p. 216° C.

IR (KBr): 1278 (OH bending), 1232 (C—F), 1031 (S=O), 1003 cm$^{-1}$ (C—O)

$^1$H-NMR (CD$_3$OD): δ (ppm) 2.60 (s, 3H, CH$_3$), 4.33 (s, 2H, CH$_2$), 6.96 (d, 1H, 8.2 Hz, 2-HO-Ph C$^3$—H), 7.11-7.21 (m, 2H, 4-F-Ph), 7.41-7.47 (m, 6H, 4-Pyr, 4-F-Ph and 2-HO-Ph C$^4$—/C$^6$—H), 8.39-8.42 (m, 2H, 4-Pyr)

4-Chloro-2-[5-(4-fluorophenyl)-4-pyridin-4-yl-1H-imidazol-2-ylsulfanylmethyl]-6-methanesulfinylphenol (18h)

Using the general method B (1.5 h, 75° C.), the title compound was obtained from 1a (0.27 g; 1.0 mmol) and 8b (0.21 g, 1.0 mmol) with addition of 35% strength H$_2$O$_2$ solution after purification by column chromatography (SiO$_2$ 60, acetone). M.p. 175° C. (decomposition)

IR (KBr): 1265 (OH bending), 1236 (C—F), 1051 (S=O), 1005 cm$^{-1}$ (C—O)

$^1$H-NMR (CD$_3$OD): δ (ppm) 2.72 (s, 3H, CH$_3$), 4.39 (s, 2H, CH$_2$), 7.14-7.23 (m, 2H, 4-F-Ph), 7.39 (d, 1H, 2.6 Hz, 3-Cl-Ph C$^2$—H), 7.42-7.49 (m, 6H, 4-Pyr, 4-F-Ph and 3-Cl-Ph C$^4$—H), 8.43-8.46 (m, 2H, 4-Pyr)

EXAMPLE 19

4-[5-(4-Fluorophenyl)-4-pyridin-4-yl-1H-imidazol-2-ylsulfanylmethyl]-2-methanesulfinylphenol (19)

Using the general method B (2.5 h, room temperature), the title compound was obtained from 1a (0.20 g; 0.7 mmol) and 8c (0.14 g, 0.8 mmol) with addition of 35% strength H$_2$O$_2$ solution after trituration with acetone.

M.p. 185° C. (decomposition)

IR (KBr): 1296 (OH bending), 1230 (C—F), 1062 (S=O), 1013 cm$^{-1}$ (C—O)

$^1$H-NMR (CD$_3$OD): δ (ppm) 2.70 (s, 3H, CH$_3$), 4.28 (s, 2H, CH$_2$), 6.78 (d, 1H, 8.3 Hz, 4-HO-Ph C$^3$—H), 7.12-7.21 (m, 2H, 4-F-Ph), 7.28 (dd, 1H, 2.2/8.3 Hz, 4-HO-Ph C$^2$—H), 7.39-7.46 (m, 5H, 4-Pyr, 4-F-Ph and 4-HO-Ph C$^6$-H), 8.40 (m, 2H, 4-Pyr)

EXAMPLE 20

4-Fluoro-N-methoxy-N-methylbenzamide (20)

A suspension of 4-fluorobenzoic acid (20 g, 143 mmol) in thionyl chloride (130 g; 1.1 mol) was stirred under reflux for 6 h: vigorous evolution of gas, clear solution after about 10 min, deepening of the color from yellow to orange. Excess thionyl chloride was removed by distillation (initially atmospheric pressure/40° C., then membrane pump vacuum/400° C.). From the distillation residue, 4-fluorobenzoyl chloride was distilled off under membrane pump vacuum at 90° C. over a short column. The reaction product crystallized on storing in a fridge (n$^{20}$D 1.5315; m.p. 9° C., yield 20 g/89%). Freshly distilled triethylamine (29 ml) was added to a suspension of N,O-dimethylhydroxylamine hydrochloride (9.0 g; 92 mmol) in CH$_2$Cl$_2$ (75 ml). The reaction mixture was stirred at room temperature for 2 h and then cooled to −10° C. With cooling, 4-fluorobenzoyl chloride (13.5 g; 85 mmol) was, over a period of 6 min, added dropwise to the initial charge. After the addition had ended, cooling was removed and the reaction mixture was stirred at room temperature for 1.5 h. The light-brown suspension was poured into H$_2$O (100 ml). The organic phase was removed and the aqueous phase was extracted with diethyl ether (2×). The combined extract was washed with saturated NaCl solution, dried over Na$_2$SO$_4$ and concentrated. The oily brown residue crystallized on cooling and scratching. The crude product was dried using an oil pump (residual triethylamine!) and reacted without further purification.

$^1$H-NMR (CDCl$_3$): δ (ppm) 3.37 (s, 3H, NCH$_3$), 3.54 (s, 3H, OCH$_3$), 7.04-7.13 (m, 2H, 4-F-Ph), 7.71-7.78 (m, 2H, 4-F-Ph)

EXAMPLE 21

2-(2-Chloropyridin-4-yl)-1-(4-fluorophenyl)ethanone (21a)

n-BuLi (15% strength solution in n-hexane, 45 ml, 104 mmol) was added dropwise to a solution, cooled to −85° C., of diisopropylamine (15 ml, 106 mmol) in abs. THF (150 ml) in a double-necked flask which had been dried by heating and flushed with argon: temperature increase to −50° C. After the addition had ended, the light-yellow solution was stirred at −85° C for 55 min. At −85° C., a solution of 2-chloro-4-methylpyridine (2-chloro-γ-picoline, 8.6 g; 68 mmol) in abs. THF (75 ml) was added dropwise to this initial charge: temperature increase to −50° C., initial change of color to purple. After the addition had ended, the reaction mixture was stirred at −85° C. for 1 h, and a solution of 20 (12.4 g; 68 mmol) in abs. THF (75 ml) was added at this temperature over a period of 3 min: temperature increase to −60° C. The purple slurry of the reaction mixture was stirred at −85° C. for 1 h and then, over a period of 1 h, warmed to 0° C. The mixture was poured into saturated NaCl solution (300 ml) which had been covered with ethyl acetate (300 ml). The organic phase was removed and the aqueous phase was extracted with ethyl acetate (2×250 ml) and a little brown foamy precipitate of 1,3-bis-(2-chloropyridin-4-yl)-2-(4-fluorophenyl)propan-2-ol separated off at the interface. The combined organic extract was washed with saturated NaCl solution, dried over NaSO$_4$ and concentrated. The oily residue was taken up in a little tert-butyl methyl ether and stored at 4° C. overnight. The crystals were filtered off and dried.

$^1$H-NMR (CDCl$_3$): δ (ppm) 4.26 (s, 2H, CH$_2$), 7.11-7.26 (m, 4H, C$^3$—/C$^5$—H 2-Cl-Pyr and 4-F-Ph), 7.99-8.06 (m, 2H, 4-F-Ph), 8.35 (dd, 1H, 0.6/5.1 Hz, C$^6$—H 2-Cl-Pyr)

1-(4-Fluorophenyl)-2-(2-fluoropyridin-4-yl)ethanone (21b)

21b was prepared from 2-fluoro-4-methylpyridine (13.9 g; 125 mmol) using the method described in the synthesis of 21a.

$^1$H-NMR (CDCl$_3$): δ (ppm) 4.32 (s, 2H, CH$_2$), 6.85-6.86 (m, 1H, C$^3$—H 2-F-Pyr), 7.08-7.19 (m, 3H, C$^5$—H 2-F-Pyr and 4-F-Ph), 8.00-8.07 (m, 2H, 4-F-Ph), 8.18 (d, 1H, 5.1 Hz, C$^6$—H 2-F-Pyr)

2-(2-Bromopyridin-4-yl)-1-(4-fluorophenyl)ethanone (21c)

21c was prepared from 2-bromo-4-methylpyridine (9.6 g; 56 mmol) using the method described in the synthesis of 21a.

$^1$H-NMR (CDCl$_3$): δ (ppm) 4.35 (s, 2H, CH$_2$), 7.17-7.37 (m, 3H, 2-Br-Pyr and 4-F-Ph) 7.50 (s, 1H, C$^3$—H 2-Br-Pyr), 8.07-8.15 (m, 2H, 4-F-Ph), 8.42 (d, 1H, 5.1 Hz, C$^6$—H 2-Br-Pyr)

EXAMPLE 22

1-(2-Chloropyridin-4-yl)-2-(4-fluorophenyl)ethane-1,2-dione-1-oxime (22a)

With stirring and cooling in a water bath (about 10° C.), a solution of NaNO$_2$ (0.85 g; 12.3 mmol) in H$_2$O (10 ml) was added dropwise over a period of 2.5 min to a solution of 21a (3.0 g; 12 mmol) in glacial acetic acid. After the addition had ended, the reaction mixture was stirred at room temperature for 0.5 h, H$_2$O (60 ml) was added and stirring at room temperature was continued for 3 h. The light-beige precipitate was filtered off, washed with water and dried under reduced pressure over CaCl$_2$.

$^1$H-NMR (DMSO-d$_6$): δ (ppm) 7.34-7.52 (m, 4H, C$^3$—/C$^5$—H 2-Cl-Pyr and 4-F-Ph), 7.93-8.00 (m, 2H, 4-F-Ph), 8.47 (d, 1H, 5.2 Hz, C$^6$—H 2-Cl-Pyr), 12.71 (bs, 1H, exchangeable, OH)

1-(2-Fluoropyridin-4-yl)-2-(4-fluorophenyl)ethane-1,2-dione-1-oxime (22b)

22b was prepared from 21b (10.0 g; 43 mmol) using the method described in the synthesis of 22a.

$^1$H-NMR (DMSO-d$_6$): δ (ppm) 7.19-7.20 (m, 1H, C$^3$—H 2-F-Pyr), 7.35-7.47 (m, 3H, C$^5$—H 2-F-Pyr and 4-F-Ph), 7.91-7.98 (m, 2H, 4-F-Ph), 8.29 (d, 1H, 5.3 Hz, C$^6$—H 2-F-Pyr), 12.69 (s, 1H, exchangeable, OH)

1-(4-Fluorophenyl)-2-(2-isopropoxypyridin-4-yl)ethane-1,2-dione-2-oxime (22c)

A solution of 22b (200 mg; 0.76 mmol) in HCl-saturated isopropanol (15 ml) was stirred under reflux for 2.5 h. The solution was concentrated and the yellowish-white residue was triturated with a little ethanol, filtered off and dried.

$^1$H-NMR (DMSO-d$_6$): δ (ppm) 1.24 (d, 6H, 6.2 Hz, 2×CH$_3$), 5.15-5.27 (m, 1H, Me-thin-H), 6.54 (s, 1H, C$^3$—H 2-iso-O-Pyr), 7.08 (dd, 1H, 1.2/5.3 Hz, C$^5$—H 2-iso-O-Pyr), 7.36-7.49 (m, 2H, 4-F-Ph), 7.88-7.97 (m, 2H, 4-F-Ph), 8.19 (d, 1H, 5.4 Hz, C$^6$—H 2-iso-O-Pyr), 12.44 (bs, 1H, exchangeable, OH)

1-(2-Bromopyridin-4-yl)-2-(4-fluorophenyl)ethane-1,2-dione-1-oxime (22d)

22d was prepared from 21c (5.0 g; 17 mmol) using the method described in the synthesis of 22a.

$^1$H-NMR (DMSO-d$_6$): δ (ppm) 7.40-7.48 (m, 3H, C$^3$—H 2-Br-Pyr and 4-F-Ph), 7.65 (d, 1H, 0.8 Hz, C$^5$—H 2-Br-Pyr), 7.93-8.01 (m, 2H, 4-F-Ph), 8.45 (d, 1H, 5.2 Hz, C$^6$—H 2-Br-Pyr), 12.72 (bs, 1H, exchangeable, OH)

EXAMPLE 23

2-Amino-2-(2-chloropyridin-4-yl)-1-(4-fluorophenyl)ethanone hydrochloride (23a)

With gentle heating, 22a (1.5 g; 5.4 mmol) was dissolved in methanol (15 ml). The solution was cooled to room temperature, HCl-containing methanol (20 ml) was added and the mixture was transferred into a two-necked flask. Pd—C 10% (150 mg) was introduced into the initial charge. The reaction vessel was evacuated using an oil pump, and H$_2$ was then introduced via a gas inlet capillary (4×). At room temperature, the suspension was shaken in a closed three-necked flask under an atmosphere of H$_2$ (240 strokes/min) until no more starting material could be detected by thin-layer chromatography (6 h). The suspension was filtered and the catalyst was washed with plenty of methanol. The combined filtrate was concentrated and the mustard-colored solid-amorphous residue was dried using an oil pump. The crude product was used without further purification for the next reaction step.

$^1$H-NMR (DMSO-d$_6$): δ (ppm) 6.53 (bs, 1H, methyne-H), 7.35-7.45 (m, 2H, 4-F-Ph), 7.59 (dd, 1H, 1.5/5.2 Hz, C$^5$—H 2-Cl-Pyr), 7.85 (d, 1H, 0.9 Hz, C$^3$—H 2-Cl-Pyr), 8.17-8.25 (m, 2H, 4-F-Ph), 8.49 (d, 1H, 4.9 Hz, C$^6$—H 2-Cl-Pyr), 9.33 (bs, 3H, exchangeable, NH$_3^+$)

2-Amino-2-(2-fluoropyridin-4-yl)-1-(4-fluorophenyl)ethanone hydrochloride (23b)

With gentle heating, 22b (5.0 g; 19 mmol) was dissolved in HCl-containing isopropanol (IsOH/HCl-saturated IsOH 1+1, 60 ml). The yellowish solution was cooled to room temperature and transferred into a two-necked flask (100 ml). Pd—C 10% (1.5 g) was introduced into the initial charge. The reaction vessel was evacuated using an oil pump and H$_2$ was then introduced via a gas inlet capillary (4×). At room temperature, the suspension was shaken in a closed three-necked flask under an atmosphere of H$_2$ (240 strokes/min) until no more starting material could be detected by thin-layer chromatography (6.5 h). The catalyst was filtered off. The filtration residue was washed with plenty of methanol (about 800 ml). The combined filtrates were concentrated and the solid-amorphous residue was dried on an oil pump. The crude product was used without further purification for the next reaction step.

$^1$H-NMR (DMSO-d$_6$): δ (ppm) 6.58 (bs, 1H, methyne-H), 7.33-7.41 (m, 2H, 4-F-Ph), 7.54 (m, 2H, C$^3$—/C$^5$—H 2-F-Pyr), 8.14-8.25 (m, 2H, 4-F-Ph), 8.30 (d, 1H, 5.5 Hz, C$^6$—H 2-F-Pyr), 9.40 (bs, 3H, exchangeable, NH$_3^+$)

2-Amino-1-(4-fluorophenyl)-2-(2-isopropoxypyridin-4-yl)ethanone hydrochloride (23c)

23c was prepared from 22c (2.0 g; 7.6 mmol) using the method described in the synthesis of 23a.

$^1$H-NMR (DMSO-d$_6$): δ (ppm) 1.23 (d, 6H, 5.6 Hz, 2×CH$_3$), 5.09-5.22 (m, 1H, methyne-H CH(CH$_3$)$_2$), 6.38-6.41 (bs, 1H, methyne-H CH—NH$_3^+$), 7.00-7.08 (m, 2H, 2-iso-O-Pyr), 7.33-7.46 (m, 2H, 4-F-Ph), 8.14-8.23 (m, 3H, 2-iso-O-Pyr and 4-F-Ph), 9.21 (bs, 3H, exchangeable, NH$_3^+$)

2-Amino-1-(4-fluorophenyl)-2-(2-methoxypyridin-4-yl)ethanone hydrochloride (23d)

23d was formed by treating 22b (7.5 g; 29 mmol) under the conditions described in the synthesis of 23a.

$^1$H-NMR (DMSO-d$_6$): δ (ppm) 3.83 (s, 3H, CH$_3$), 6.44 (bs, 1H, methyne-H), 7.13-7.16 (m, 2H, C$^3$—/C$^5$—H 2-MeO-Pyr), 7.34-7.46 (m, 2H, 4-F-Ph), 8.16-8.25 (m, 3H, C$^6$—H 2-MeO-Pyr and 4-F-Ph), 9.29 (bs, 3H, exchangeable, NH$_3^+$)

2-Amino-1-(4-fluorophenyl)-2-pyridin-4-ylethanone hydrochloride (23e)

23e was formed by treating 22c (4.0 g; 12.4 mmol) under the conditions described in the synthesis of 23b.

$^1$H-NMR (DMSO-d$_6$): δ (ppm) 6.78 (bs, 1H, methyne-H), 7.32-7.38 (m, 2H, 4-F-Ph), 8.07-8.13 (m, 2H, 4-Pyr), 8.17-8.27 (m, 2H, 4-F-Ph), 8.92-8.95 (m, 2H, 4-Pyr), 9.43 (bs, 3H, exchangeable, NH$_3^+$)

2-Amino-2-(2-bromopyridin-4-yl)-1-(4-fluorophenyl)ethanone hydrochloride (23f)

A solution of 22d (1.8 g; 5.6 mmol) in absolute ethanol (30 ml) was cooled to −10° C., and concentrated sulfuric acid (1.3 ml) was added. With cooling, zinc dust (1.1 g) was added a little at a time to the initial charge. The reaction mixture was stirred at −10° C. for 30 min and then warmed to room temperature. The gray-green suspension was filtered and the white residue ($ZnSO_4$) was washed with plenty of ethanol. The combined yellow filtrate was concentrated and the solid yellowish residue was dried using an oil pump.

$^1$H-NMR (DMSO-$d_6$): δ (ppm) 6.39 (bs, 1H, methyne-H), 7.35-7.44 (m, 2H, 4-F-Ph), 7.56 (dd, 1H, 1.4/5.1 Hz, $C^5$—H 2-Br-Pyr), 7.91 (s, 1H, $C^3$—H2-Br-Pyr), 8.12-8.19 (m, 2H, 4-F-Ph), 8.46 (d, 1H, 5.1 Hz, $C^6$—H2-Br-Pyr), 8.94 (bs, 3H, exchangeable, $NH_3^+$)

EXAMPLE 24

4-(2-Chloropyridin-4-yl)-5-(4-fluorophenyl)-1,3-dihydroimidazole-2-thione (24a)

With gentle heating, 23a (2.9 g; about 9.6 mmol) was dissolved in absolute DMF (75 ml). Potassium thiocyanate (1.9 g; 19.6 mmol) was introduced into the clear orange-red solution: immediate opalescence and a lighter color. The reaction mixture was stirred under reflux for 1.5 h. The suspension was cooled to room temperature and, with $H_2O$ cooling, diluted dropwise with $H_2O$ (about 140 ml). The yellow precipitate was filtered off, washed with $H_2O$ and dried under reduced pressure over $CaCl_2$.

$^1$H-NMR (DMSO-$d_6$): δ (ppm) 7.12-7.52 (m, 6H, $C^3$—/$C^5$—H 2-Cl-Pyr and 4-F-Ph), 8.27 (d, 1H, 5.2 Hz, $C^6$—H 2-Cl-Pyr), 12.82 (bs, 2H, exchangeable, 2×NH)

4-(4-Fluorophenyl)-5-(2-fluoropyridin-4-yl)-1,3-dihydroimidazole-2-thione (24b)

24b was prepared from 23b (6.1 g; 20 mmol) using the method described in the synthesis of 24a.

$^1$H-NMR (DMSO-$d_6$): δ (ppm) 7.12-7.16 (m, 2H, $C^3$—/$C^5$—H 2-F-Pyr), 7.28-7.27 (m, 2H, 4-F-Ph), 7.46-7.55 (m, 2H, 4-F-Ph), 8.13 (d, 1H, 5.1 Hz, $C^6$—H 2-F-Pyr), 12.85 (bs, 2H, exchangeable, 2×NH)

4-(4-Fluorophenyl)-5-(2-isopropoxypyridin-4-yl)-1,3-dihydroimidazole-2-thione (24c)

24c was prepared from 23c (2.5 g; 7.6 mmol) using the method described in the synthesis of 24a.

$^1$H-NMR (DMSO-$d_6$): δ (ppm) 1.24 (d, 6H, 6.2 Hz, 2×$CH_3$), 5.10-5.19 (m, 1H, methyne-H), 6.69-6.76 (m, 2H, 2-iso-O-Pyr), 7.24-7.32 (m, 2H, 4-F-Ph), 7.42-7.49 (m, 2H, 4-F-Ph), 8.02 (d, 1H, 5.5 Hz, $C^6$—H 2-iso-O-Pyr), 12.68 (bs, 2H, exchangeable, 2×NH)

4-(4-Fluorophenyl)-5-(2-methoxypyridin-4-yl)-1,3-dihydroimidazole-2-thione (24d)

Potassium thiocyanate (2 g, 20.6 mmol) was introduced into a solution of 23d (3.2 g; 10.8 mmol) in 10% strength hydrochloric acid (50 ml). The reaction mixture was stirred under reflux for 30 min. The orange solution was cooled and neutralized using 10% strength $NaHCO_3$ solution. The precipitate was filtered off, washed with $H_2O$ and dried under reduced pressure over $CaCl_2$. The crude product was triturated with ethanol, and insoluble components were filtered off. On standing, 24d precipitated from the ethanolic filtrate.

$^1$H-NMR (DMSO-$d_6$): δ (ppm) 3.81 (s, 3H, $OCH_3$), 6.79-6.82 (m, 2H, $C^3$—/$C^5$—H2-MeO-Pyr), 7.26-7.50 (m, 4H, 4-F-Ph), 8.06 (d, 1H, 5.3 Hz, $C^6$—H 2-MeO-Pyr), 12.65 (bs, 2H, exchangeable, 2×NH)

EXAMPLE 25

2-Chloro-4-[5-(4-fluorophenyl)-2-methylsulfanyl-3H-imidazol-4-yl]pyridine (25a)

Using the general method A, the title compound was obtained from 24a (0.5 g; 1.6 mmol) and methyl iodide (0.35 g; 2.5 mmol) after a reaction time of 12 hours and purification by column chromatography ($Al_2O_3$, $CH_2Cl_2$/ethyl acetate 1+1). M.p. 236° C.

IR (ATR): 3126, 3057, 2929, 1591, 1529, 1499, 1389, 1231 (C—F), 1159, 996, 976, 844, 780 cm$^{-1}$ $^1$H-NMR (DMSO-$d_6$): δ (ppm) 2.62 (s, 1H, $CH_3$), 7.27-7.36 (m, 3H, 2-Cl-Pyr and 4-F-Ph), 7.45-7.55 (m, 3H, 2-Cl-Pyr and 4-F-Ph), 8.24 (d, 1H, 5.1 Hz, $C^6$—H 2-Cl-Pyr), 12.85 (bs, 1H, exchangeable, NH)

2-Fluoro-4-[5-(4-fluorophenyl)-2-methylsulfanyl-3H-imidazol-4-yl]pyridine (25b)

Using the general method A, the title compound was obtained from 24b (0.95 g; 3.3 mmol) and methyl iodide (1.4 g; 9.9 mmol) after a reaction time of 40 hours. The crude product was boiled with $CH_2Cl_2$/ethyl acetate (1+1). The combined organic extract was decolorized using $Al_2O_3$, and the residue obtained after concentration of the filtrate was triturated with a little EtOH. M.p. 224° C.

IR (ATR): 3073, 1609, 1497, 1421, 1234, 1219 (C—F), 1159, 1002, 883, 851, 833, 815 cm$^{-1}$ $^1$H-NMR (DMSO-$d_6$): δ (ppm) 2.62 (s, 3H, $CH_3$), 7.08 (s, 1H, $C^3$—H 2-F-Pyr), 7.26-7.35 (m, 3H, $C^5$—H 2-F-Pyr and 4-F-Ph), 7.46-7.54 (m, 2H, 4-F-Ph), 8.08 (d, 1H, 5.3 Hz, $C^6$—H 2-F-Pyr), 12.85 (bs, 1H, exchangeable, NH)

4-[5-(4-Fluorophenyl)-2-methylsulfanyl-3H-imidazol-4-yl]-2-isopropoxypyridin (25c)

NaH (55-65%; 1.0 g; about 23 mmol) was introduced into a solution of 24c (4.0 g; 13.8 mmol) in absolute THF (60 ml). This initial charge was stirred at room temperature for 5 min, and a solution of methyl iodide (2.2 g; 17.3 mmol) in absolute THF (5 ml) was added dropwise with $H_2O$ cooling. The reaction mixture was stirred at room temperature for 1 h. The clear brown solution was concentrated and the residue was taken up in $H_2O$. The aqueous solution was neutralized using 10% strength hydrochloric acid and extracted with ethyl acetate (2×). The combined organic extract was washed with saturated NaCl solution, dried over $Na_2SO_4$ and concentrated. The semi-solid residue was extracted by boiling with tert-butyl methyl ether (2×) and filtered. The clear ethereal filtrate was concentrated and the solid residue was triturated with a little tert-butyl methyl ether, filtered off and dried. Further reaction product was obtained by column chromatographic separation of the mother liquor ($SiO_2$ 60, $CH_2Cl_2$/ethyl acetate 1+1). M.p. 141° C.

IR (ATR): 2928, 1610, 1544, 1509, 1412, 1314, 1222 (C—F), 1104, 1005, 954, 865, 843, 816 cm$^{-1}$ $^1$H-NMR ($CD_3OD$): δ (ppm) 1.28 (d, 6H, 6.1 Hz, 2×$CH_3$), 2.63 (s, 3H, $SCH_3$), 5.08-5.14 (m, 1H, methyne-H), 6.76 (s, 1H, $C^3$—H 2-iso-O-Pyr), 6.88 (dd, 1H, 1.4/5.4 Hz, $C^5$—H 2-iso-O-Pyr), 7.10-7.19 (m, 2H, 4-F-Ph), 7.40-7.47 (m, 2H, 4-F-Ph), 7.95 (dd, 1H, 0.7/5.4 Hz, $C^6$—H 2-iso-O-Pyr)

4-[5-(4-Fluorophenyl)-2-methylsulfanyl-3H-imidazol-4-yl]-2-methoxypyridine (25d)

A solution of 24d (1.0 g; 3.3 mmol) and methyl iodide (5.6 g; 39 mmol) in methanol (50 ml) was stirred under reflux for 3 h. The reaction mixture was cooled and filtered. The filtrate was concentrated and the residue was taken up in ethanol. Insoluble components were filtered off and the filtrate was concentrated. The residue was taken up in $CH_2Cl_2$/EtOH (9+1). Insoluble components were filtered off, and the filtrate was separated by column chromatography (SiO₂ 60, CH₂Cl₂/EtOH 9+1). M.p. 158° C.

IR (ATR): 1618, 1608, 1497, 1391, 1222 (C—F), 1212, 1036, 835, 825 cm⁻¹

¹H-NMR (CD₃OD): δ (ppm) 2.67 (s, 3H, SCH₃), 3.90 (s, 3H, OCH₃), 6.87-6.89 (m, 1H, C³—H 2-MeO-Pyr), 6.98 (dd, 1H, 1.5/5.5 Hz, C⁵-H2-MeO-Pyr), 7.16-7.24 (m, 2H, 4-F-Ph), 7.46-7.53 (m, 2H, 4-F-Ph), 8.03 (dd, 1H, 0.7/5.5 Hz, C⁶—H 2-MeO-Pyr)

4-[5-(4-Fluorophenyl)-2-methylsulfanyl-3H-imidazol-4-yl]-1H-pyridin-2-one (25e)

When 23d (8.8 g; 31 mmol) was treated with potassium thiocyanate in boiling DMF analogously to the method described for 24a, the only reaction product obtained was 25e. M.p. 314° C. (decomposition). After cyclization, giving the 1,3-dihydroimidazolethione, the methyl group from the methoxy substituent is transferred to the nucleophilic sulfur atom of the thione, with formation firstly of the 2-methylsulfanyl-3H-imidazole and, secondly, the 2-hydroxypyridine/1H-pyridin-2-one.

IR (ATR): 1634 (pyridone I), 1610, 1557 (pyridone II), 1493, 1220 (C—F), 968, 837, 800 cm⁻¹

¹H-NMR (DMSO-d₆): δ (ppm) 2.61 (s, 3H, SCH₃), 6.16 (bs, 1H, C³—H pyridone), 6.34 (s, 1H, C⁵—H pyridone), 7.25-7.33 (m, 3H, C⁶—H pyridone and 4-F-Ph), 7.46-7.53 (m, 2H, 4-F-Ph), 11.38 (bs, 1H, exchangeable, pyridone-NH), 12.71 (bs, 1H, exchangeable, imidazole-NH)

Benzyl{4-[S-(4-fluorophenyl)-2-methylsulfanyl-3H-imidazol-4-yl]pyridin-2-yl}-amine (25f)

Using the general method C, the title compound was obtained from 25b (0.2 g; 0.7 mmol) and benzylamine (0.8 g; 7.5 mmol) after a reaction time of 5 hours at 160° C. and separation by column chromatography (Al₂O₃, CH₂Cl₂/ethyl acetate 1+1).

M.p. 152° C. (decomposition)

IR (ATR): 3234 (NH), 3006, 2916, 1601, 1583, 1501, 1451, 1432, 1353, 1225 (C—F), 1074, 844, 813, 729, 695 cm⁻¹

¹H-NMR (CD₃OD): δ (ppm) 2.59 (s, 3H, CH₃), 4.37 (s, 2H, CH₂), 6.56-6.59 (m, 2H, C³—/C⁵—H 2-amino-Pyr), 7.04-7.44 (m, 9H, Ph and 4-F-Ph), 7.83 (d, 1H, 5.6 Hz, C⁶—H 2-amino-Pyr)

{4-[5-(4-Fluorophenyl)-2-methylsulfanyl-3H-imidazol-4-yl]pyridin-2-yl}-(4-methoxybenzyl)amine (25g)

Using the general method C, the title compound was obtained from 25b (0.44 g; 1.5 mmol) and 4-methoxybenzylamine (2.0 g; 14.6 mmol) after a reaction time of 7 hours at 160° C. and separation by column chromatography (SiO₂, CH₂Cl₂/EtOH 9+1).

M.p. 207° C.

IR (ATR): 1598, 1558, 1510, 1244, 1217 (C—F), 846, 812 cm⁻¹

¹H-NMR (CD₃OD): δ (ppm) 2.61 (s, 3H, SCH₃), 3.75 (s, 3H, OCH₃), 4.30 (s, 2H, CH₂), 6.56-6.59 (m, 2H, C³—/C⁵—H 2-amino-Pyr), 6.81-7.30 (m, 6H, 4-MeO-Ph and 4-F-Ph), 7.39-7.46 (m, 2H, 4-F-Ph), 7.84 (d, 1H, 6.0 Hz, C⁶—H 2-amino-Pyr)

{4-[5-(4-Fluorophenyl)-2-methylsulfanyl-3H-imidazol-4-yl]pyridin-2-yl}-(4-methylbenzyl)amine (25h)

Using the general method C, the title compound was obtained from 25b (0.2 g; 0.7 mmol) and 4-methylbenzylamine (0.85 g; 7.0 mmol) after a reaction time of 6 hours at 160° C. and separation by column chromatography (SiO₂ 60, CH₂Cl₂/EtOH 9+1). M.p.185° C.

IR (ATR): 1600, 1559, 1502, 1427, 1218 (C—F), 844, 809 cm⁻¹

¹H-NMR (CD₃OD): δ (ppm) 2.29 (s, 3H, CH3), 2.60 (s, 3H, SCH3), 4.32 (s, 2H, CH2), 6.57-6.60 (m, 2H, C3-/C5-H 2-amino-Pyr), 7.05-7.50 (m, 8H, 4-Me-Ph and 4-F-Ph), 7.83 (d, 1H, 5.3 Hz, C6-H2-amino-Pyr)

(4-Chlorobenzyl)-{4-[5-(4-fluorophenyl)-2-methylsulfanyl-3H-imidazol-4-yl]-pyridin-2-yl}amine (25i)

Using the general method C, the title compound was obtained from 25b (0.2 g; 0.7 mmol) and 4-chlorobenzylamine (1.0 g; 7.0 mmol) after a reaction time of 5.5 hours under reflux and separation by column chromatography (SiO₂ 60, CH₂Cl₂/EtOH 9+1). M.p. 195° C.

IR (ATR): 3409, 1597, 1549, 1502, 1489, 1422, 1218 (C—F), 843, 814, 793 cm⁻¹

¹H-NMR (CD₃OD): δ (ppm) 2.60 (s, 3H, SCH₃), 4.38 (s, 2H, CH₂), 6.57-6.60 (m, 2H, C³—/C⁵—H 2-amino-Pyr), 7.05-7.14 (m, 2H, 4-F-Ph), 7.22-7.30 (m, 4H, 4-Cl-Ph), 7.38-7.45 (m, 2H, 4-F-Ph), 7.83 (d, 1H, 5.7 Hz, C⁶—H 2-amino-Pyr)

(3,4-Dichlorobenzyl)-{4-[5-(4-fluorophenyl)-2-methylsulfanyl-3H-imidazol4-yl]-pyridin-2-yl}amine (25j)

Using the general method C, the title compound was obtained from 25b (0.2 g; 0.7 mmol) and 3,4-dichlorobenzylamine (1.2 g; 6.8 mmol) after a reaction time of 7.5 hours at 160° C. and separation by column chromatography (SiO₂ 60, CH₂Cl₂/EtOH 9+1). M.p. 212° C.

IR (ATR): 3409, 1600, 1552, 1509, 1490, 1424, 1225 (C—F), 842, 827, 813 cm⁻¹

¹H-NMR (CD₃OD): δ (ppm) 2.60 (s, 3H, SCH₃), 4.39 (s, 2H, CH₂), 6.56-6.62 (m, 2H, C³—/C⁵—H 2-amino-Pyr), 7.06-7.50 (m, 7H, 3,4-di-Cl-Ph and 4-F-Ph), 7.84 (d, 1H, 5.5 Hz, C⁶—H 2-amino-Pyr)

{4-[5-(4-Fluorophenyl)-2-methylsulfanyl-3H-imidazol-4-yl]pyridin-2-yl}-phenylamine (25k)

Using the general method C, the title compound was prepared from 25b (0.2 g; 0.7 mmol) and aniline (0.65 g; 7.0 mmol) after a reaction time of 6 hours under reflux and separation by column chromatography (SiO₂ 60, CH₂Cl₂/EtOH 9+1). M.p. 228° C.

IR (ATR): 3031, 1610, 1590, 1561, 1504, 1433, 1265, 1225 (C—F), 839, 827, 749, 695 cm⁻¹

¹H-NMR (DMSO-d₆): δ (ppm) 2.62 (s, 3H, CH₃), 5.95-6.13 (m, 2H, C³—/C⁵—H2-Pyr), 6.68-7.60 (m, 9H, Ph and 4-F-Ph), 7.97-8.01 (m, 1H, C⁶—H 2-Amino-Pyr), 8.99 (bs, 1H, exchangeable, anilino-NH), 12.68 (bs, 1H, exchangeable, imidazole-NH)

{4-[5-(4-Fluorophenyl)-2-methylsulfanyl-3H-imidazol4-yl]pyridin-2-yl}-phenethylamine (25l)

Using the general method C, the title compound was obtained from 25b (0.2 g; 0.7 mmol) and 2-phenylethylamine (0.85 g; 7.0 mmol) after a reaction time of 5.5 hours at 160° C. and separation by column chromatography (SiO₂ 60, CH₂Cl₂/EtOH 9+1). M.p. 99° C.

IR (ATR): 3409, 1604, 1546, 1504, 1220 (C—F), 838, 813, 698 cm⁻¹

¹H-NMR (CD₃OD): δ (ppm) 2.61 (s, 3H, SCH₃), 2.81 (t, 2H, 7.7 Hz, NCH₂), 3.41 (t, 2H, 7.7 Hz, CH₂Ph), 6.55-6.57 (m, 2H, C³—/C⁵—H 2-amino-Pyr), 7.08-7.26 (m, 7H, Ph and 4-F-Ph), 7.42-7.49 (m, 2H, 4-F-Ph), 7.82 (d, 1H, 6.1 Hz, C⁶—H 2-amino-Pyr)

(RS)-{4-[5-(4-Fluorophenyl)-2-methylsulfanyl-3H-imidazol-4-yl]pyridin-2-yl}-(1-phenylethyl)amine (25m)

Using the general method C, the title compound was obtained from 25b (0.2 g; 0.7 mmol) and (RS)-1-phenylethylamine (0.80 g; 6.6 mmol) after a reaction time of 7 hours at 160° C. and separation by column chromatography (SiO$_2$ 60, CH$_2$Cl$_2$/EtOH 9+1). M.p. 117-119° C.

IR (ATR): 2926, 1607, 1547, 1502, 1434, 1221 (C—F), 1157, 838, 814, 699 cm$^{-1}$ $^1$H-NMR (DMSO-d$_6$): δ (ppm) 1.37 (d, 3H, 5.5 Hz, CH$_3$), 2.58 (s, 3H, SCH$_3$), 4.82-5.03 (m, 1H, methyne-H), 6.39-7.74 (m, 12H, Ph, 2-amino-Pyr and 4-F-Ph), 12.57 (bs, 1H, exchangeable, NH)

(R)-{4-[5-(4-Fluorophenyl)-2-methylsulfanyl-3H-imidazol-4-yl]pyridin-2-yl}-(1-phenylethyl)amine (25n)

Using the general method C, the title compound was obtained from 25b (0.2 g; 0.7 mmol) and (R)-1-phenylethylamine (0.80 g; 6.6 mmol) after a reaction time of 7 hours at 170° C. and separation by column chromatography (SiO$_2$ 60, CH$_2$Cl$_2$/ethyl acetate 1+1). M.p. 117-119° C.

IR (ATR): 2926, 1607, 1547, 1502, 1434, 1221 (C—F), 1157, 838, 814, 699 cm$^{-1}$ $^1$H-NMR (CD$_3$OD): δ (ppm) 1.44 (d, 3H, 6.9 Hz, CH$_3$), 2.59 (s, 3H, SCH$_3$), 4.62-4.69 (m, 1H, methyne-H), 6.47-6.57 (m, 2H, C$^3$—/C$^5$—H2-amino-Pyr), 7.05-7.42 (m, 9H, Ph and 4-F-Ph), 7.80 (d, 1H, 5.5 Hz, C$^6$—H 2-amino-Pyr)

(S)-{4-[5-(4-Fluorophenyl)-2-methylsulfanyl-3H-imidazol-4-yl]pyridin-2-yl}-(1-phenylethyl)amine (25o)

Using the general method C, the title compound was obtained from 25b (0.2 g; 0.7 mmol) and (S)-1-phenylethylamine (0.80 g; 6.6 mmol) after a reaction time of 13 hours at 170° C. and separation by column chromatography (SiO$_2$ 60, CH$_2$Cl$_2$/ethyl acetate 1+1). M.p. 117-119° C.

IR (ATR): 2926, 1607, 1547, 1502, 1434, 1221 (C—F), 1157, 838, 814, 699 cm$^{-1}$ $^1$H-NMR (CD$_3$OD): δ (ppm) 1.44 (d, 3H, 6.9 Hz, CH$_3$), 2.59 (s, 3H, SCH$_3$), 4.62-4.69 (m, 1H, methyne-H), 6.47-6.57 (m, 2H, C$^3$—/C$^5$—H2-amino-Pyr), 7.05-7.42 (m, 9H, Ph and 4-F-Ph), 7.80 (dd, 1H, 0.5/5.5 Hz, C$^6$—H 2-amino-Pyr)

Benzyl-{4-[5-(4-fluorophenyl)-2-methylsulfanyl-3H-imidazol-4-yl]pyridin-2-yl}-methylamine (25p)

Using the general method C, the title compound was obtained from 25b (0.2 g; 0.7 mmol) and N-methylbenzylamine (0.85 g; 7.0 mmol) after a reaction time of 7 hours at 180° C. and two column-chromatographic separations (SiO$_2$ 60, CH$_2$Cl$_2$/ethyl acetate 1+1). M.p. 79° C.

IR (ATR): 2924, 1601, 1494, 1407, 1219 (C—F), 837, 810, 730, 696 cm$^{-1}$ $^1$H-NMR (CD$_3$OD): δ (ppm) 2.60 (s, 3H, SCH$_3$), 2.97 (s, 3H, NCH$_3$), 4.64 (s, 2H, CH$_2$) 6.64-6.66 (m, 2H, C$^3$—/C$^5$—H 2-amino-Pyr), 7.02-7.45 (m, 9H, Ph and 4-F-Ph), 7.96 (d, 1H, 5.0 Hz, C$^6$—H 2-amino-Pyr)

The compounds compiled in Table 2 below were obtained using the above method:

TABLE 2

| Ex. | Method | Name | Structure |
|-----|--------|------|-----------|
| 25q | C | (4-Fluorophenyl)-{4-[5-(4-fluorophenyl)-2-methylsulfanyl-1H-imidazol-4-yl]pyridin-2-yl}amine | 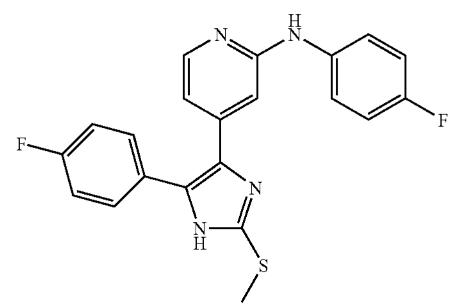 |
| 25r | C | (4-Chlorophenyl)-{4-[5-(4-fluorophenyl)-2-methylsulfanyl-1H-imidazol-4-yl]pyridin-2-yl}amine | 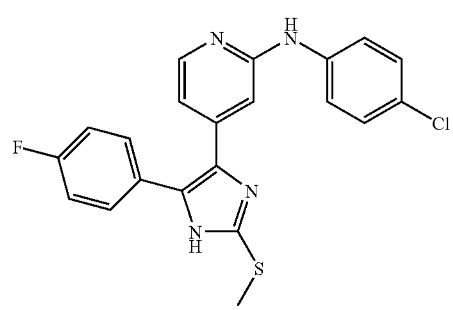 |

TABLE 2-continued

| Ex. | Method | Name | Structure |
| --- | --- | --- | --- |
| 25s | C | {4-[5-(4-Fluorophenyl)-2-methylsulfanyl-1H-imidazol-4-yl]pyridin-2-yl}-m-tolylamine | 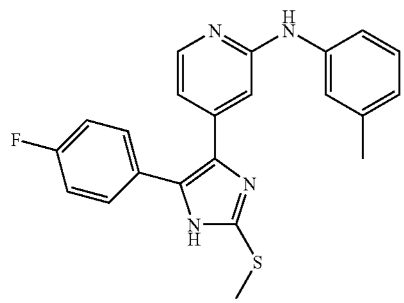 |
| 25t | C | (2,4-Difluorophenyl)-{4-[5-(4-fluorophenyl)-2-methylsulfanyl-1H-imidazol-4-yl]pyridin-2-yl}amine | 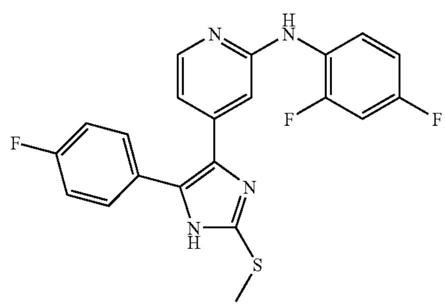 |
| 25u | C | (2,6-Dichlorophenyl)-{4-[5-(4-fluorophenyl)-2-methylsulfanyl-1H-imidazol-4-yl]pyridin-2-yl}amine | 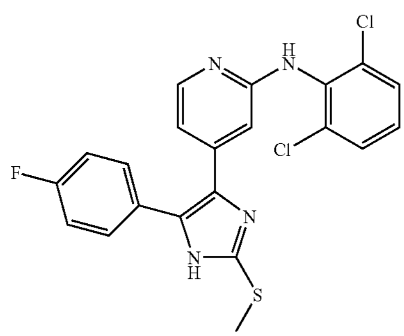 |
| 25v | C | {4-[5-(4-Fluorophenyl)-2-methylsulfanyl-1H-imidazol-4-yl]-pyridin-2-yl}-(1-phenylpropyl)amine | 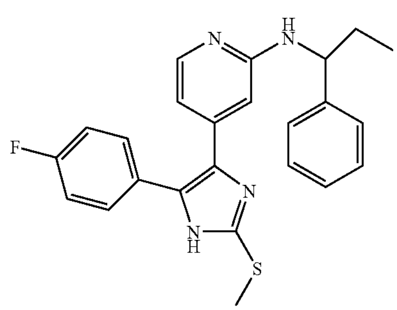 |

TABLE 2-continued

| Ex. | Method | Name | Structure |
|---|---|---|---|
| 25w | C | 3,3-Diphenylpropyl-{4-[5-(4-fluorophenyl)-2-methylsulfanyl-1H-imidazol-4-yl]pyridin-2-yl}amine | 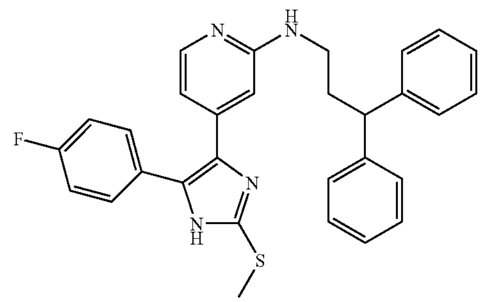 |
| 25x | C | {4-[5-(4-Fluorophenyl)-2-methylsulfanyl-1H-imidazol-4-yl]-pyridin-2-yl}naphthalen-1-yl-methylamine | 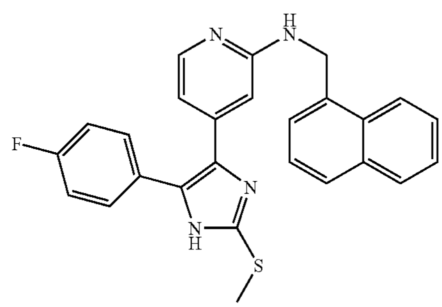 |
| 25y | C | {4-[5-(4-Fluorophenyl)-2-methylsulfanyl-1H-imidazol-4-yl]-pyridin-2-yl}naphthalen-2-yl-methylamine | 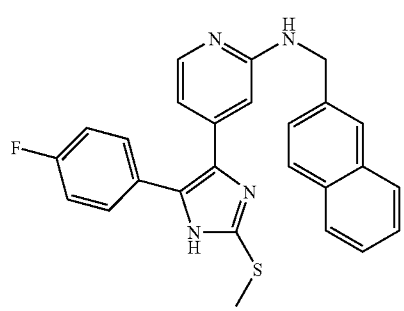 |

EXAMPLE 26

4-[2-Benzylsulfanyl-5-(4-fluorophenyl)-3H-imidazol-4-yl]-2-chloropyridine (26a)

Using the general method A, the title compound was obtained from 24a (0.3 g; 1.0 mmol) and benzyl chloride (0.12 g; 1.0 mmol) after a reaction time of 6 hours and purification by column chromatography (SiO$_2$ 60, CH$_2$Cl$_2$/EtOH 9+1). M.p. 223° C.

IR (ATR): 2939, 1591, 1530, 1505, 1233 (C—F), 997, 838, 782, 700 cm$^{-1}$ $^1$H-NMR (DMSO-d$_6$): δ (ppm) 4.43 (s, 2H, CH$_2$), 7.27-7.47 (m, 11H, 2-Cl-Pyr, Ph and 4-F-Ph), 8.26 (d, 1H, 5.2 Hz, C$^6$—H 2-Cl-Pyr), 12.94 (bs, 1H, exchangeable, NH)

4-[2-Benzylsulfanyl-5-(4-fluorophenyl)-3H-imidazol-4-yl]-2-fluoropyridine (26b)

Using the general method A, the title compound was obtained from 24b (5.1 g; 17.6 mmol) and benzyl bromide (9.2 g; 54 mmol) after a reaction time of 1.5 hours and separation by column chromatography (Al$_2$O$_3$, CH$_2$Cl$_2$/ethyl acetate 1+1). M.p. 174° C.

IR (ATR): 3028, 2948, 1611, 1496, 1413, 1228 (C—F), 1203, 1003, 879, 838, 698 cm$^{-1}$ $^1$H-NMR (DMSO-d$_6$): δ (ppm) 4.43 (s, 2H, CH$_2$), 7.11 (s, 1H, C$^3$—H 2-F-Pyr), 7.25-7.51 (m, 10H, C$^5$—H 2-F-Pyr, Ph and 4-F-Ph), 8.10 (d, 1H, 5.3 Hz, C$^6$—H 2-F-Pyr), 12.93 (bs, 1H, exchangeable, NH)

Benzyl-{4-[2-benzylsulfanyl-5-(4-fluorophenyl)-3H-imidazol-4-yl]pyridin-2-yl}-amine (26c)

Using the general method C, the title compound was obtained from 26b (0.2 g; 0.53 mmol) and benzylamine (0.60 g; 5.6 mmol) after a reaction time of 6 hours at 180° C. and separation by column chromatography (SiO$_2$ 60, CH$_2$Cl$_2$/ethyl acetate 1+1). M.p. 185° C.

IR (ATR): 3407 (NH), 3025, 2855, 2713, 1599, 1550, 1489, 1356, 1220 (C—F), 1155, 840, 814, 693 cm$^{-1}$ $^1$H-NMR (CD$_3$OD): δ (ppm) 4.21 (s, 2H, NCH$_2$), 4.38 (s, 2H, SCH$_2$), 6.52-6.55 (m, 2H, C$^3$—/C$^5$—H 2-amino-Pyr), 7.03-7.38 (m, 9H, Ph and 4-F-Ph), 7.83 (d, 1H, 5.7 Hz, C$^6$—H 2-amino-Pyr)

(RS)-{4-[2-Benzylsulfanyl-S-(4-fluorophenyl)-3H-imidazol-4-yl]pyridin-2-yl}-(1-phenylethyl)amine (26d)

Using the general method C, the title compound was obtained from 26b (0.2 g; 0.53 mmol) and (RS)-1-phenylethylamine (0.65 g; 5.4 mmol) after a reaction time of 15 hours at 150° C. and separation by column chromatography (SiO$_2$ 60, CH$_2$Cl2/ethyl acetate 1+1). M.p. 145° C.

IR (ATR): 3028, 1606, 1546, 1494, 1450, 1221 (C—F), 1157, 837, 813, 697 cm$^{-1}$ $^1$H-NMR (CD$_3$OD): δ (ppm) 1.44 (d, 3H, 6.8 Hz, CH$_3$), 4.22 (s, 2H, CH$_2$), 6.44-6.54 (m, 2H, C$^3$—/C$^5$—H 2-amino-Pyr), 7.04-7.35 (m, 9H, Ph and 4-F-Ph), 7.80 (d, 1H, 5.4 Hz, C$^6$—H 2-amino-Pyr)

{4-[2-Benzylsulfanyl-5-(4-fluorophenyl)-3H-imidazol-4-yl]pyridin-2-yl}-(4-methoxybenzyl)amine (26e)

Using the general method C, the title compound was obtained from 26a (0.2 g; 0.5 mmol) and 4-methoxybenzylamine (2.0 g; 14.6 mmol) after a reaction time of 22 hours under reflux and separation by column chromatography (Al$_2$O$_3$, CH$_2$Cl$_2$/ethyl acetate 1+1). M.p. 196-200° C.

IR (ATR): 1605, 1574, 1507, 1245, 1225 (C—F), 843, 814, 698

$^1$H-NMR (DMSO-d$_6$): δ (ppm) 4.29 (s, 2H isomers "A"+"B", NCH$_2$), 4.35 (s, 2H "A"+"B", SCH2), 6.43-6.47 (m, 1H "A"+2H "B", C$^5$—H "A" and C$^3$—/C$^5$—H "B" 2-amino-Pyr), 6.65 (s, 1H "A", C$^3$—H2-amino-Pyr), 6.80-6.84 (m, 2H "A"+"B", 4-MeO-Ph), 7.14-7.51 (m, 11H "A"+"B", 4-MeO-Ph, Ph and 4-F-Ph), 7.79 (d, 1H "B", 5.4 Hz, C$^6$—H 2-amino-Pyr), 7.91 (d, 1H "A", 5.4 Hz, C$^6$—H 2-amino-Pyr), 12.67 (bs, 1H, exchangeable, Imidazole-NH), amino-NH not visible 4-[2-Benzylsulfanyl-5-(4-fluorophenyl)-3H-imidazol-4-yl]-2-methoxypyridine (26f)

A suspension of 25a (0.1 g; 0.25 mmol) in methanolic NaOCH$_3$ solution (30%, 2 ml) was diluted with methanol (5 ml) and stirred under reflux for 13 h. The reaction mixture was diluted with H$_2$O and the aqueous solution was extracted with CH$_2$Cl$_2$ (3×). The combined organic extract was washed with saturated NaCl solution, dried over Na$_2$SO$_4$ and concentrated. The oily residue was purified by column chromatography (SiO$_2$ 60, CH$_2$Cl$_2$/ethyl acetate 1+1).

$^1$H-NMR (CDCl$_3$): δ (ppm) 3.91 (s, 3H, OCH$_3$), 4.29 (s, 2H, CH$_2$), 6.91-6.95 (m, 1H, 2-MeO-Pyr), 7.02-7.11 (m, 2H, 4-F-Ph), 7.27-7.38 (m, 7H, Ph and 4-F-Ph), 8.05 (d, 1H, 5.4 Hz, C$^6$—H 2-MeO-Pyr), NH not visible

EXAMPLE 27

2-Chloro-4-[5-(4-fluorophenyl)-2-(4-methanesulfinylbenzylsulfanyl)-3H-imidazol-4-yl]pyridine (27a)

NaH (55-65%; 0.1 g; about 2 mmol) was introduced into a solution of 24a (0.31 g; 1.0 mmol) in absolute THF (15 ml). The initial charge was stirred at room temperature for 5 min, and 4-methylsulfinylbenzyl chloride (3, 0.19 g; 1.0 mmol) was added. The reaction mixture was stirred at room temperature for 2 h. The yellow-brown solution was diluted with H$_2$O and neutralized with 10% strength citric acid. The THF was removed and the aqueous solution was extracted with ethyl acetate (2×). The combined organic extract was washed with saturated NaCl solution (2×), dried over Na$_2$SO$_4$ and concentrated. The solids residue was purified by column chromatography (SiO$_2$ 60, CH$_2$Cl$_2$/EtOH 9.5+0.5). M.p. 179° C.

IR (ATR): 3049, 1592, 1505, 1374, 1224 (C—F), 1086, 1030 (S═O), 1014, 989, 839, 816, 781 cm$^{-1}$ (C—Cl)

$^1$H-NMR (DMSO-d$_6$): δ (ppm) 2.71 (s, 3H, CH$_3$), 4.48 (s, 2H, CH$_2$), 7.25-8.24 (m, 10H, 2-Cl-Pyr, 4-MeS(O)-Ph and 4-F-Ph), 8.26 (d, 1H, 5.3 Hz, C$^6$—H 2-Cl-Pyr), 12.94 (bs, 1H, exchangeable, NH)

2-Fluoro-4-[5-(4-fluorophenyl)-2-(4-methanesulfinylbenzylsulfanyl)-3H-imidazol-4-yl]pyridine (27b)

Using the general method A, the title compound was obtained from 24b (4.2 g; 14.5 mmol) and 3 (4.1 g; 22 mmol) after a reaction time of 2 hours and separation by column chromatography (1. Al$_2$O$_3$, CH$_2$Cl$_2$/ethyl acetate 1+1, 2. SiO$_2$ 60, CH$_2$Cl$_2$/EtOH 9+1). M.p. 150° C.

IR (ATR): 3061, 1610, 1506, 1408, 1227 (C—F), 1030 (S═O), 1016, 995, 978, 882, 839, 815 cm$^{-1}$ $^1$H-NMR (DMSO-d$_6$): δ (ppm) 2.71 (s, 3H, CH$_3$), 4.49 (s, 2H, CH$_2$), 7.10 (s, 1H, C$^3$—H2-F-Pyr), 7.30-7.37 (m, 3H, C$^5$—H 2-F-Pyr and 4-F-Ph), 7.47-7.67 (m, 6H, 4-F-Ph and 4-MeS(O)-Ph), 8.11 (d, 1H, 4,8 Hz, C$^6$—H 2-F-Pyr), 12.95 (bs, 1H, exchangeable, NH)

Benzyl-{4-[5-(4-fluorophenyl)-2-(4-methanesulfinylbenzylsulfanyl)-3H-imidazol-4-yl]pyridin-2-yl}amine (27c)

Using the general method C, the title compound was obtained from 27b (0.3 g; 0.68 mmol) and benzylamine (0.75 g; 7.0 mmol) after a reaction time of 7 hours at 170° C. and separation by column chromatography (SiO$_2$ 60, CH$_2$Cl$_2$/ethanol 19+1).

M.p. 149° C.

IR (ATR): 3238, 3064, 1600, 1558, 1514, 1495, 1227 (C—F), 1034 (S═O), 1006, 982, 839, 814 cm$^{-1}$ $^1$H-NMR (CD$_3$OD): δ (ppm) 2.70 (s, 3H, CH$_3$), 4.21 (s, 2H, NCH$_2$), 4.32 (s, 2H, SCH$_2$) 6.51-6.55 (m, 2H, C$^3$—/C$^5$—H 2-amino-Pyr), 7.03-7.42 (m, 13H. Ph, 4-MeS(O)-Ph and 4-F-Ph), 7.82 (d, 1H, 5.5 Hz, C$^6$—H 2-amino-Pyr)

(RS)-{4-[5-(4-Fluorophenyl)-2-(4-methanesulfinylbenzylsulfanyl)-3H-imidazol-4-yl]pyridin-2-yl}-(1-phenylethyl)amine (27d)

Using the general method C, the title compound was obtained from 27b (0.3 g; 0.68 mmol) and (RS)-1-phenylethylamine (0.85 g; 7.0 mmol) after a reaction time of 10 hours at 170° C. and separation by column chromatography (SiO$_2$ 60, CH$_2$Cl$_2$/ethanol 9+1). M.p. 193° C.

IR (ATR): 2967, 1606, 1547, 1502, 1221 (C—F), 1085, 1031 (S═O), 1014, 838, 814, 670 cm$^{-1}$ $^1$H-NMR (CD$_3$OD): δ (ppm) 1.45 (d, 3H, 6.8 Hz, CH$_3$), 2.67 (s, 3H, S(O)CH$_3$), 4.28 (s, 2H, CH$_2$), 4.62-4.73 (m, 1H, methyne-H), 6.42-6.53 (m, 2H, C$^3$—/C$^5$—H 2-amino 7.09-7.44 (m, 9H, Ph and 4-F-Ph), ), 8.21 (d, 1 H, 5.0 Hz, C$^6$—H 2-F-Pyr).

Compounds obtained by method C are compiled in Table 3 below (however, compound no. 31 was obtained by method D):

TABLE 3

¹H-NMR

[Structure: 4-(4-fluorophenyl)-2-(methylthio)-5-(2-R³-pyridin-4-yl)-1H-imidazole]

| Example No. | R³ | Solvent | ¹H-NMR spectrum δ(ppm) |
|---|---|---|---|
| 28 | CH₃NH–CH₂–(2-thienyl) | DMSO-d6 | 2.59 (s, 3H, —SCH3), 4.59 (t, 2H, J=4.74 Hz, >N—CH2—), 6.46-6.71 (m, 2H, C3-/C5-H 2-amino-Pyr), 6.91-6.94 (m, 2H, thiophene), 7.07 (t, 1H, exchangeable, J=4.7 Hz, Pyr-NH—), 7.16-7.23 (m, 1H, thiophene), 7.28-7.35 (m, 2H, 4-F-Phe), 7.41-7.50 (m, 2H, 4-F-Phe), 7.82-7.96 (m, 1H, C6-H 2-amino-Pyr), 12.61 (s, 1H, exchangeable, imidazole-NH) |
| 29 | CH₃NH–CH₂–(2-furyl) | DMSO-d6 | 2.60 (s, 3H, —SCH3), 4.41 (d, 2H, J=5.74 Hz, >N—CH2—), 6.17 (d, 1H, J=3.12 Hz, C3-H furan), 6.34-6.37 (m, 1H, C4-H furan), 6.46-6.49 (m, 1H, C5-H 2-amino-Pyr), 6.65 (s, 1H, C3-H 2-amino-Pyr), 6.95 (t, 1H, J=6.00 Hz, Pyr-NH—), 7.18-7.27 (m, 2H, 4-F-Phe), 7.44-7.55 (m, 3H, C5-H furan and 4-F-Phe), 7.88 (d, 1H, J=4.70 Hz, C6-H 2-amino-Pyr), 12.62 (s, 1H, imidazole-NH) |
| 30 | CH₃NH–CH₂–(tetrahydrofuran-2-yl) | DMSO-d6 | 1.47-1.53 (m, 1H, C3-H tetrahydrofuran), 1.75-1.88 (m, 3H, C3-/C5-H tetrahydrofuran), 2.59 (s, 3H, —SCH3), 3.20-3.28 (m, 2H, >N—CH2—), 3.55-3.61 (m, 1H, C5-H tetrahydrofuran), 3.69-3.76 (m, 1H, C5-H tetrahydrofuran), 3.89-3.93 (m, 1H, methyne-H tetrahydrofurfurylamine), 6.39–6.68 (m, 3H, C3-/C5-H 2-amino-Pyr and Pyr-NH— (1H exchangeable)), 7.15–7.31 (m, 2H, 4-F-Phe), 7.41–7.50 (m, 2H, 4-F-Phe), 7.76–7.92 (m, 1H, C6-H 2-amino-Pyr), 12.58 (s, 1H, exchangeable, imidazole-NH) |
| 31 | CH₃NH–CH₂–(2-pyridyl) | CD3OD | 2.6 (s, 3H, —SCH3), 4.54 (s, 2H, >N—CH2—), 6.60 (d, 2H, J=4.16 Hz, C3-/C5-H 2 amino-Pyr), 7.03–7.12 (m, 2H, 4-F-Phe), 7.27–7.44 (m, 4H, C3-/C5-H 2-(aminomethyl)pyridine and 4-F-Phe), 7.71–7.80 (m, 1H, C4-H 2-(aminomethyl)pyridine), 7.84 (d, 1H, J=6.04 Hz, C6-H 2-amino-Pyr), 8.43–8.46 (m, 1H, C6-H 2-(aminomethyl)pyridine) |
| 32 | CH₃NH–CH₂–(3-pyridyl) | CD3OD | 2.60 (s, 3H, —SCH3), 4.48 (s, 2H, >N—CH2—), 6.59–6.62 (m, 2H, C3-/C5-H 2-amino-Pyr), 7.06–7.14 (m, 2H, 4-F-Phe), 7.34–7.45 (m, 3H, 4-F-Phe and C5-H 3-(aminomethyl)pyridine), 7.73–7.78 (m, 1H, C4-H 3-(aminomethyl)pyridine), 7.84 (d, 1H, J=6.18 Hz, C6-H 2-amino-Pyr), 8.37–8.40 (m, 1H, C6-H 3-(aminomethyl)pyridine), 8.44–8.45 (m, 1H, C2-H 3-(aminomethyl)pyridine) |
| 33 | CH₃NH–CH₂–cyclohexyl | DMSO-d6 | 0.78–0.92 (m, 2H, cyclohexane), 1.10–1.22 (m, 3H, cyclohexane), 1.42–1.45 (m, 1H, methyne-H, cyclohexylmethylamine), 1.64–1.70 (d, 5H, J=10.49 Hz, cyclohexane), 2.59 (s, 3H, —SCH3), 2.93–3.02 (m, 2H, >N—CH2—), 6.39–6.60 (m, 3H, C3-/C5-H 2-amino-Pyr and Pyr-NH—, (1H exchangeable)), 7.12–7.31 (m, 2H, 4-F-Phe), 7.40–7.53 (m, 2H, 4-F-Phe), 7.76–7.91 (m, 1H, C6-H 2-amino-Pyr), 12.60 (s, 1H, exchangeable, imidazole-NH) |
| | | CD3OD | 0.93 (t, 2H, J=11.05 Hz, cyclohexane), 1.17–1.28 (m, 3H, cyclohexane), 1.40–1.49 (m, 1H, methyne-H, cyclohexane), 1.75 (d, 5H, J=11.47 Hz, cyclohexane), 2.62 (s, 3H, —SCH3), 2.96–2.99 (m, 2H, >NH—CH2—), 6.54 (d, 2H, J=5.10 Hz, C3-/C5-H 2-amino-Pyr), 7.14 (t, 2H, J=8.77 Hz, 4-F-Phe), 7.43–7.50 (m, 2H, 4-F-Phe), 7.80 (d, 1H, J=5.52 Hz, C6-H 2-amino-Pyr) |
| 34 | CH₃NH–(1-indanyl) | CD3OD | 1.75-1.86 (m, 1H, C3-H 1-aminoindane), 2.45-2.53 (m, 1H, C3-H 1-aminoindane), 2.61 (s, 3H, —SCH3), 2.82-32.96 (m, 2H, C2-H, 1-aminoindane), 5.25 (t, 1H, J=7.29 Hz, methyne-H 1-aminoindane), 6.56–6.59 (m, 1H, C5-H 2-amino-Pyr), 6.67 (s, 1H, C3-H 2-amino-Pyr), 7.07–7.25 (m, 6H, C4-/C5-/C6-/C7-H 1-aminoindane and 4-F-Phe), 7.42–7.49 (m, 2H, 4-F-Phe), 7.84–7.87 (m, 1H, C6-H 2-amino-Pyr) |
| 35 | CH₃NH–CH₂CH₂–(2-thienyl) | CD3OD | 2.62 (s, 3H, —SCH3), 3.04 (t, 2H, J=7.02 Hz, —CH2— 2-(2-thienyl)ethylamine)), 3.47 (t, 2H, J=7.04 Hz, >N—CH2— 2-(2-thienyl)ethylamine)), 6.56–6.59 (m, 2H, C3-/C5-H 2-amino-Pyr), 6.83–6.85 (m, 1H, C3-H thiophene), 6.89–6.94 (m, 1H, C4-H thiophene), 7.09–7.20 (m, 3H, 4-F-Phe and C5-H thiophene), 7.43–7.50 (m, 2H, 4-F-Phe), 7.84 (d, 1H, J=6.12 Hz, C6-H 2-amino-Pyr) |

TABLE 3-continued

1H-NMR

[Structure: 4-(4-fluorophenyl)-5-(2-R³-pyridin-4-yl)-2-methylsulfanyl-1H-imidazole]

| Example No. | R³ | Solvent | δ(ppm) |
|---|---|---|---|
| 36 | [N-methyl-1,2-diphenylethylamine group] | CD3OD | 2.58 (s, 3H, —SCH3), 3.00–3.03 (m, 2H, —CH2— 1,2-diphenylethylamine), 4.73 (t, 1H, J=7.20 Hz, methyne-H 1,2-diphenylethylamine), 6.40 (s, 1H, C3-H 2-amino-Pyr), 6.55 (d, 1H, J=5.44 Hz, C5-H 2-amino-Pyr), 7.05-7.40 (m, 14H, 4-F-Phe and Ar-H 1,2 diphenylethylamine), 7.77 (d, 1H, J=5.44 Hz, C6-H 2-amino-Pyr) |

EXAMPLE 37a

Cyclohexyl-{4-[5-(4-fluorophenyl)-2-methylsulfanyl-1H-imidazol-4-yl]pyridin-2-yl}amine (37a)

2-Fluoro-4-[5-(4-fluorophenyl)-2-methylsulfanyl-1H-imidazol-4-yl]pyridine (1.2 g, 4 mmol), which had been weighed out into a 25 ml one-necked flask which had been flushed with argon beforehand, was suspended in cyclohexylamine (3.97 g, 0.04 mol), covered with argon and then heated with reflux of the amine, in an oil bath at a temperature of 160° C., for 48 h. The brown suspension is allowed to cool to RT. 30 ml of Na citrate solution (10% strength citric acid solution pH 5 with conc. NaOH) are then added, and the mixture is stirred for 10 min. and extracted twice with 30 ml of ethyl acetate.

The combined organic phases are extracted twice again with in each case 30 ml of Na citrate solution (10% strength citric acid solution pH 5 with conc. NaOH) and then with 30 ml of NaHCO₃ solution and extracted once with saturated NaCl solution. The organic phase is dried over Na₂SO₄ and concentrated using a rotary evaporator, and the residue is crystallized from 10 ml.

Recrystallization is carried out from isopropanol/water (about 5 ml of ISOH are heated and allowed to cool, and about 5 ml of dist. water are added slowly). Yield: 0.76 g (49.7%) of a purity (HPLC) of 96.6%.

The compounds of the formula I compiled in Table 4 below are obtained using this method:

TABLE 4

| Ex. | Method | Name | Structure |
|---|---|---|---|
| 37b | C | 4-[5-(4-Fluorophenyl)-2-methylsulfanyl-1H-imidazol-4-yl]-2-methoxypyridine | [Structure showing imidazole with 4-fluorophenyl, ethylsulfanyl, and 2-(cyclohexylamino)pyridin-4-yl substituents] |

TABLE 4-continued

| Ex. | Method | Name | Structure |
|---|---|---|---|
| 37c | C | Cyclohexyl-{4-[5-(4-fluorophenyl)-2-isopropylsulfanyl-1H-imidazol-4-yl]pyridine-2-yl}amine | 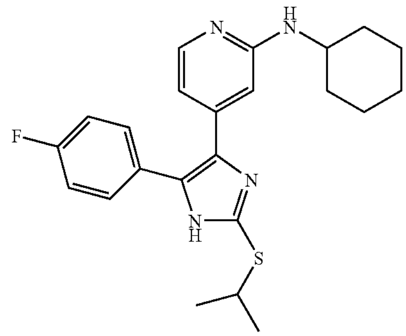 |
| 37d | C | Cyclohexyl-{4-[5-(4-fluorophenyl)-2-(2,2,2-trifluoro-ethylsulfanyl)-1H-imidazol-4-yl]pyridin-2-yl}amine | 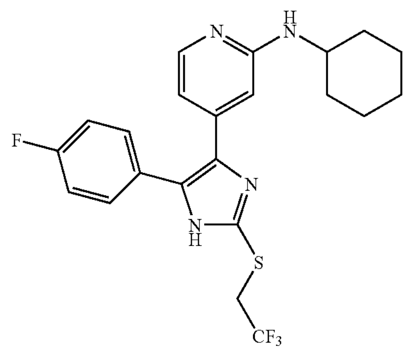 |
| 37e | C | Cyclohexyl-{4-[5-(2,4-difluorophenyl)-2-methylsulfanyl-1H-imidazol-4-yl]pyridin-2-yl}-amine | 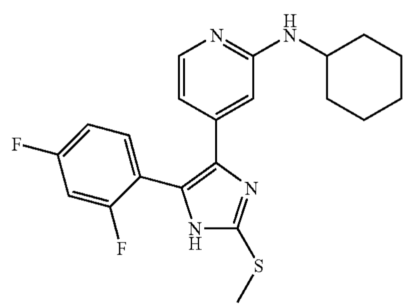 |
| 37f | C | Cyclohexyl-{4-[5-(2,4-difluorophenyl)-2-ethylsulfanyl-1H-imidazol-4-yl]pyridin-2-yl}amine | 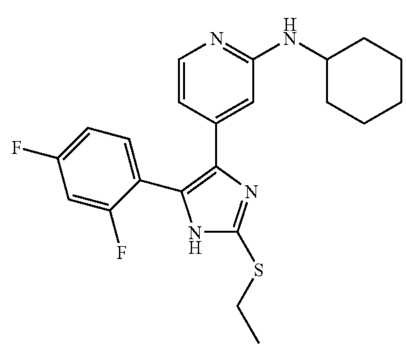 |

TABLE 4-continued

| Ex. | Method | Name |
|---|---|---|
| 37g | C | Cyclohexyl-{4-[5-(2,4-difluorophenyl)-2-isopropylsulfanyl-1H-imidazol-4-yl]pyridin-2-yl}amine |
| 37h | C | Cyclohexyl-{4-[5-(2,4-difluorophenyl)-2-(2,2,2-trifluoro-ethylsulfonyl)-1H-imidazol-4-yl]pyridin-2-yl}amine |
| 37i | C | Cyclohexyl-{4-[2-methylsulfanyl-5-(3-trifluoromethylphenyl)-1H-imidazol-4-yl]pyridin-2-yl}amine |
| 37j | C | Cyclohexyl-{4-[2-ethylsulfanyl-5-(3-trifluoromethylphenyl)-1H-imidazol-4-yl]pyridin-2-yl}amine |

The compounds compiled in Table 5 below were obtained using the above method:

TABLE 5

| Ex. | Process | Name | Structure |
|---|---|---|---|
| 38 | G | 4-[5-(4-Fluorophenyl)-2-methylsulfanyl-1H-imidazol-4-yl]-pyridin-2-ylamine | 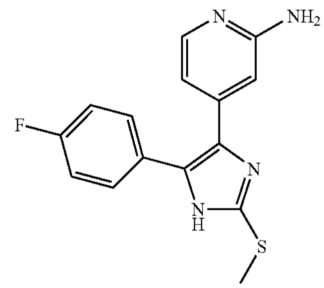 |
| 39 | C | Methyl-{4-[5-(4-fluorophenyl)-2-methylsulfanyl-1H-imidazol-4-yl]pyridin-2-yl}amine | 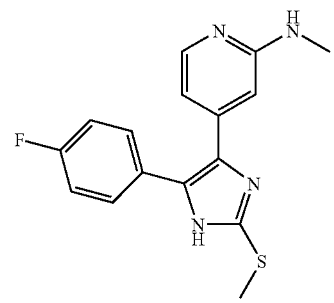 |
| 40 | C | Ethyl-{4-[5-(4-fluorophenyl)-2-methylsulfanyl-1H-imidazol-4-yl]pyridin-2-yl}amine | 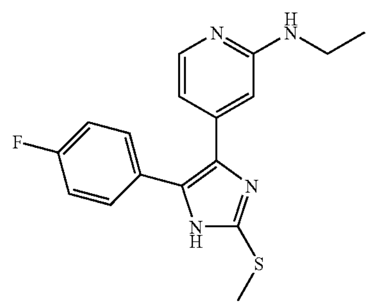 |
| 41 | C | Isopropyl-{4-[5-(4-fluorophenyl)-2-methylsulfanyl-1H-imidazol-4-yl]pyridin-2-yl}amine | 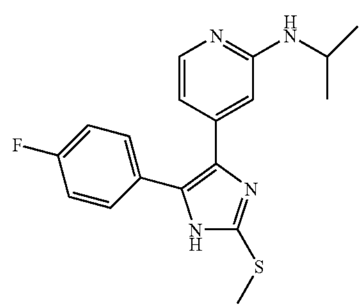 |
| 42 | C | Methoxyethyl-{4-[5-(4-fluorophenyl)-2-methylsulfanyl-1H-imidazol-4-yl]pyridin-2-yl}amine | 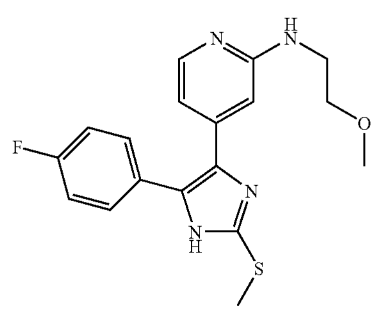 |

TABLE 5-continued

| Ex. | Process | Name | Structure |
|---|---|---|---|
| 43 | C | N,N-Dimethylaminoethyl-{4-[5-(4-fluorophenyl)-2-methylsulfanyl-1H-imidazol-4-yl]pyridin-2-yl}amine | 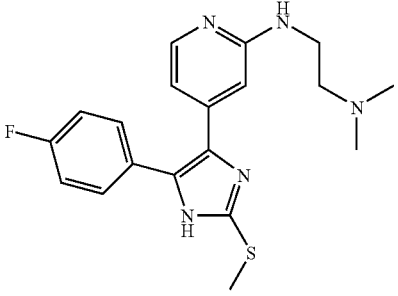 |
| 44 | C | Hydroxypropyl-{4-[5-(4-fluorophenyl)-2-methylsulfanyl-1H-imidazol-4-yl]pyridin-2-yl}amine | 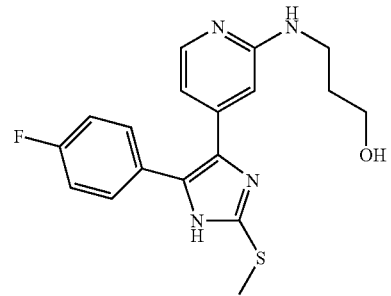 |
| 45 | C | N'-{4-[5-(4-Fluorophenyl)-2-methylsulfanyl-1H-imidazol-4-yl]pyridin-2-yl}-N,N-diphenylethane-1,2-diamine | 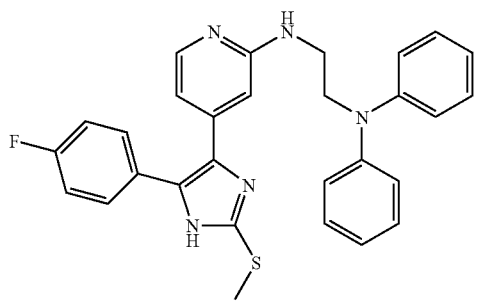 |
| 46 | H | Cinnamyl-{4-[5-(4-fluorophenyl)-2-methylsulfanyl-1H-imidazol-4-yl]pyridin-2-yl}amine | 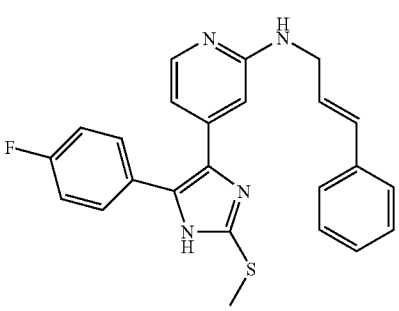 |
| 47 | C | Cyclopropyl-{4-[5-(4-fluorophenyl)-2-methylsulfanyl-1H-imidazol-4-yl]pyridin-2-yl}amine | 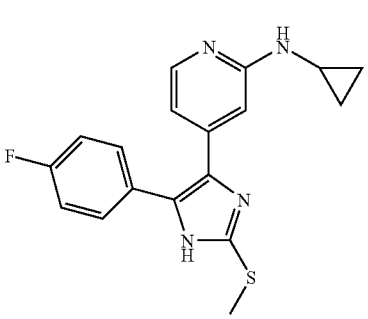 |

TABLE 5-continued

| Ex. | Process | Name |
|---|---|---|
| 48 | C | Cyclopropylmethyl-{4-[5-(4-fluorophenyl)-2-methylsulfanyl-1H-imidazol-4-yl]pyridin-2-yl}amine |
| 49 | C | Cycloheptyl-{4-[5-(4-fluorophenyl)-2-methylsulfanyl-1H-imidazol-4-yl]pyridin-2-yl}amine |
| 50 | C | Bicyclo[2.2.1]hept-2-yl-{4-[5-(4-fluorophenyl)-2-methylsulfanyl-1H-imidazol-4-yl]pyridin-2-yl}amine |
| 51 | C | Adamantan-1-yl-{4-[5-(4-fluorophenyl)-2-methylsulfanyl-1H-imidazol-4-yl]pyridin-2-yl}amine |
| 52 | C | Adamantan-2-yl-{4-[5-(4-fluorophenyl)-2-methylsulfanyl-1H-imidazol-4-yl]pyridin-2-yl}amine |

TABLE 5-continued

| Ex. | Process | Name | Structure |
|---|---|---|---|
| 53 | C | {4-[5-(4-Fluorophenyl)-2-methylsulfanyl-1H-imidazol-4-yl]-pyridin-2-yl}-(tetrahydrofuran-3-yl)-amine | 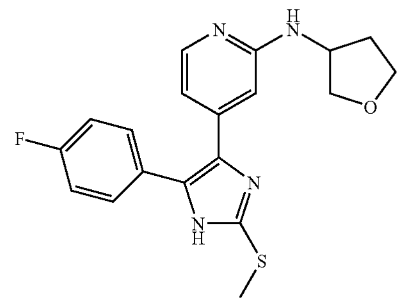 |
| 54 | H | {4-[5-(4-Fluorophenyl)-2-methylsulfanyl-1H-imidazol-4-yl]-pyridin-2-yl}-(tetrahydropyran-4-yl)amine | 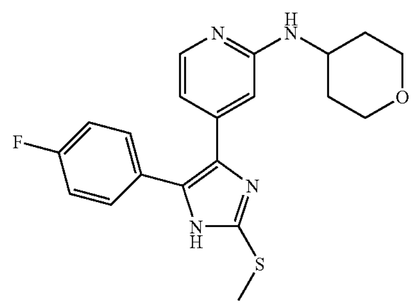 |
| 55 | C | (1-Ethylpyrrolidin-2-ylmethyl)-{4-[5-(4-fluorophenyl)-2-methylsulfanyl-1H-imidazol-4-yl]pyridin-2-yl}amine | 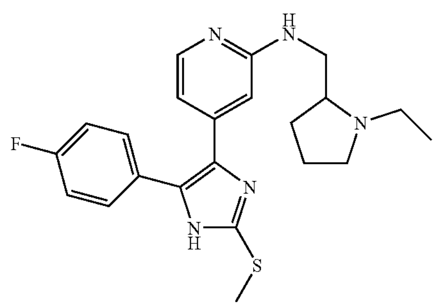 |
| 56 | C | {4-[5-(4-Fluorophenyl)-2-methylsulfanyl-1H-imidazol-4-yl]pyridin-2-yl}-(2-piperidin-1-ylethyl)amine | 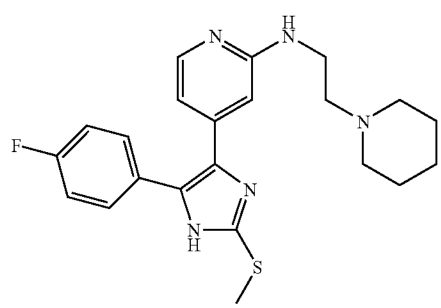 |
| 57 | C | {4-[5-(4-Fluorophenyl)-2-methylsulfanyl-1H-imidazol-4-yl]pyridin-2-yl}-(2-morpholin-4-ylethyl)amine | 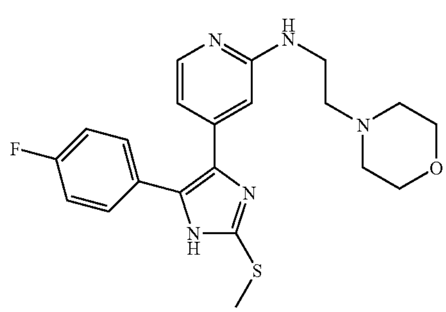 |

TABLE 5-continued

| Ex. | Process | Name | Structure |
|---|---|---|---|
| 58 | C | {4-[5-(4-Fluorophenyl)-2-methylsulfanyl-1H-imidazol-4-yl]pyridin-2-yl}-(1-methylpiperidin-4-yl)-amine | 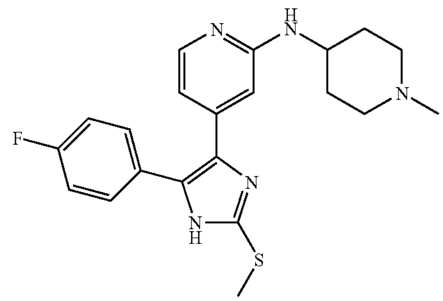 |
| 59 | C | {4-[5-(4-Fluorophenyl)-2-methylsulfanyl-1H-imidazol-4-yl]pyridin-2-yl}-[2-(4-methylpiperazin-1-yl)ethyl]amine | 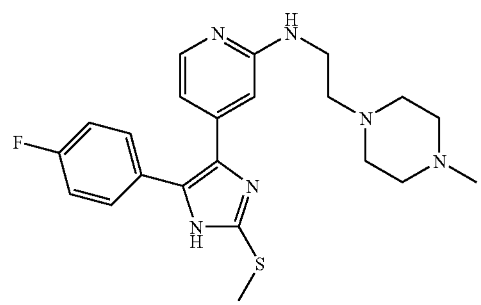 |
| 60 | C | {4-[5-(4-Fluorophenyl)-2-methylsulfanyl-1H-imidazol-4-yl]pyridin-2-yl}-(1-naphthalen-2-ylethyl)amine | 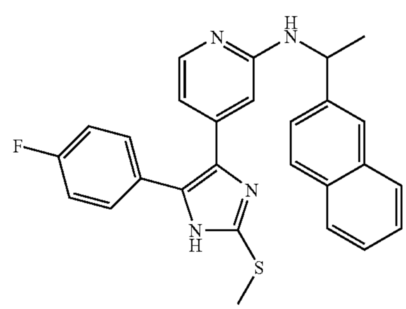 |
| 61 | H | 2,2-Diphenylethyl-{4-[5-(4-fluorophenyl)-2-methylsulfanyl-1H-imidazol-4-yl]pyridin-2-yl}amine | 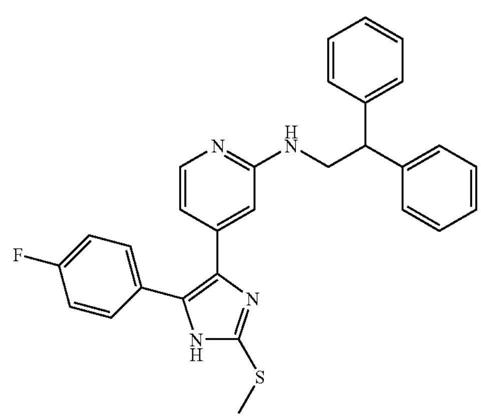 |

TABLE 5-continued

| Ex. | Process | Name | Structure |
|---|---|---|---|
| 62 | H | Biphenyl-2-ylmethyl-{4-[5-(4-fluorophenyl)-2-methylsulfanyl-1H-imidazol-4-yl]pyridin-2-yl}amine | 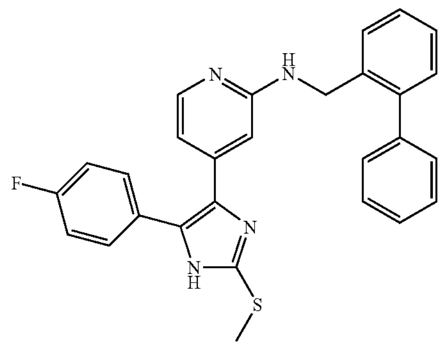 |
| 63 | H | {4-[5-(4-Fluorophenyl)-2-methylsulfanyl-1H-imidazol-4-yl]pyridin-2-yl}-(3-phenylpropyl)amine | 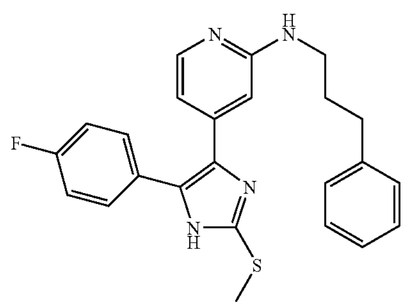 |
| 64 | C | {4-[5-(4-Fluorophenyl)-2-methylsulfanyl-1H-imidazol-4-yl]pyridin-2-yl}-indan-2-ylamine | 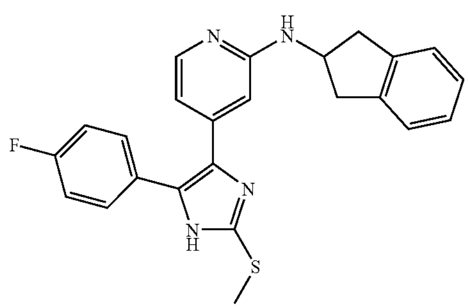 |
| 65 | C | {4-[5-(4-Fluorophenyl)-2-methylsulfanyl-1H-imidazol-4-yl]pyridin-2-yl}-(1,2,3,4-tetrahydronaphthalen-1-yl)amine | 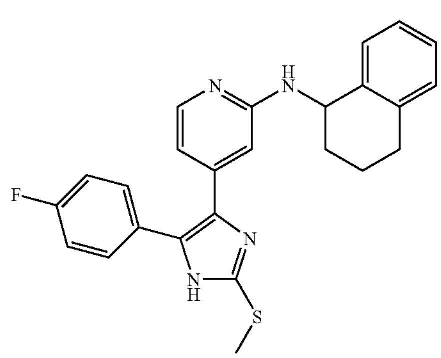 |

TABLE 5-continued

| Ex. | Process | Name | Structure |
|---|---|---|---|
| 66 | C | {4-[5-(4-Fluorophenyl)-2-methylsulfanyl-1H-imidazol-4-yl]pyridin-2-yl}-(1,2,3,4-tetrahydronaphthalen-2-yl)amine | 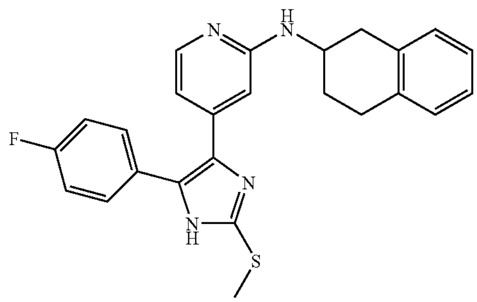 |
| 67 | C | {4-[5-(4-Fluorophenyl)-2-methylsulfanyl-1H-imidazol-4-yl]pyridin-2-yl}quinolin-2-ylmethylamine | 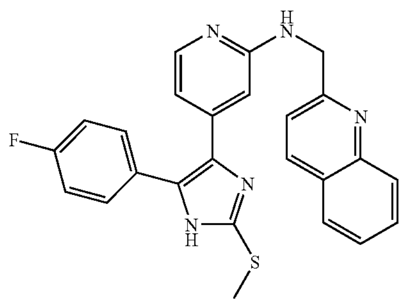 |
| 68 | C | {4-[5-(4-Fluorophenyl)-2-methylsulfanyl-1H-imidazol-4-yl]pyridin-2-yl}pyridin-4-ylmethylamine | 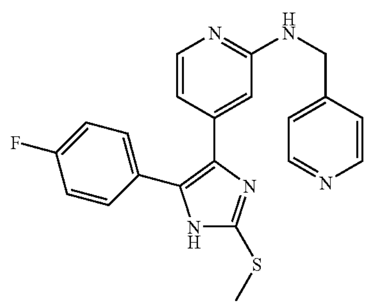 |
| 69 | C | {4-[5-(4-Fluorophenyl)-2-methylsulfanyl-1H-imidazol-4-yl]pyridin-2-yl}-quinolin-4-ylmethylamine | 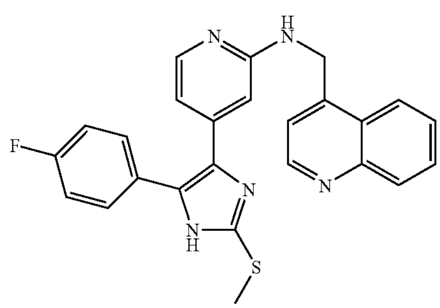 |
| 70 | H | [1-(5-Chlorothiophen-2-yl)ethyl]-{4-[5-(4-fluorophenyl)-2-methylsulfanyl-1H-imidazol-4-yl]pyridin-2-yl}amine | 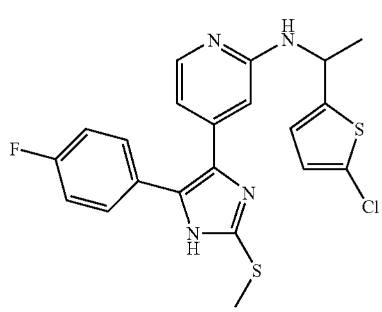 |

TABLE 5-continued

| Ex. | Process | Name | Structure |
|---|---|---|---|
| 71 | C | {4-[5-(4-Fluorophenyl)-2-methylsulfanyl-1H-imidazol-4-yl]pyridin-2-yl}-thiophen-3-ylmethylamine | 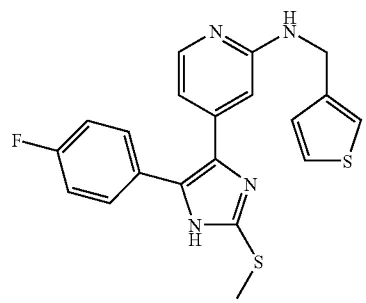 |
| 72 | C | Benzo[b]thiophen-2-ylmethyl-{4-[5-(4-fluorophenyl)-2-methylsulfanyl-1H-imidazol-4-yl]pyridin-2-yl}amine | 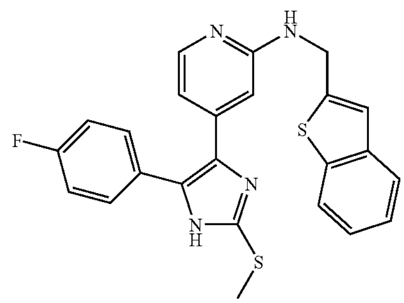 |
| 73 | C | Benzofuran-2-ylmethyl-{4-[5-(4-fluorophenyl)-2-methylsulfanyl-1H-imidazol-4-yl]pyridin-2-yl}amine | 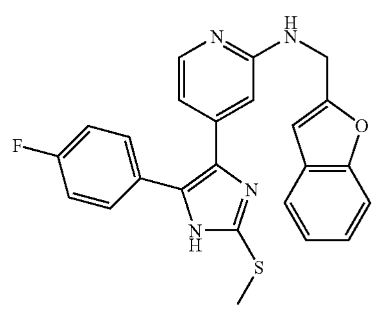 |
| 74 | H | (1-Benzofuran-2-yl-ethyl)-{4-[5-(4-fluorophenyl)-2-methylsulfanyl-1H-imidazol-4-yl]pyridin-2-yl}amine | 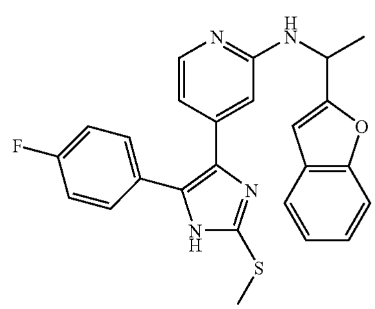 |
| 75 | C | (2,3-Dihydrobenzofuran-2-ylmethyl)-{4-[5-(4-fluorophenyl)-2-methylsulfanyl-1H-imidazol-4-yl]pyridine-2-yl}amine | 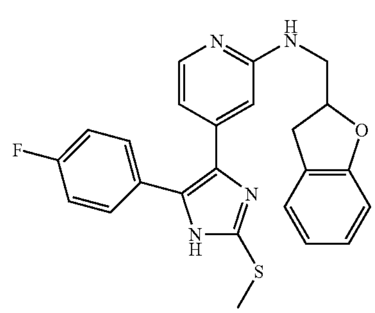 |

TABLE 5-continued

| Ex. | Process | Name | Structure |
|---|---|---|---|
| 76 | C | {4-[5-(4-Fluorophenyl)-2-methylsulfanyl-1H-imidazol-4-yl]pyridin-2-yl}-oxazol-2-ylmethylamine | 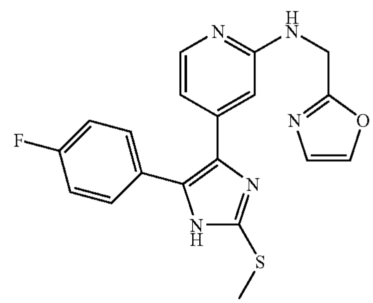 |
| 77 | C | Benzoxazol-2-ylmethyl-{4-[5-(4-fluorophenyl)-2-methylsulfanyl-1H-imidazol-4-yl]pyridin-2-yl}amine | 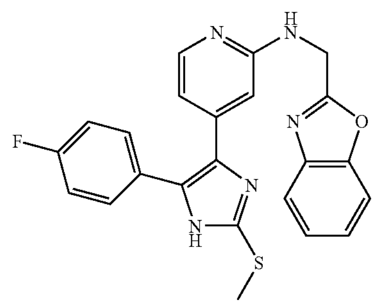 |
| 78 | C | 2-({4-[5-(4-Fluorophenyl)-2-methylsulfanyl-1H-imidazol-4-yl]pyridin-2-ylamino}methyl)-4-isopropyloxazol-5-ol | 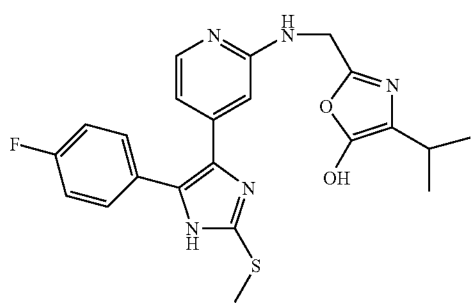 |
| 79 | C | N-{4-[5-(4-Fluorophenyl)-2-methylsulfanyl-1H-imidazol-4-yl]pyridin-2-yl}-N'-(2-methylsulfanylvinyl)formamidine | 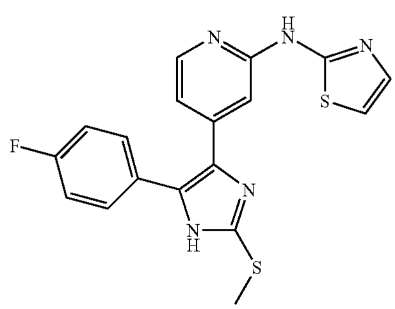 |
| 80 | C | N-{4-[5-(4-Fluorophenyl)-2-methylsulfanyl-1H-imidazol-4-yl]pyridin-2-yl}-N'-(1-methyl-2-methylsulfanylpropenyl)formamidine | 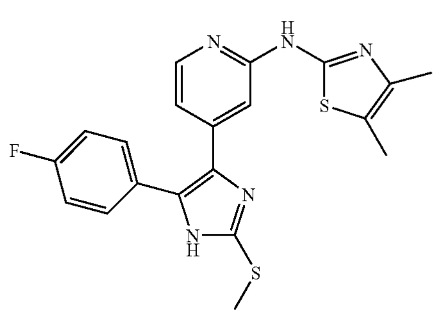 |

TABLE 5-continued

| Ex. | Process | Name | Structure |
|---|---|---|---|
| 81 | C | N-{4-[5-(4-Fluorophenyl)-2-methylsulfanyl-1H-imidazol-4-yl]pyridin-2-yl}-N'-(2-methyl-sulfanylphenyl)formamidine | 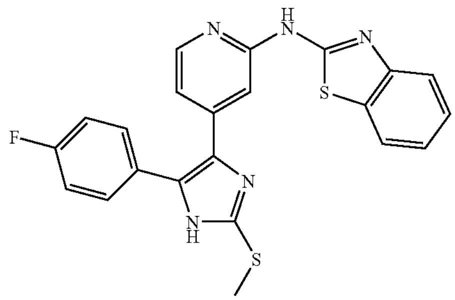 |
| 82 | C | {4-[5-(4-Fluorophenyl)-2-methylsulfanyl-1H-imidazol-4-yl]pyridin-2-yl}-(2-methylthiazol-5-ylmethyl)amine | 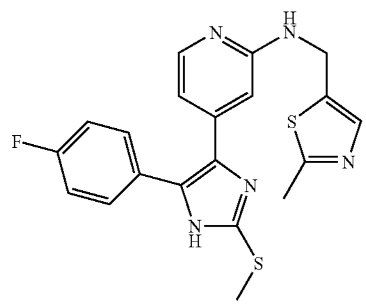 |
| 83 | C | {4-[5-(4-Fluorophenyl)-2-methylsulfanyl-1H-imidazol-4-yl]pyridin-2-yl}-(2-methylthiazol-4-ylmethyl)amine | 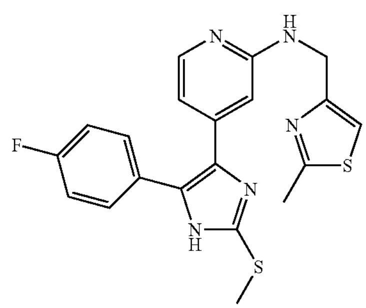 |
| 84 | C | {4-[5-(4-Fluorophenyl)-2-methyl-sulfanyl-1H-imidazol-4-yl]pyridin-2-yl}-[2-(2-methyleneamino-phenylsulfanyl)-ethyl]amine | 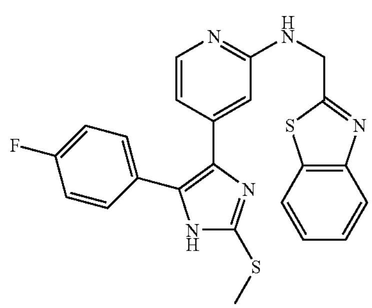 |
| 85 | B | 2-Bromo-4-[5-(4-fluorophenyl)-2-methylsulfanyl-1H-imidazol-4-yl]pyridine | 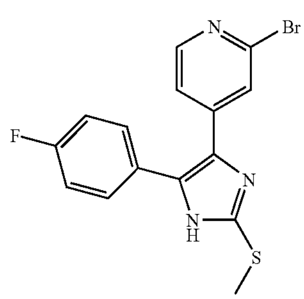 |

TABLE 5-continued

| Ex. | Process | Name | Structure |
|---|---|---|---|
| 86 | G | 2-Azido-4-[5-(4-fluorophenyl)-2-methylsulfanyl-1H-imidazol-4-yl]pyridine | 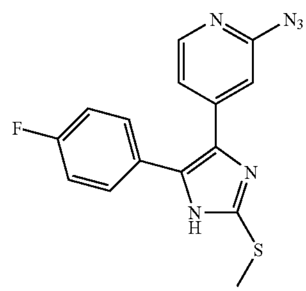 |
| 87 | D | 2-Ethoxy-4-[5-(4-fluorophenyl)-2-methylsulfanyl-1H-imidazol-4-yl]pyridine | 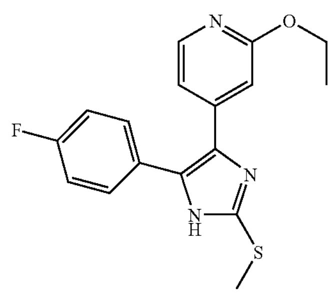 |
| 88 | C | 4-[5-(4-Fluorophenyl)-2-methylsulfanyl-1H-imidazol-4-yl]-2-p-tolyloxypyridine | 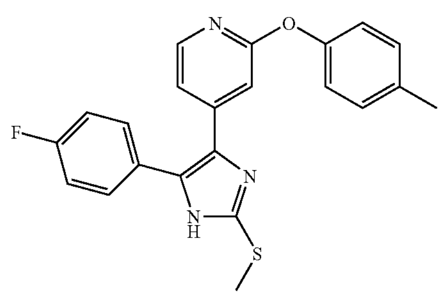 |
| 89 | C | 2-(2,6-Dichlorophenoxy)-4-[5-(4-fluorophenyl)-2-methylsulfanyl-1H-imidazol-4-yl]pyridine | 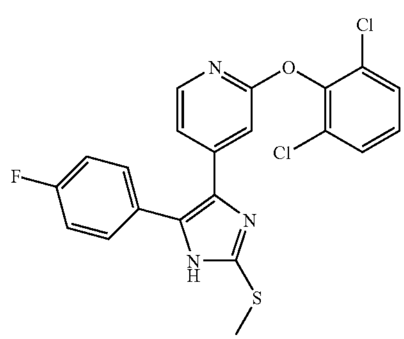 |
| 90 | D | 2-Benzyloxy-4-[5-(4-fluorophenyl)-2-methylsulfanyl-1H-imidazol-4-yl]pyridine | 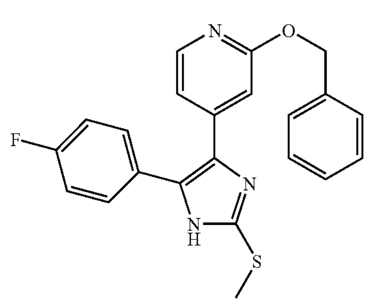 |

TABLE 5-continued

| Ex. | Process | Name | Structure |
|---|---|---|---|
| 91 | D | 4-[5-(4-Fluorophenyl)-2-methylsulfanyl-1H-imidazol-4-yl]-2-phenethyloxypyridine | 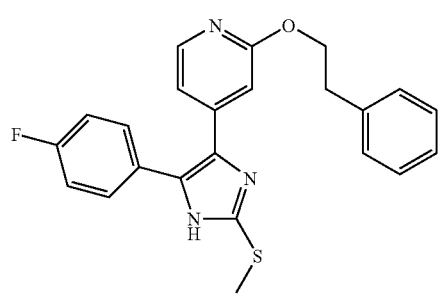 |
| 92 | D | 2-Cyclohexyloxy-4-[5-(4-fluorophenyl)-2-methylsulfanyl-1H-imidazol-4-yl]pyridine | 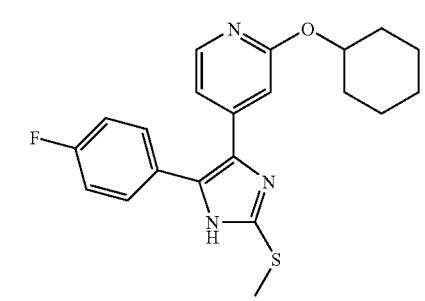 |
| 93 | C | 4-[5-(4-Fluorophenyl)-2-methylsulfanyl-1H-imidazol-4-yl]-2-(tetrahydrofuran-3-yloxy)pyridine | 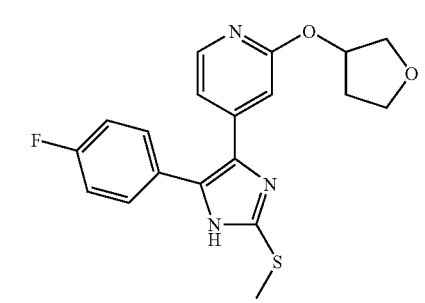 |
| 94 | D | 6-{4-[5-(4-Fluorophenyl)-2-methylsulfanyl-1H-imidazol-4-yl]pyridin-2-yloxy}hexahydrofuro[3.2-b]furan-3-ol | 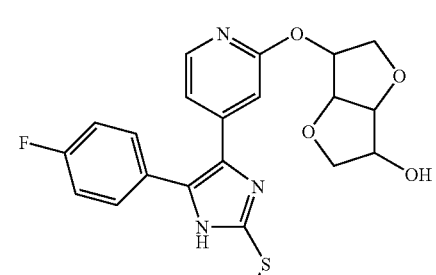 |
| 95 | C | 4-[5-(4-Fluorophenyl)-2-methylsulfanyl-1H-imidazol-4-yl]-2-(tetrahydrofuran-2-ylmethoxy)pyridine | 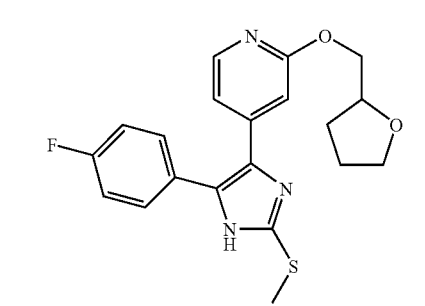 |

TABLE 5-continued

| Ex. | Process | Name | Structure |
|---|---|---|---|
| 96 | C | 4-[5-(4-Fluorophenyl)-2-methylsulfanyl-1H-imidazol-4-yl]-2-(tetrahydropyran-2-ylmethoxy)-pyridine | 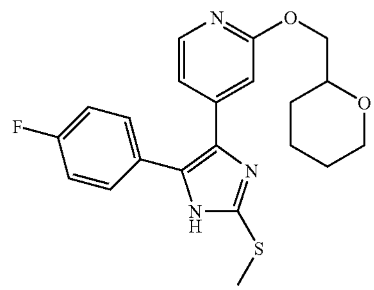 |
| 97 | C | 2-(Benzofuran-2-ylmethoxy)-4-[5-(4-fluorophenyl)-2-methylsulfanyl-1H-imidazol-4-yl]pyridine | 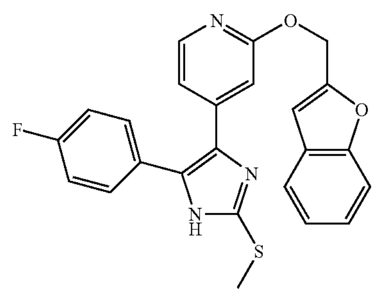 |
| 98 | C | 4-[5-(4-Fluorophenyl)-2-methylsulfanyl-1H-imidazol-4-yl]-2-(furan-2-ylmethoxy)pyridine | 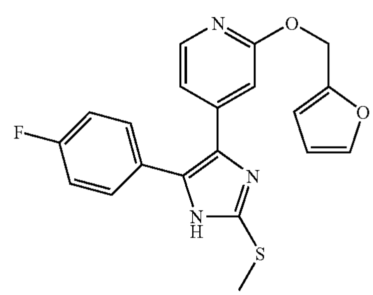 |
| 99 | C | 4-[5-(4-Fluorophenyl)-2-methylsulfanyl-1H-imidazol-4-yl]-2-(thiophen-2-ylmethoxy)pyridine | 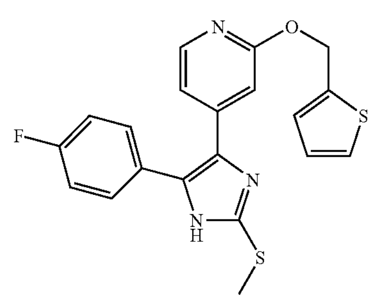 |
| 100 | C | 4-[5-(4-Fluorophenyl)-2-methylsulfanyl-1H-imidazol-4-yl]-2-(5-chlorothiophen-2-yl-methoxy)pyridine | 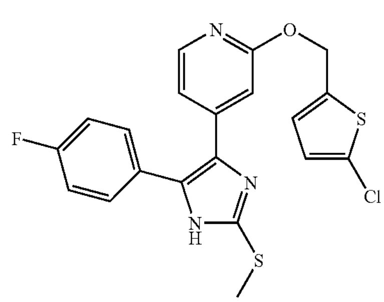 |

TABLE 5-continued

| Ex. | Process | Name | Structure |
|---|---|---|---|
| 101 | C | 4-[5-(4-Fluorophenyl)-2-methylsulfanyl-1H-imidazol-4-yl]-2-(thiophen-3-ylmethoxy)pyridine | 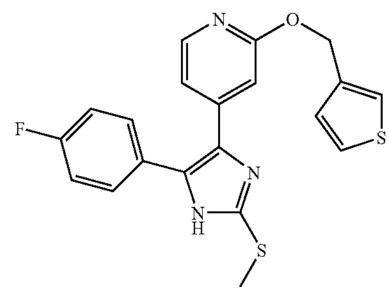 |
| 102 | C | 4-[5-(4-Fluorophenyl)-2-methylsulfanyl-1H-imidazol-4-yl]-2-(thiazol-2-ylmethoxy)pyridine | 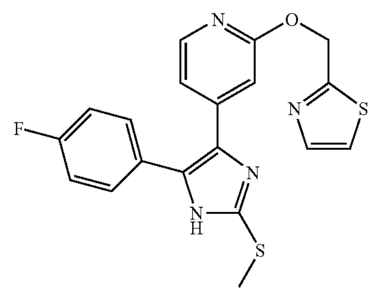 |
| 103 | C | Bicyclo[2.2.1]hept-2-yl-{4-[5-(4-fluorophenyl)-2-methylsulfanyl-1H-imidazol-4-yl]pyridin-2-yl}amine | 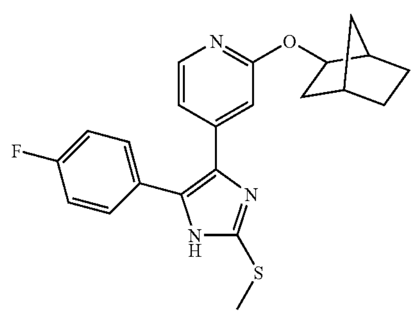 |
| 104 | C | 3-{4-[5-(4-Fluorophenyl)-2-methylsulfanyl-1H-imidazol-4-yl]pyridin-2-yloxy}-1-azabicyclo[2.2.2]octane | 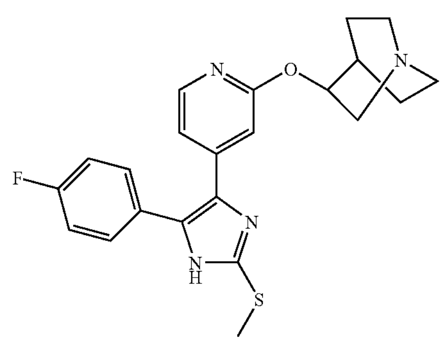 |
| 105 | C | 4-[5-(4-Fluorophenyl)-2-methylsulfanyl-1H-imidazol-4-yl]-2-methylsulfanylpyridine | 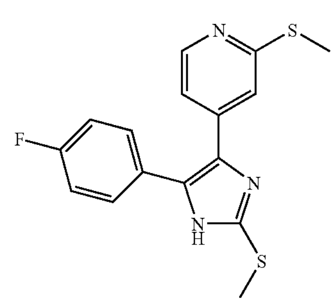 |

TABLE 5-continued

| Ex. | Process | Name | Structure |
|---|---|---|---|
| 106 | C | 2-Benzenesulfonyl-4-[5-(4-fluorophenyl)-2-methylsulfanyl-1H-imidazol-4-yl]pyridine | 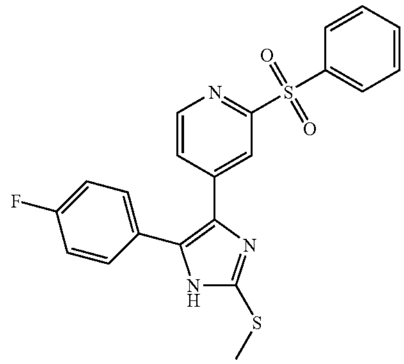 |
| 107 | C | 4-[5-(4-Fluorophenyl)-2-methylsulfanyl-1H-imidazol-4-yl]-2-phenylsulfanylpyridine | 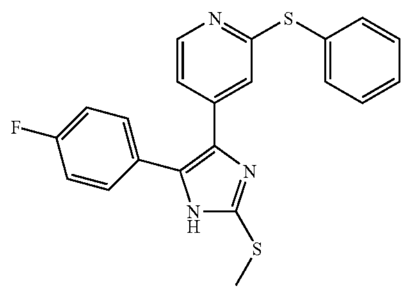 |
| 108 | C | 2-Ethylsulfanyl-4-[5-(4-fluorophenyl)-2-methylsulfanyl-1H-imidazol-4-yl]pyridine | 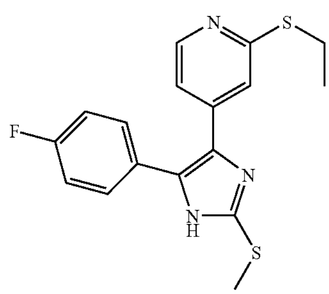 |
| 109 | C | 2-{4-[5-(4-Fluorophenyl)-2-methylsulfanyl-1H-imidazol-4-yl]pyridin-2-ylsulfanyl}ethanol | 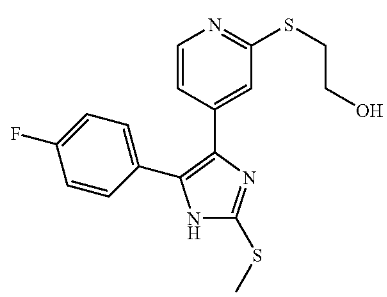 |
| 110 | C | 3-{4-[5-(4-Fluorophenyl)-2-methylsulfanyl-1H-imidazol-4-yl]pyridin-2-ylsulfanyl]propan-1-ol | 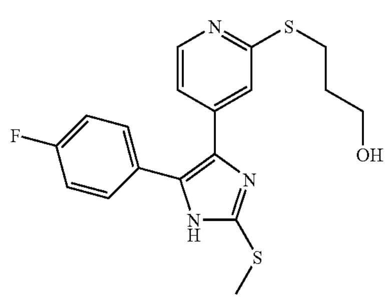 |

TABLE 5-continued

| Ex. | Process | Name |
|---|---|---|
| 110a | E | N-{4-[5-(4-Fluorophenyl)-2-methylsulfanyl-1H-imidazol-4-yl]pyridin-2-yl}formamide |
| 111 | E | N-{4-[5-(4-Fluorophenyl)-2-methylsulfanyl-1H-imidazol-4-yl]pyridin-2-yl}benzamide |
| 112 | E | 4-Chloro-N-{4-[5-(4-fluorophenyl)-2-methylsulfanyl-1H-imidazol-4-yl]pyridin-2-yl}benzamide |
| 113 | E | N-{4-[5-(4-Fluorophenyl)-2-methylsulfanyl-1H-imidazol-4-yl]pyridin-2-yl}-3-methylbenzamide |
| 114 | E | N-{4-[5-(4-Fluorophenyl)-2-methylsulfanyl-1H-imidazol-4-yl]pyridin-2-yl}-3-trifluoromethylbenzamide |

TABLE 5-continued

| Ex. | Process | Name | Structure |
|---|---|---|---|
| 115 | F | N-{4-[5-(4-Fluorophenyl)-2-methylsulfanyl-1H-imidazol-4-yl]pyridin-2-yl}-2-phenylacetamide | 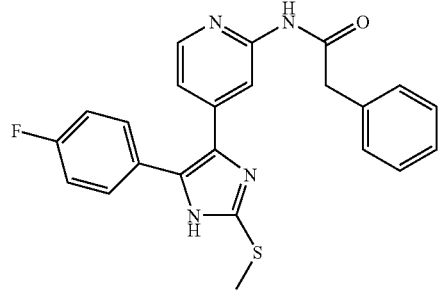 |
| 116 | F | Cyclohexanecarboxylic acid {4-[5-(4-fluorophenyl)-2-methylsulfanyl-1H-imidazol-4-yl]pyridin-2-yl}amide | 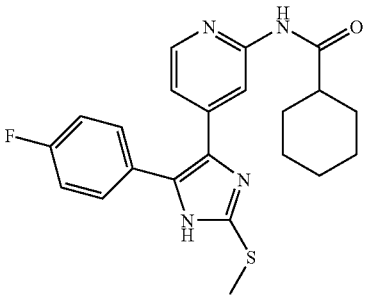 |
| 117 | F | 2-Cyclohexyl-N-{4-[5-(4-fluorophenyl)-2-methylsulfanyl-1H-imidazol-4-yl]pyridin-2-yl}acetamide | 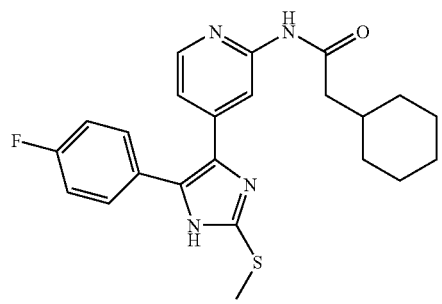 |
| 118 | F | 2-(4-Chlorophenyl)-N-{4-[5-(4-fluorophenyl)-2-methylsulfanyl-1H-imidazol-4-yl]pyridin-2-yl}acetamide | 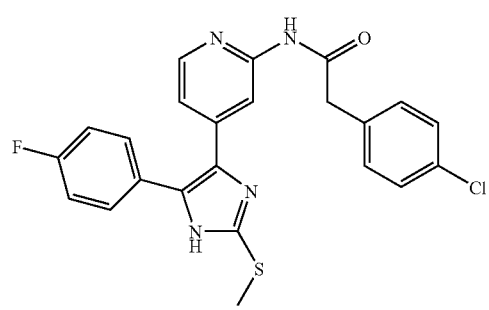 |
| 119 | F | N-{4-[5-(4-Fluorophenyl)-2-methylsulfanyl-1H-imidazol-4-yl]pyridin-2-yl}-2-(4-methoxyphenyl)acetamide | 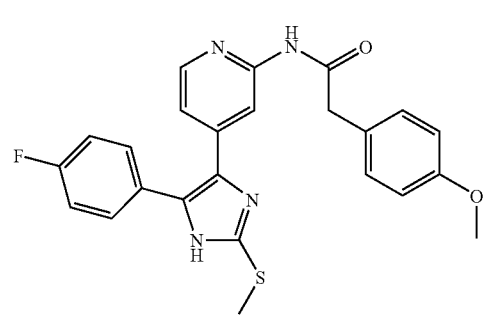 |

TABLE 5-continued

| Ex. | Process | Name | Structure |
|---|---|---|---|
| 120 | F | 2-(4-Fluorophenyl)-N-{4-[5-(4-fluorophenyl)-2-methylsulfanyl-1H-imidazol-4-yl]pyridin-2-yl}acetamide | 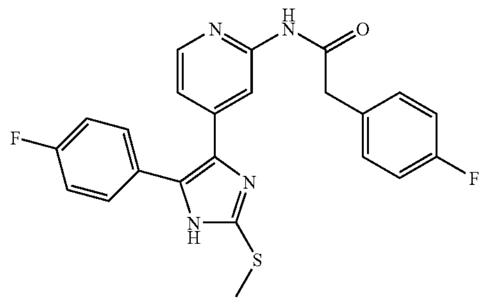 |
| 121 | F | 2-(2-Fluorophenyl)-N-{4-[5-(4-fluorophenyl)-2-methylsulfanyl-1H-imidazol-4-yl]pyridin-2-yl}acetamide | 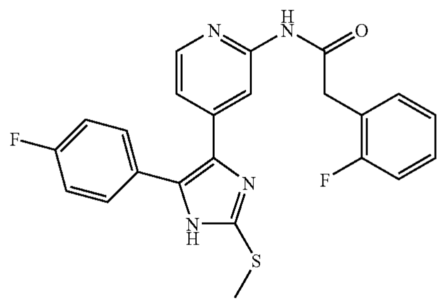 |
| 122 | F | N-{4-[5-(4-Fluorophenyl)-2-methylsulfanyl-1H-imidazol-4-yl]-pyridin-2-yl}-3-phenylpropionamide | 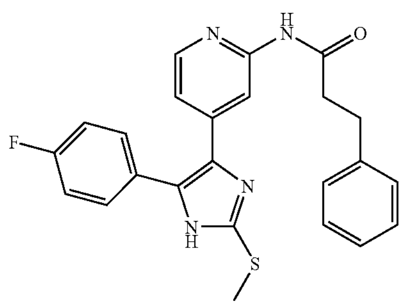 |
| 123 | F | N-{4-[5-(4-Fluorophenyl)-2-methylsulfanyl-1H-imidazol-4-yl]pyridin-2-yl}-3-phenylacrylamide | 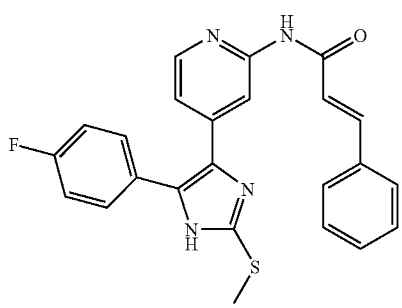 |
| 124 | F | {4-[5-(4-Fluorophenyl)-2-methylsulfanyl-1H-imidazol-4-yl]pyridin-2-yl}-carbamic acid benzyl ester | 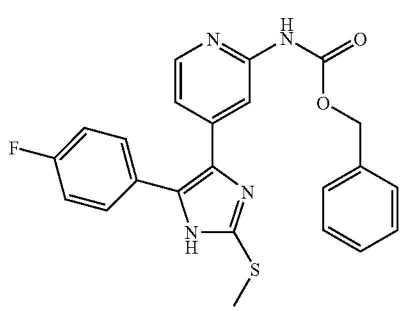 |

TABLE 5-continued

| Ex. | Process | Name | Structure |
|---|---|---|---|
| 125 | F | 1-Benzoyl-3-{4-[5-(4-fluorophenyl)-2-methylsulfanyl-1H-imidazol-4-yl]pyridin-2-yl}urea | 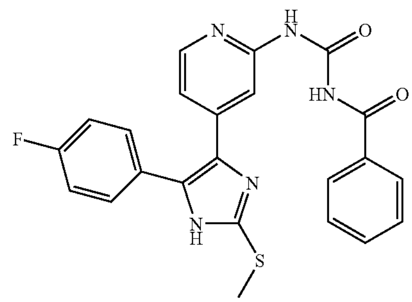 |
| 126 | E | N-{4-[5-(4-Fluorophenyl)-2-methylsulfanyl-1H-imidazol-4-yl]pyridin-2-yl]acetamide | 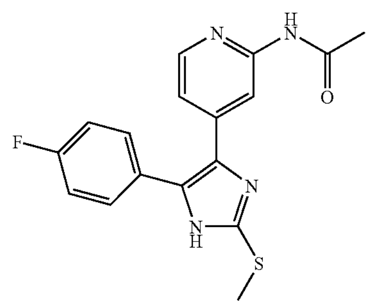 |
| 127 | F | 2,2,2-Trifluoro-N-{4-[5-(4-fluorophenyl)-2-methylsulfanyl-1H-imidazol-4-yl]pyridin-2-yl}acetamide | 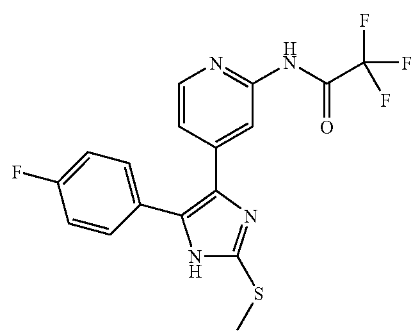 |
| 128 | F | N-{4-[5-(4-Fluorophenyl)-2-methylsulfanyl-1H-imidazol-4-yl]pyridin-2-yl}-2-methoxyacetamide | 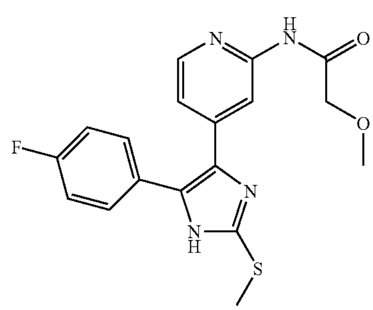 |
| 129 | F | N-{4-[5-(4-Fluorophenyl)-2-methylsulfanyl-1H-imidazol-4-yl]pyridin-2-yl}-2-(methylphenylamino)acetamide | 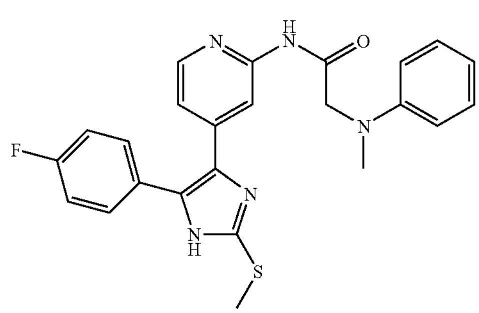 |

TABLE 5-continued

| Ex. | Process | Name | Structure |
|---|---|---|---|
| 130 | F | {4-[5-(4-Fluorophenyl)-2-methylsulfanyl-1H-imidazol-4-yl]pyridin-2-yl}-carbamic acid cyclohexyl ester | 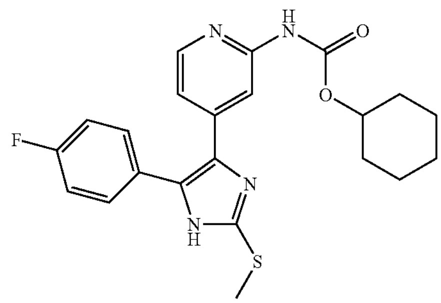 |
| 131 | C | {4-[5-(2,4-Difluorophenyl)-2-methylsulfanyl-1H-imidazol-4-yl]pyridin-2-yl}isopropylamine | 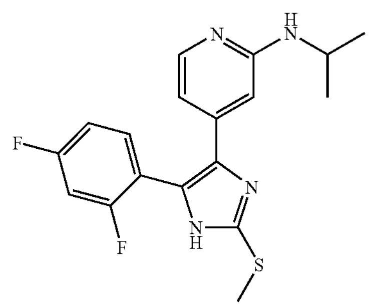 |
| 132 | C | {4-[5-(2,4-Difluorophenyl)-2-ethylsulfanyl-1H-imidazol-4-yl]pyridin-2-yl}isopropylamine | 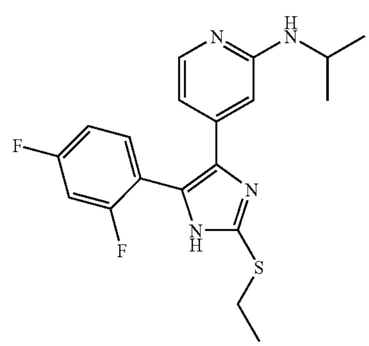 |
| 133 | C | {4-[5-(2,4-Difluorophenyl)-2-isopropylsulfanyl-1H-imidazol-4-yl]pyridin-2-yl}isopropylamine | 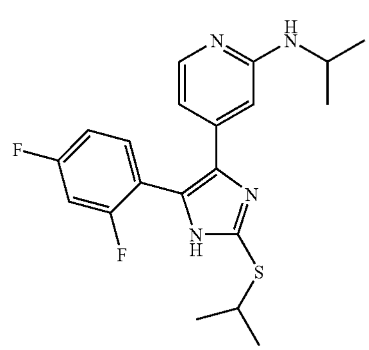 |

TABLE 5-continued

| Ex. | Process | Name | Structure |
|---|---|---|---|
| 134 | F | Isopropyl-{4-[2-methylsulfanyl-5-(3-trifluoromethylphenyl)-1H-imidazol-4-yl]pyridin-2-yl}amine | 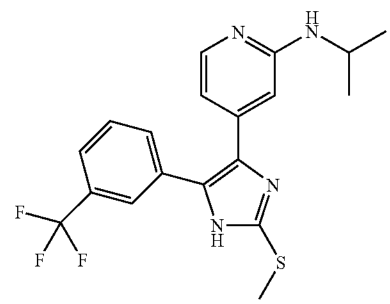 |
| 135 | F | {4-[2-Ethylsulfanyl-5-(3-trifluoromethylphenyl)-1H-imidazol-4-yl]pyridin-2-yl}isopropylamine | 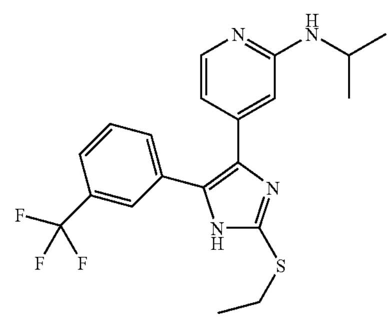 |
| 136 | F | {4-[5-(2,4-Difluorophenyl)-2-methylsulfanyl-1H-imidazol-4-yl]pyridin-2-yl}-(2-methoxyethyl)amine | 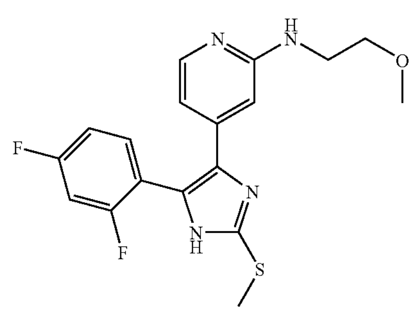 |
| 137 | F | {4-[5-(4-Fluorophenyl)-2-methylsulfonyl-1H-imidazol-4-yl]pyridin-2-yl}urea | 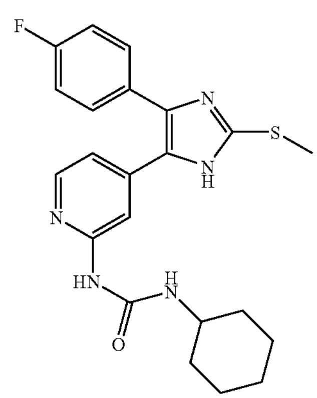 |

TABLE 5-continued

| Ex. | Process | Name | Structure |
|---|---|---|---|
| 138 | F | N-{4-[5-(4-Fluorophenyl)-2-methylsulfonyl-1H-imidazol-4-yl]pyridin-2-yl-2-(4-isobutylphenyl)propionamide | 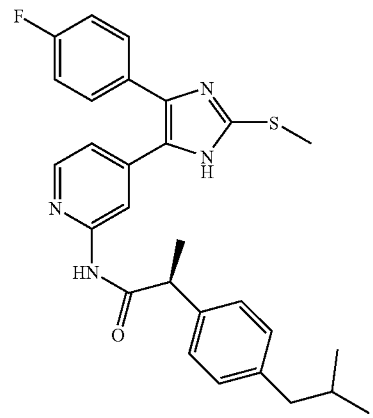 |

We claim:

1. A 2-thio-substituted imidazole derivative compound of the formula I

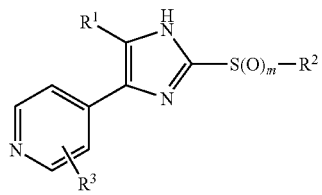

wherein
R$^1$ is aryl which may or may not be substituted by a halogen atom;
R$^2$ is selected from the group consisting of
  a) aryl-C$_1$-C$_4$-alkyl, and
  b) C$_1$-C$_6$-alkyl;
R$^3$ is selected from the group consisting of
  a) NR$^4$R$^{10}$
  b) NR$^7$COR$^{10}$, and
  c) C$_1$-C$_6$-alkoxy;
R$^4$ is H;
R$^{10}$ is

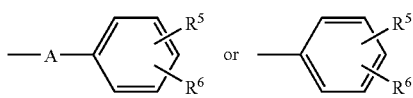

or, if R$^3$ is NR$^7$COR$^{10}$, R$^{10}$ is R$^8$,
R$^5$ and R$^6$, which may be identical or different, are H, halogen, C$_1$-C$_6$-alkoxy or C$_1$-C$_6$-alkyl;
R$^7$ is H, C$_1$-C$_6$-alkyl or benzyl;
R$^8$ is C$_1$-C$_4$-alkyl, C$_3$-C$_6$-cycloalkyl or phenyl, where the phenyl group may have one or two substituents independently of one another selected from the group consisting of C$_1$-C$_4$-alkyl, C$_1$-C$_4$-alkoxy and halogen;
A is straight-chain or branched C$_1$-C$_6$-alkylene or C$_2$-C$_6$-alkenylene and m is 0, 1 or 2;
or a tautomer, an optical isomer or a physiologically acceptable salt thereof.

2. The compound as claimed in claim 1, which has the formula Ia:

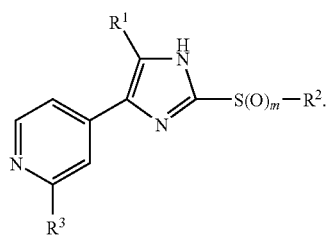

3. The compound as claimed in claim 1, wherein R$^3$ is

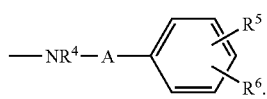

4. The compound as claimed in claim 3, wherein A is C$_1$-C$_2$-alkylene.

5. The compound as claimed in claim 3, wherein A is ethylidene.

6. The compound as claimed in claim 3, wherein R$^5$ and R$^6$ are H.

7. The compound as claimed in claim 1, wherein R$^1$ is 4-fluorophenyl.

8. A pharmaceutical composition, comprising at least one compound as claimed in claim 1, and one or more pharmaceutically acceptable carriers and/or additives.

9. A method for treating inflammatory disorders in which TNF-α and IL-β are involved which comprises administering to a person in need of such a treatment an amount of a compound as claimed in claim 1 sufficient to have anti-inflammatory action.

10. A 2-thio-substituted imidazole derivative compound of the formula I

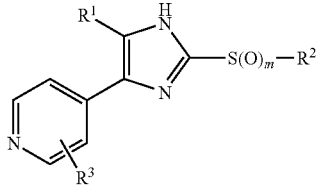

wherein
$R^1$ is aryl which is substituted by a halogen atom or by halo-$C_1$-$C_6$-alkyl;
$R^2$ is selected from the group consisting of
  a) aryl-$C_1$-$C_4$-alkyl, and
  b) $C_1$-$C_6$-alkyl;
$R^3$ selected from the group consisting of
  a) $NR^4R^{10}$,
  b) $NR^7COR^{10}$,
  c) $OR^{10}$, and
  d) $NH_2$;
$R^4$ is H, —$COR^{14}$, —$CO_2R^{14}$, —$CONH_2$, —$CONHR^{14}$, —$CHR^{16}$—$OR^{14}$, —$CHR^{16}$—O—$COR^{14}$, —COC$(R^{16})_2$—OH, —$COR^{15}$, $SO_2R^{15}$ or —$SO_2R^{14}$, $R^{14}$ is $C_1$-$C_6$-alkyl or $CF_3$, $R^{15}$ is phenyl or tolyl, and $R^{16}$ is H or $C_1$-$C_6$-alkyl;
$R^5$ and $R^6$, which may be identical or different, are H, halogen, $C_1$-$C_6$-alkoxy, $C_1$-$C_6$-alkyl or halo-$C_1$-$C_6$-alkyl;
$R^7$ is H;
$R^{10}$ has one of the meanings below:

a) A—B,

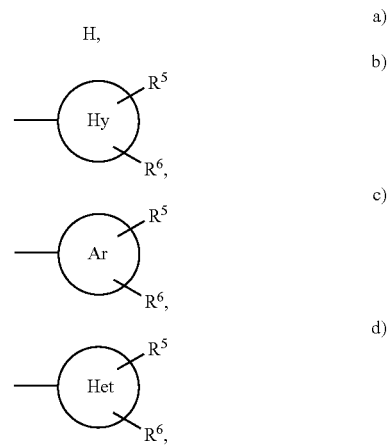

f) $C_1$-$C_6$-alkyl which is substituted by 2 phenyl groups, or
g) trifluoromethyl;
A is straight-chain or branched $C_1$-$C_6$-alkylene or $C_2$-$C_6$-alkenylene;

B is selected from the group consisting of a) H, b), c), d) [ring structures with $R^5$, $R^6$ substituents on Hy, Ar, Het]

e) $OC_1$-$C_6$-alkyl, and
f) OH;
Hy is a 3- to 10-membered non-aromatic mono-, bi- or tricyclic carbocycle which may or may not be fused with a benzene ring;
Ar is a 5- or 6-membered aromatic heterocycle which has 1, 2 or 3 heteroatoms independently of one another selected from the group consisting of O, S and N and which may or may not be fused with a benzene ring;
Het is a 5- or 6-membered non-aromatic heterocycle which has 1, 2 or 3 heteroatoms independently of one another selected from the group consisting of O, S and N which may or may not be fused with a benzene ring and which may or may not be bridged bicyclically or tricyclically;
m is 0, 1 or 2;
or a tautomer, an optical isomer or a physiologically acceptable salt thereof.

11. The compound as claimed in claim 10, which has formula Ia:

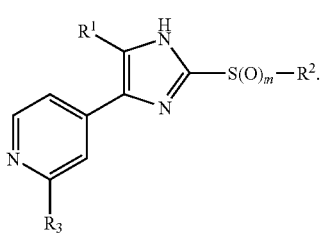

12. The compound as claimed in claim 10, wherein $R^{10}$ is A-B and B is selected from the group consisting of $OC_1$-$C_6$-alkyl and OH.

13. The compound as claimed in claim 10, wherein $R^3$ is $NR^7COR^{10}$, and $R^{10}$ is selected from the group consisting of —O—$C_1$-$C_4$-alkylphenyl, phenyl and $C_2$-$C_6$-alkenyl which is substituted by phenyl.

14. The compound as claimed in claim 10, wherein A is $C_1$-$C_2$-alkylene.

15. The compound as claimed in claim 10, wherein A is ethylidene.

16. The compound as claimed in claim 10, wherein $R^5$ and $R^6$ are H.

17. The compound as claimed in claim 10, wherein $R^1$ is halogen-substituted phenyl or $CF_3$-substituted phenyl.

18. A pharmaceutical composition, comprising at least one compound as claimed in claim 10, and one or more pharmaceutically acceptable carriers and/or additives.

19. A method for treating inflammatory disorders in which TNF-α and IL-β are involved which comprises administering to a person in need of such a treatment an amount of a compound as claimed in claim 10 sufficient to have anti-inflammatory action.

20. The compound as claimed in claim 10, which is {4-[5-(4-fluorophenyl)-2-methylsulfanyl-1H-imidazol-4-yl]-pyridin-2-yl}-(tetrahydropyran-4-yl)amine.

21. The method according to claim 9, wherein the inflammatory disorder is rheumatoid arthritis.

22. The method according to claim 19, wherein the inflammatory disorder is rheumatoid arthritis.

23. The compound as claimed in claim 10, wherein $R^{10}$ has one of the meanings below:

a) A—B, b) 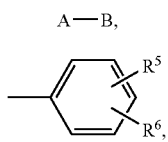

-continued c) 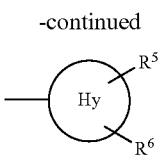

f) $C_1$-$C_6$-alkyl which is substituted by 2 phenyl groups, or g) trifluoromethyl;

and when $R^{10}$ is A-B, B is selected from the group consisting of a) H, b) 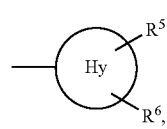

e) $OC_1$-$C_6$-alkyl, and f) OH.

* * * * *